(12) United States Patent
Hyde et al.

(10) Patent No.: US 9,919,112 B2
(45) Date of Patent: Mar. 20, 2018

(54) ACTIVE LUBRICATION OF PENETRATING DEVICES

(71) Applicant: Elwha LLC, Bellevue, WA (US)

(72) Inventors: Roderick A. Hyde, Redmond, WA (US); Muriel Y. Ishikawa, Livermore, CA (US); Nathan P. Myhrvold, Medina, WA (US); Elizabeth A. Sweeney, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 797 days.

(21) Appl. No.: 14/319,850

(22) Filed: Jun. 30, 2014

(65) Prior Publication Data

US 2015/0374930 A1     Dec. 31, 2015

(51) Int. Cl.
*A61M 5/32* (2006.01)
*A61M 5/14* (2006.01)
(Continued)

(52) U.S. Cl.
CPC ........ *A61M 5/3294* (2013.01); *A61M 5/1407* (2013.01); *A61M 5/3286* (2013.01); *A61M 5/3291* (2013.01); *A61M 5/422* (2013.01); *G06F 19/3468* (2013.01); *A61M 5/1452* (2013.01); *A61M 5/1582* (2013.01); *A61M 5/16827* (2013.01); *A61M 5/19* (2013.01); *A61M 5/282* (2013.01); *A61M 2005/1587* (2013.01); *A61M 2005/3201* (2013.01); *A61M 2205/075* (2013.01); *A61M 2205/13* (2013.01); *A61M 2205/3303* (2013.01); *A61M 2205/3306* (2013.01); *A61M 2205/3368* (2013.01); *A61M 2205/3569* (2013.01); *A61M 2205/50* (2013.01)

(58) Field of Classification Search
CPC .............. A61M 5/3294; A61M 5/1582; A61M 5/16827; A61M 5/3291; A61M 5/422; A61M 5/282; A61M 2005/1587; A61M 2205/075; A61M 2005/3201; A61M 5/3297; A61M 2005/3107; A61M 5/3286; A61M 5/3295; A61M 5/1407
See application file for complete search history.

(56) References Cited

U.S. PATENT DOCUMENTS 3,173,418 A    3/1965   Baran
3,638,655 A    2/1972   Doherty
(Continued)

OTHER PUBLICATIONS

Berggren et al.; "Review—Capacitive Biosensors"; Electroanalysis; bearing a date of Jul. 7, 2000; pp. 173-180 (8 total pages); vol. 13—No. 3.
(Continued)

*Primary Examiner* — Bhisma Mehta
*Assistant Examiner* — Nilay Shah

(57) ABSTRACT

Penetrating systems and devices are described herein which include a penetrating portion with two concentric hollow cylinders joined at one end with a substantially ring-shaped end piece and at the other end with a hollow structure forming a fluid reservoir portion, the outer hollow cylinder including a plurality of pores in fluid communication with the fluid reservoir portion, the inner hollow cylinder in fluid communication with a second fluid reservoir portion, and the hollow structure formed at least in part from a deformable material.

39 Claims, 31 Drawing Sheets

(51) Int. Cl.
  *G06F 19/00* (2018.01)
  *A61M 5/42* (2006.01)
  *A61M 5/158* (2006.01)
  *A61M 5/19* (2006.01)
  *A61M 5/28* (2006.01)
  *A61M 5/145* (2006.01)
  *A61M 5/168* (2006.01)

(56) References Cited

U.S. PATENT DOCUMENTS

| | | | |
|---|---|---|---|
| 3,749,084 A | 7/1973 | Cucchiara | |
| 4,186,745 A | 2/1980 | Lewis et al. | |
| 4,230,110 A | 10/1980 | Beroff | |
| 4,384,288 A | 5/1983 | Walton | |
| 4,655,747 A | 4/1987 | Allen, Jr. | |
| 5,053,004 A * | 10/1991 | Markel | A61M 5/1582 29/428 |
| 5,496,284 A | 3/1996 | Waldenburg | |
| 5,718,678 A * | 2/1998 | Fleming, III | A61M 25/0009 604/43 |
| 5,814,022 A | 9/1998 | Antanavich et al. | |
| 5,911,711 A | 6/1999 | Pelkey | |
| 6,425,854 B1 | 7/2002 | Galt et al. | |
| 6,517,521 B1 | 2/2003 | Ly | |
| 6,547,755 B1 | 4/2003 | Lippe et al. | |
| 6,572,584 B1 | 6/2003 | Shaw et al. | |
| 6,605,067 B1 | 8/2003 | Larsen | |
| 6,972,005 B2 | 12/2005 | Boehm, Jr. et al. | |
| 7,118,554 B2 | 10/2006 | Sibbitt | |
| 7,215,976 B2 | 5/2007 | Brideglall | |
| 7,507,675 B2 | 3/2009 | Zuilhof et al. | |
| 7,612,424 B1 | 11/2009 | Espinosa et al. | |
| 7,744,582 B2 | 6/2010 | Sadowski et al. | |
| 8,308,741 B2 | 11/2012 | Hyde et al. | |
| 2002/0065492 A1 | 5/2002 | McGuckin, Jr. et al. | |
| 2003/0149445 A1 | 8/2003 | Knudson et al. | |
| 2004/0092864 A1 | 5/2004 | Boehm, Jr. et al. | |
| 2004/0186422 A1 | 9/2004 | Rioux et al. | |
| 2004/0215130 A1 | 10/2004 | Rioux et al. | |
| 2005/0045183 A1 | 3/2005 | Callister et al. | |
| 2005/0177117 A1 | 8/2005 | Crocker et al. | |
| 2005/0277891 A1 | 12/2005 | Sibbitt | |
| 2006/0259006 A1 | 11/2006 | McKay et al. | |
| 2007/0083155 A1 | 4/2007 | Muller | |
| 2007/0083267 A1 | 4/2007 | Miz et al. | |
| 2007/0197968 A1 | 8/2007 | Pongpairochana et al. | |
| 2008/0125745 A1 | 5/2008 | Basu et al. | |
| 2008/0160480 A1 | 7/2008 | Ruddle et al. | |
| 2009/0240208 A1 | 9/2009 | Cowan | |
| 2010/0042137 A1 | 2/2010 | Oronsky et al. | |
| 2010/0106081 A1 | 4/2010 | Brandeis | |
| 2010/0179478 A1 | 7/2010 | Kobayashi et al. | |
| 2010/0249747 A1 * | 9/2010 | Mills | A01N 37/00 604/506 |
| 2011/0071476 A1 | 3/2011 | Mueller et al. | |
| 2011/0166531 A1 | 7/2011 | Stroumpoulis et al. | |
| 2012/0029469 A1 | 2/2012 | Horvath et al. | |
| 2012/0059333 A1 | 3/2012 | Singhal | |
| 2014/0025035 A1 | 1/2014 | Fischer, Jr. | |

OTHER PUBLICATIONS

Chawla et al.; "Applications & Practice—An Overview of Passive RFID"; IEEE Applications & Practice; Sep. 2007; pp. 11-17.

"Design & Manufacture of Specialty Needle Devices"; Creganna-Tactx Medical; printed on May 1, 2014; pp. 1-3; located at: http://www.cregannatactx.com/technologies/specialty-needles/needle-technologies/.

Cui et al.; "Nanowire Nanosensors for Highly Sensitive and Selective Detection of Biological and Chemical Species"; Science; Aug. 17, 2001; pp. 1289-1292; vol. 293.

Finkenzeller, Klaus; "Fundamental Operating Principles"; RFID Handbook: Fundamentals and Applications in Contactless Smart Cards and Identification; printed on Jun. 30, 2014; pp. 29-59; John Wiley & Sons, Ltd.

Gill et al.; "Does Needle Size Matter?"; Journal of Diabetes Science and Technology; Sep. 2007; pp. 725-729; vol. 1 Issue 5; Diabetes Technology Society.

Hutin et al.; "Best infection control practices for intradermal, subcutaneous, and intramuscular needle injections"; Bulletin of the World Health Organization; printed on Jun. 30, 2014; pp. 491-500; vol. 81 No. 7.

Kim et al.; "Fabrication and analysis of plastic hypodermic needles"; Journal of Medical Engineering & Technology; Jul./Aug. 2005; pp. 181-186; vol. 29 No. 4; Taylor & Francis Group Ltd.

Lim et al.; "A Micromechanical Biosensor with Interdigitated Capacitor Readout"; International Conference on Complex Medical Engineering; May 22-25, 2011; pp. 42-46; IEEE.

"Micro Linear Actuators with Built-in Controllers"; Zaber.com; printed on Apr. 24, 2014; pp. 1-2.

Ohno et al; "Graphene Field-Effect Transistors for Label-Free Biological Sensors"; IEEE Sensors 2010 conference; printed on Jun. 30, 2014; pp. 903-906; IEEE.

Park et al.; "Profile of Xeomin® (incobotulinumtoxinA) for the treatment of blepharospasm"; Clinical Ophthalmology; printed on Jun. 30, 2014; pp. 725-732; vol. 5; Dove Medical Press Ltd.

Tehrani et al.; "Detection of Monoclonal Antibodies using Chemically Modified Graphite Substrates"; IEEE Sensors 2010 Conference; printed on Jun. 30, 2014; pp. 428-431; vol. 10; IEEE.

Xie et al.; "Modelling and Simulation for Micro Injection Molding Process"; Computational Fluid Dynamics Technologies and Applications; bearing a date of Jul. 5, 2011; InTech.

* cited by examiner

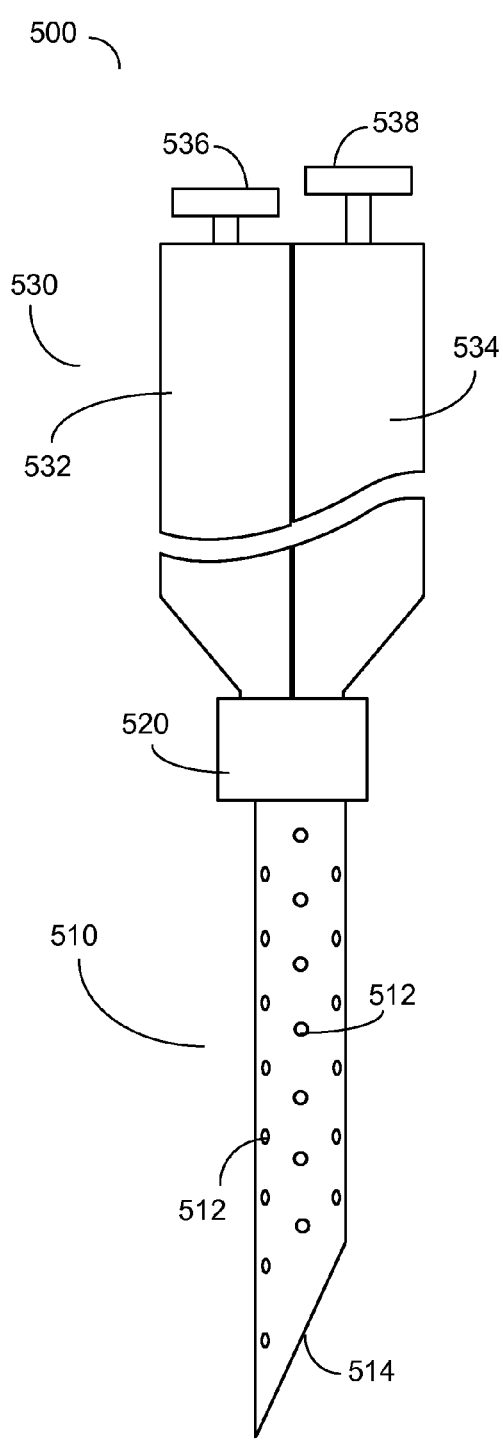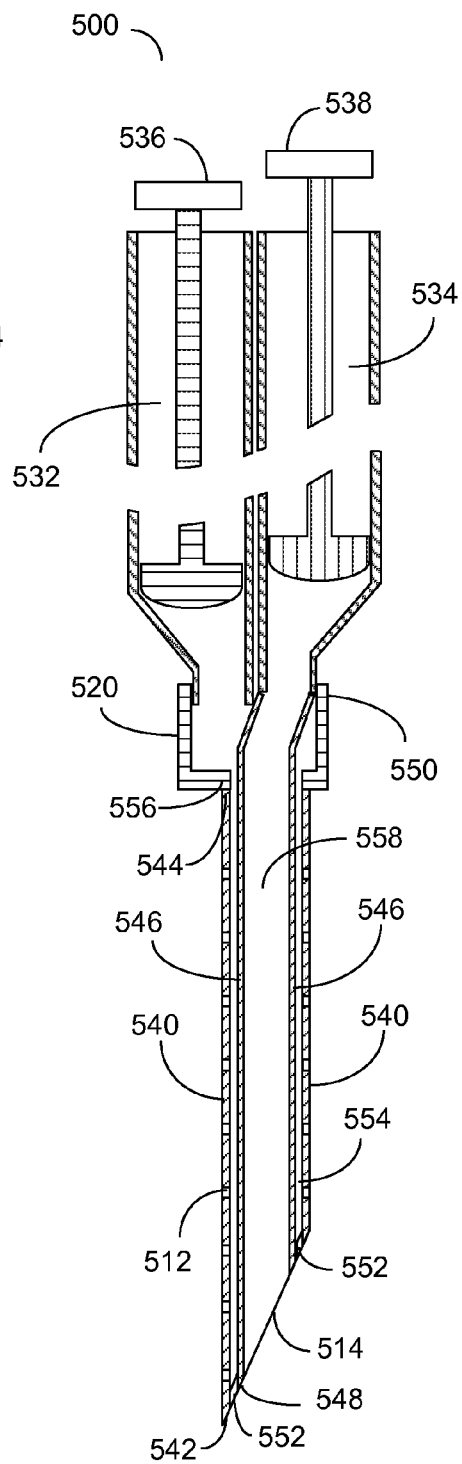
FIG. 5A
FIG. 5B

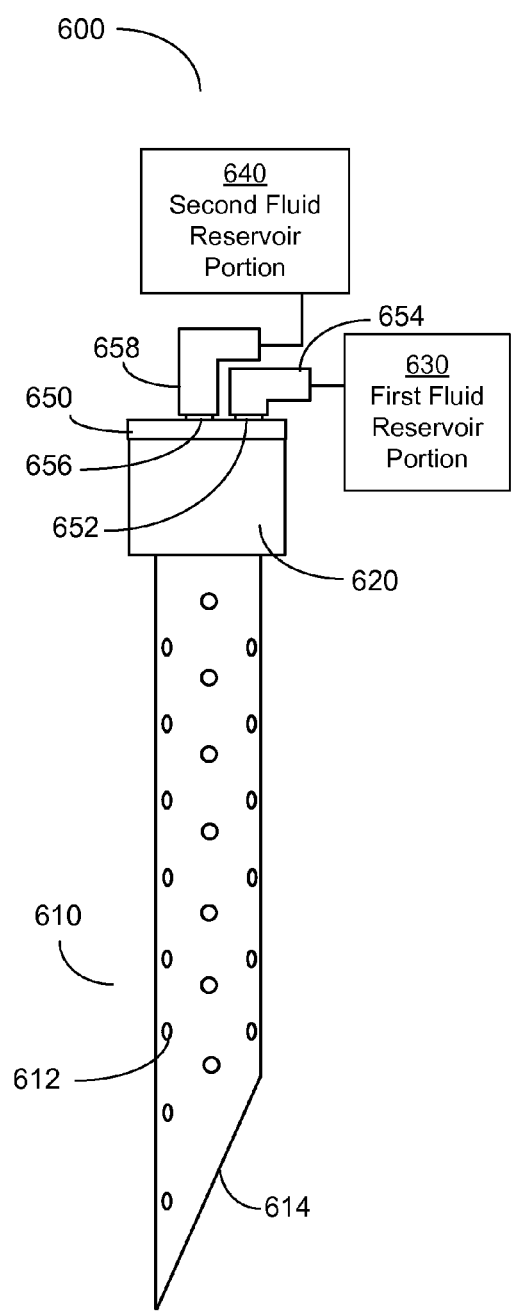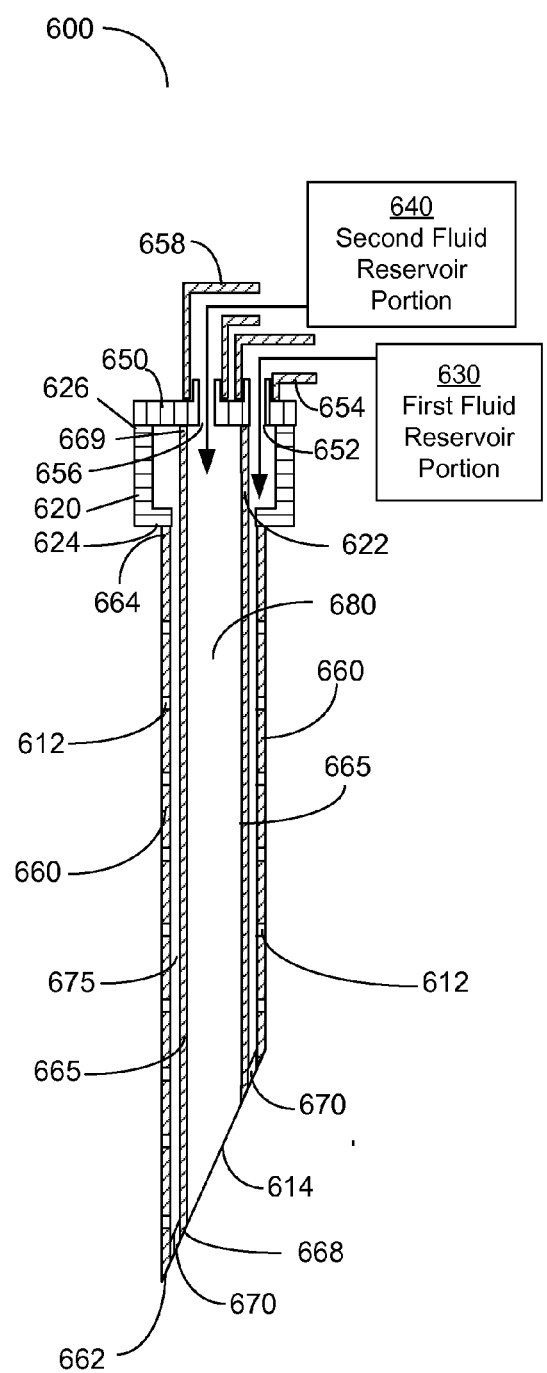

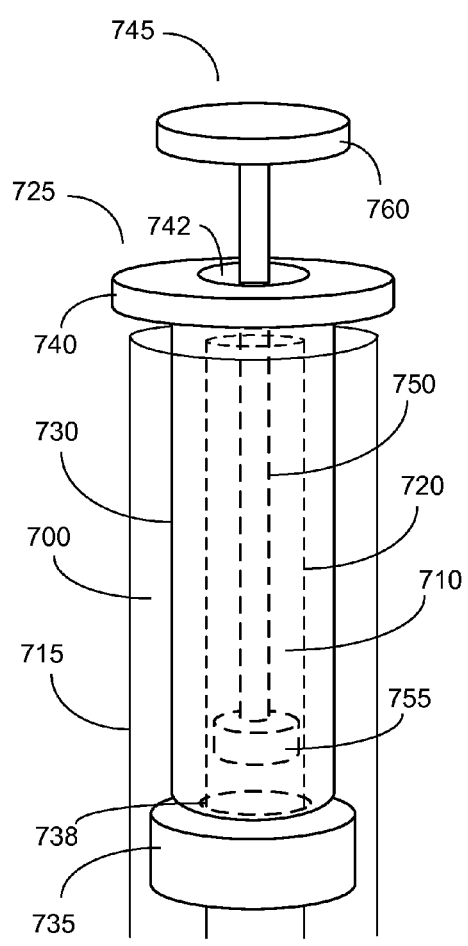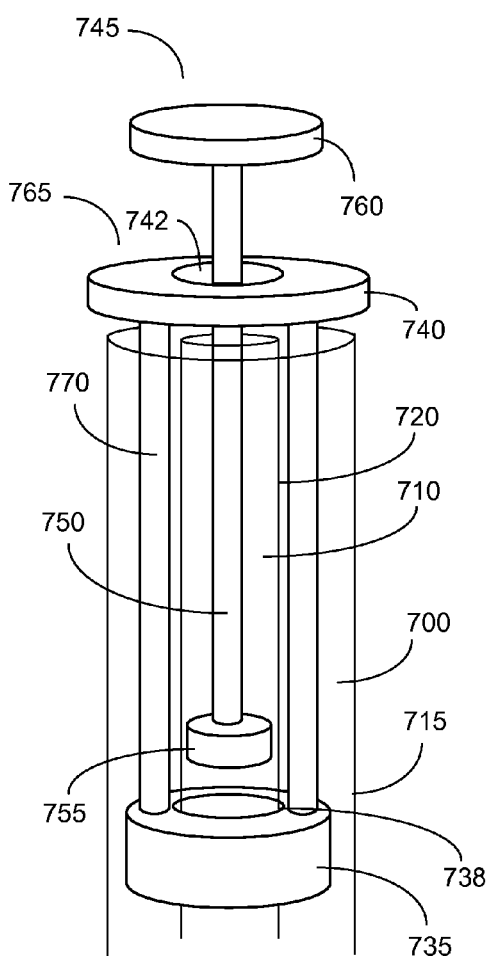

FIG. 14A
FIG. 14B
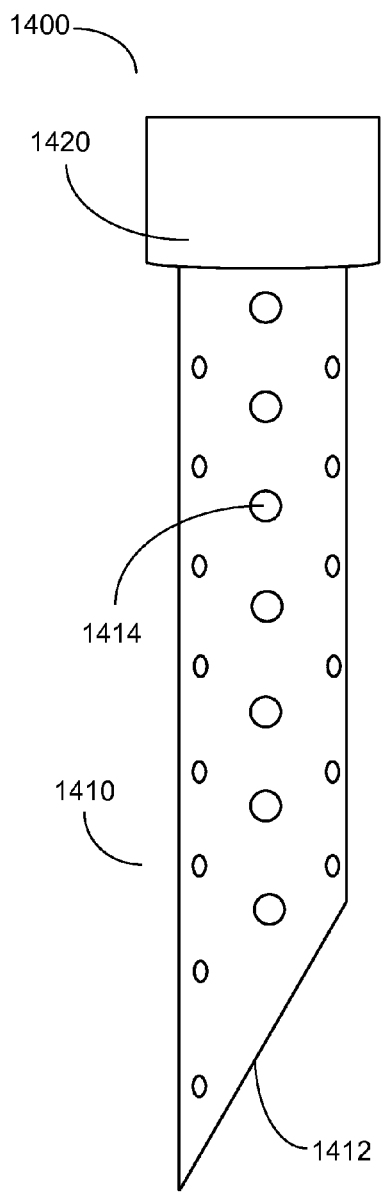
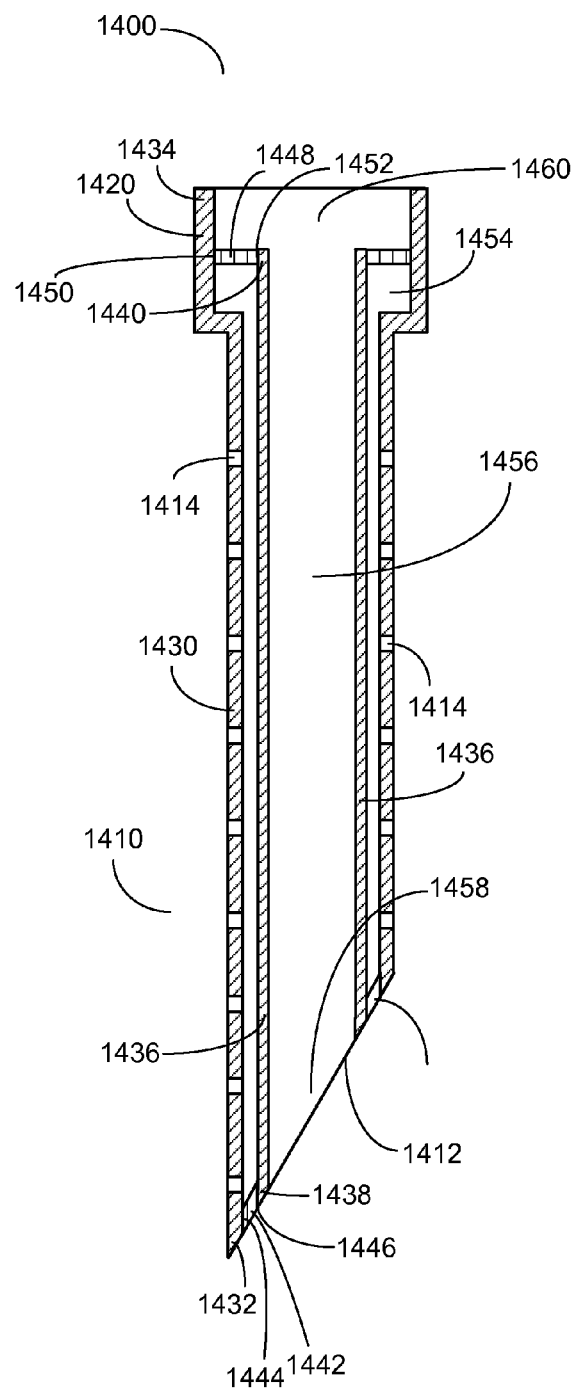

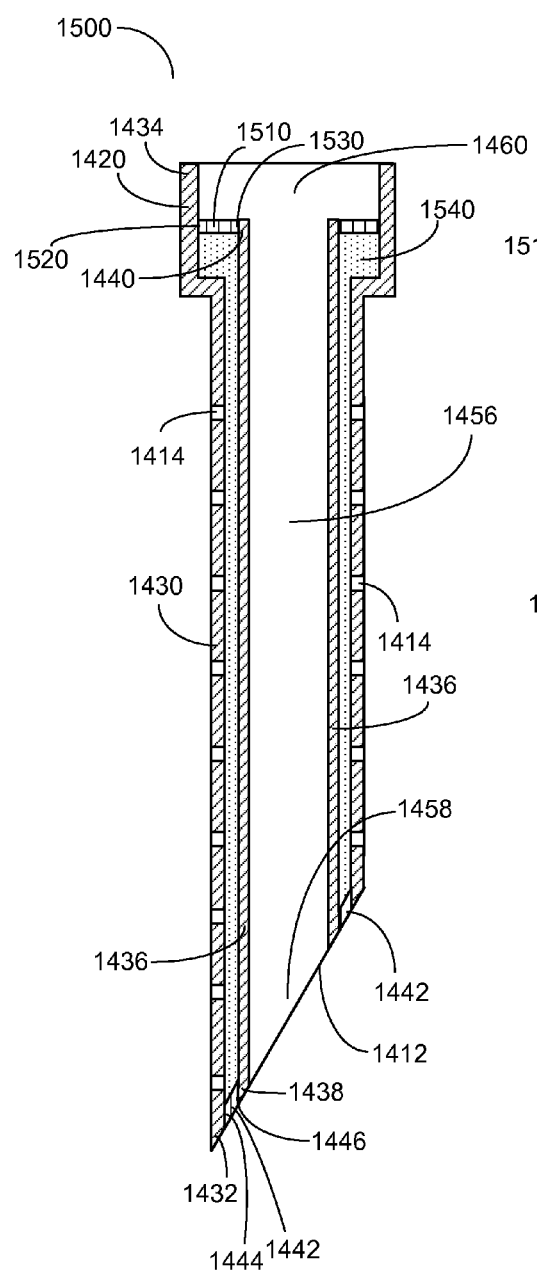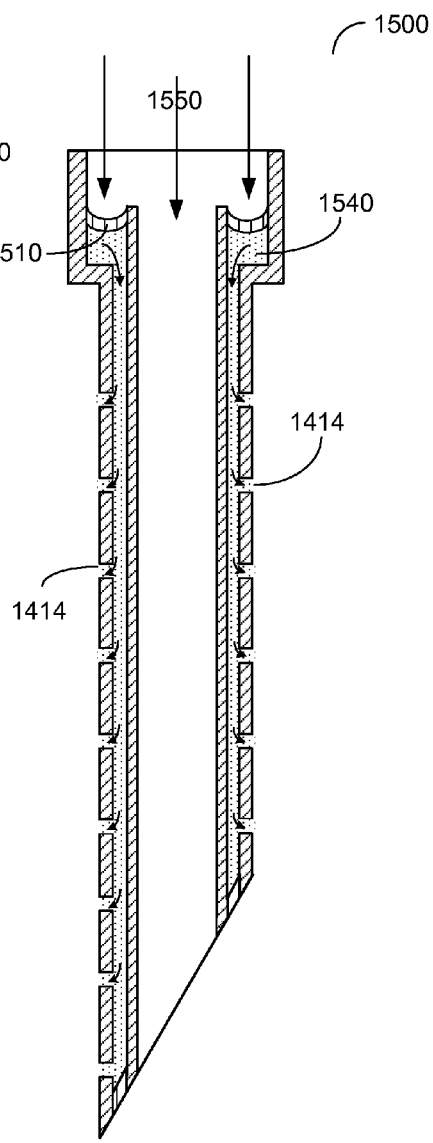

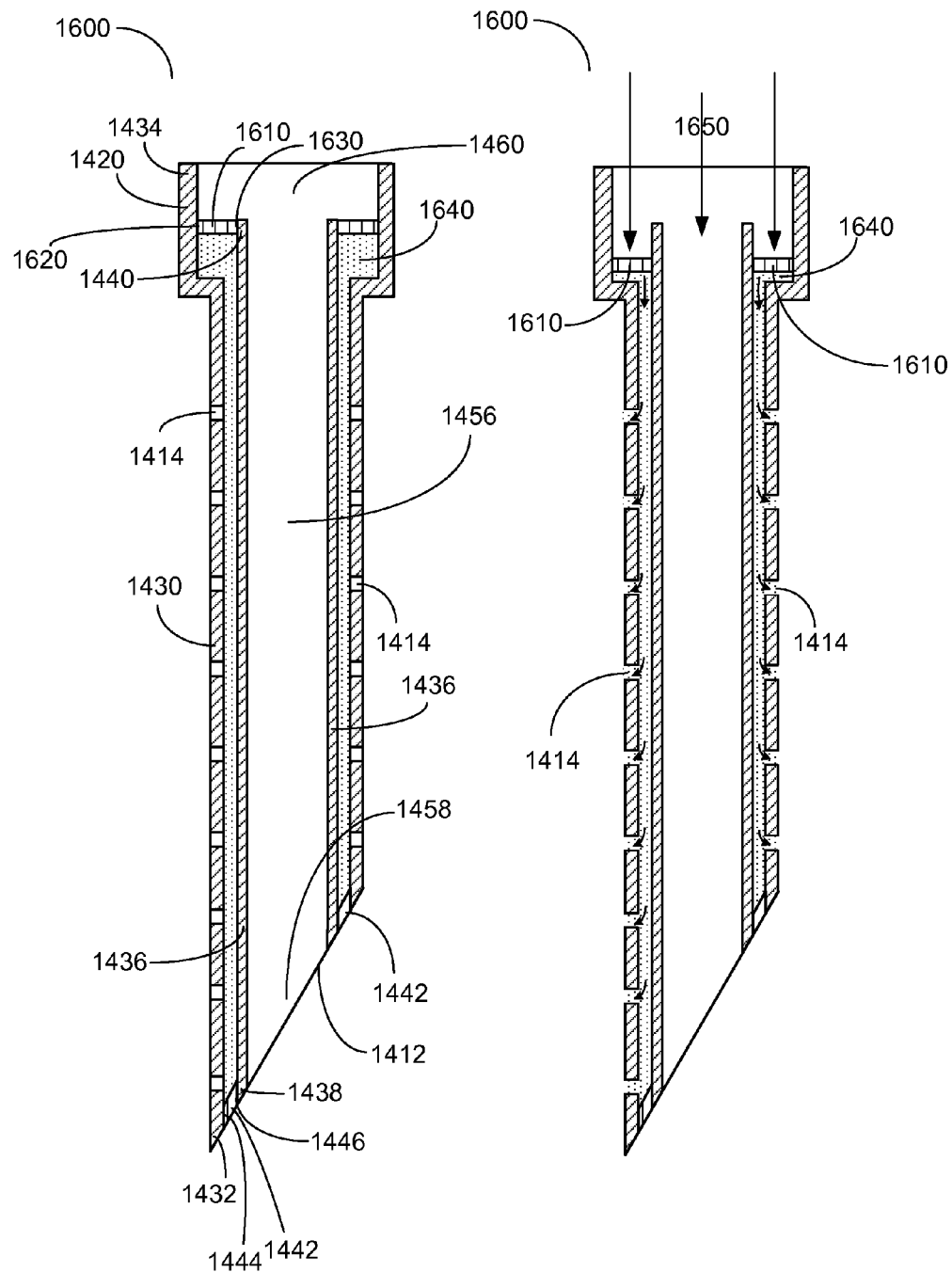

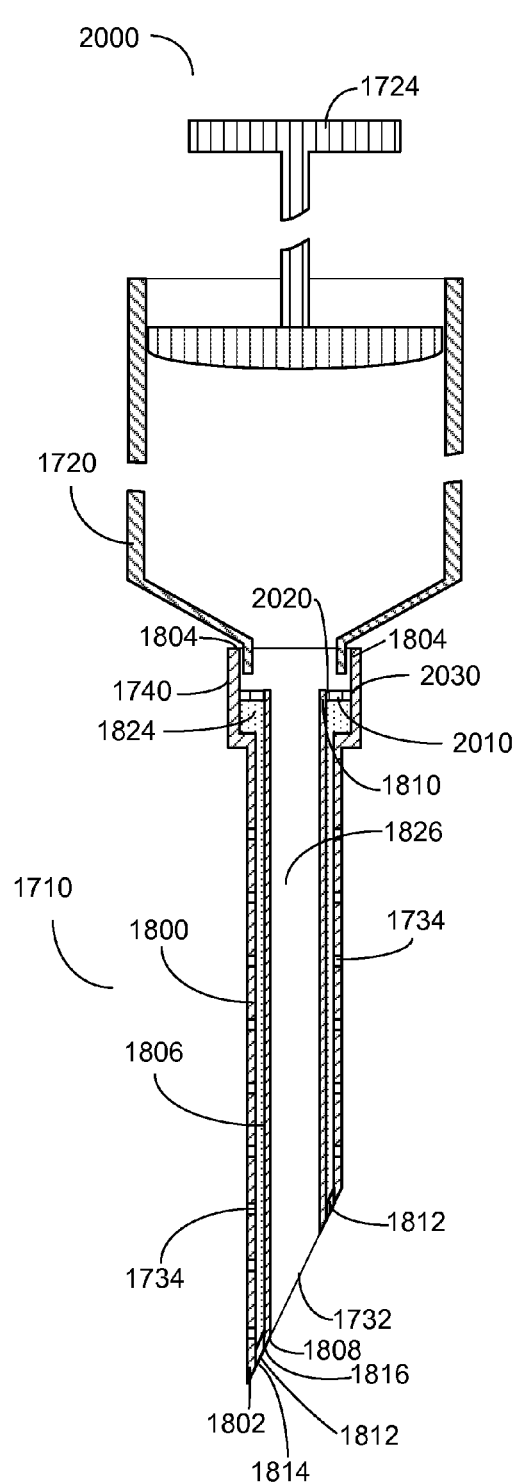
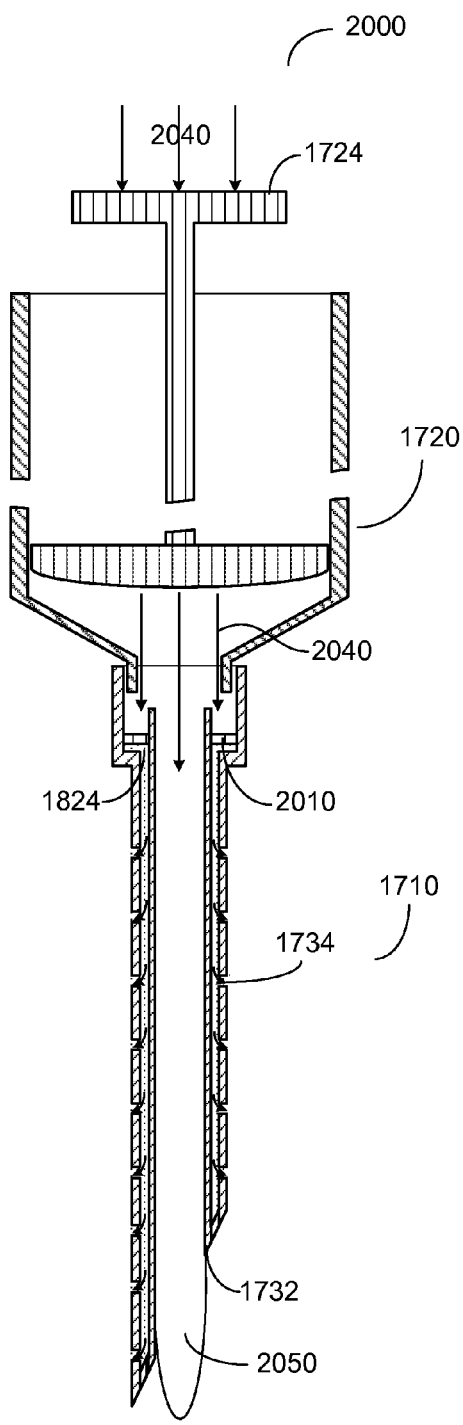
FIG. 20A
FIG. 20B

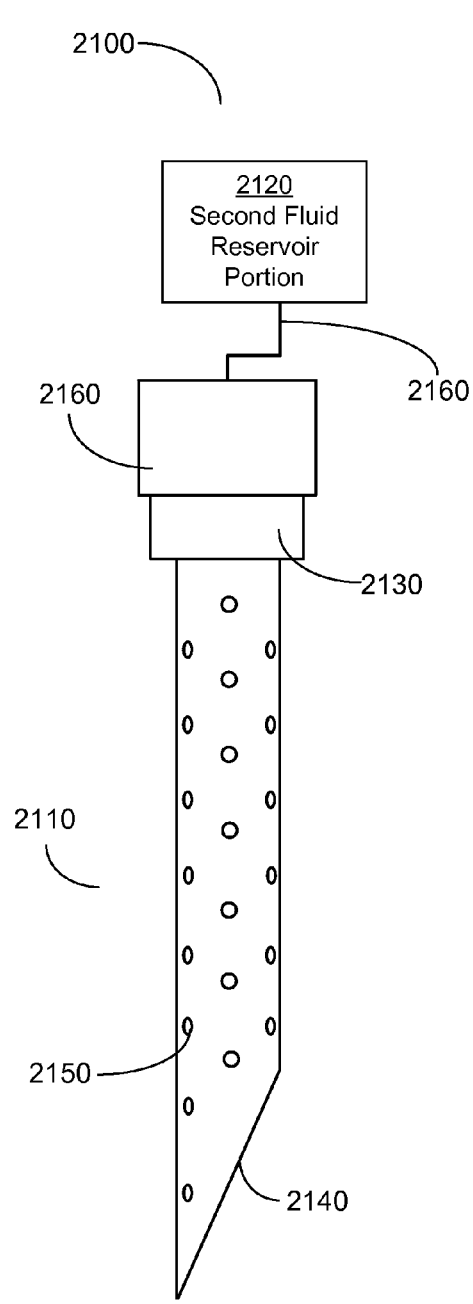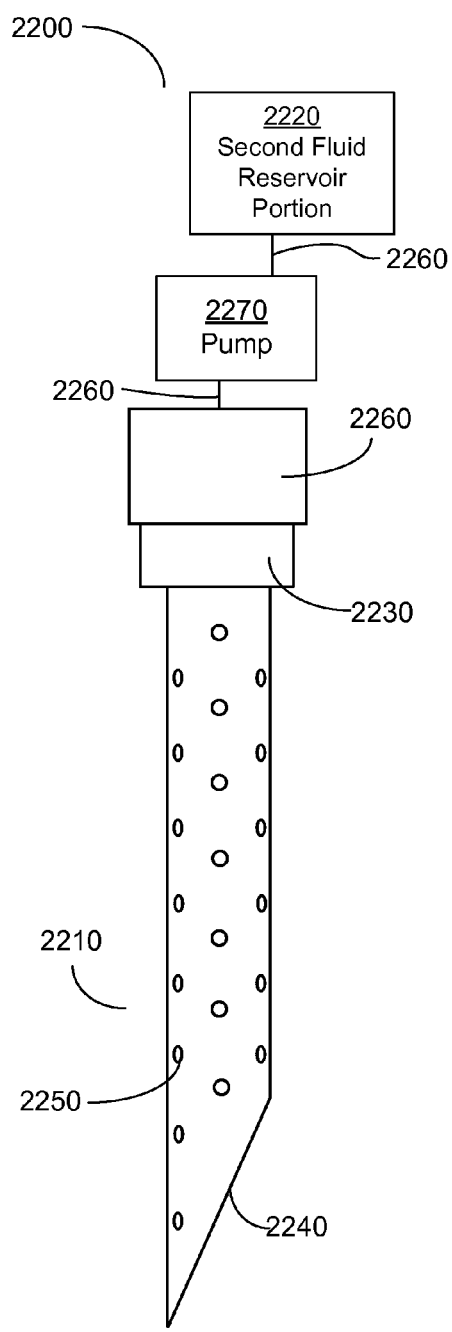

FIG. 25A
FIG. 25B
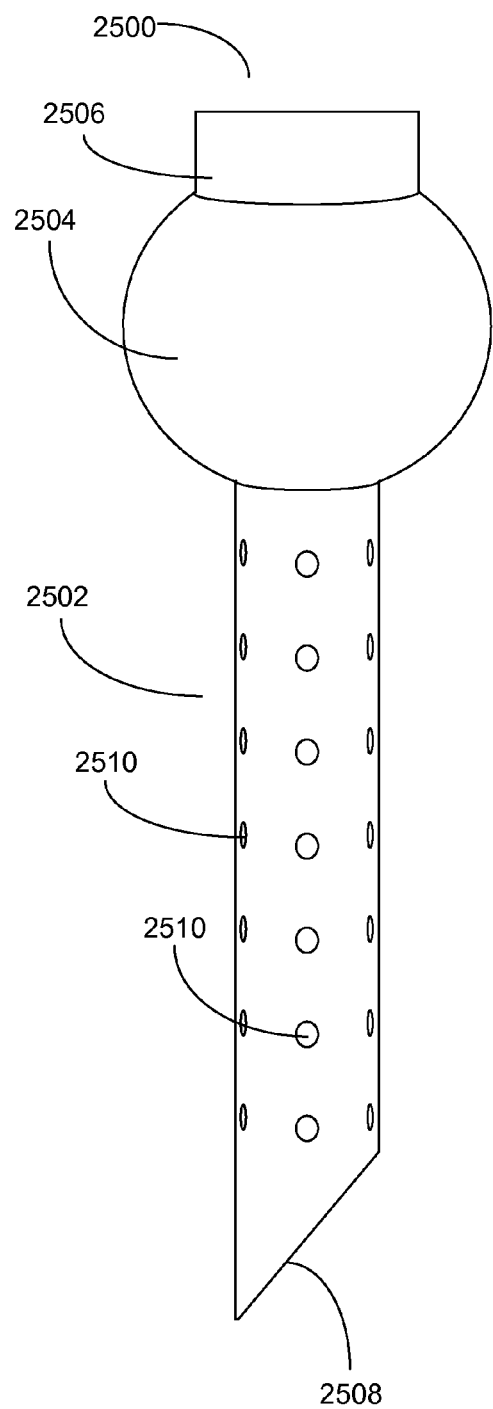
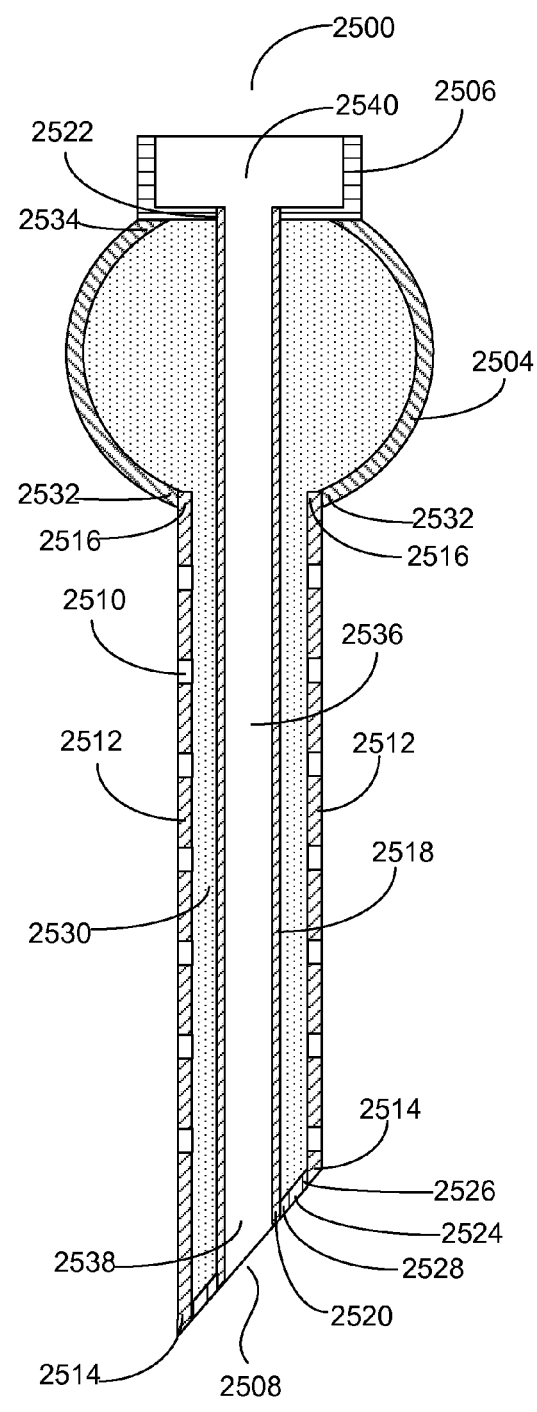

FIG. 26A
FIG. 26B
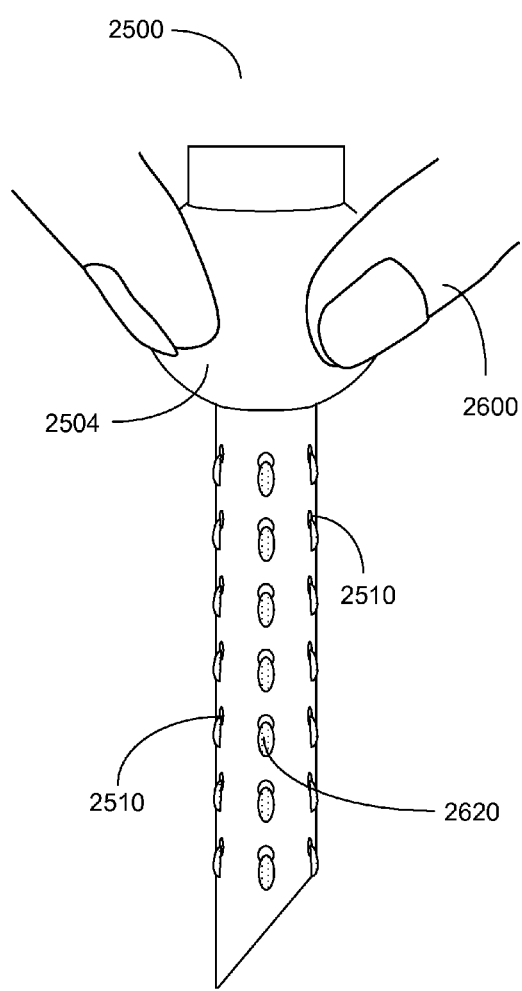
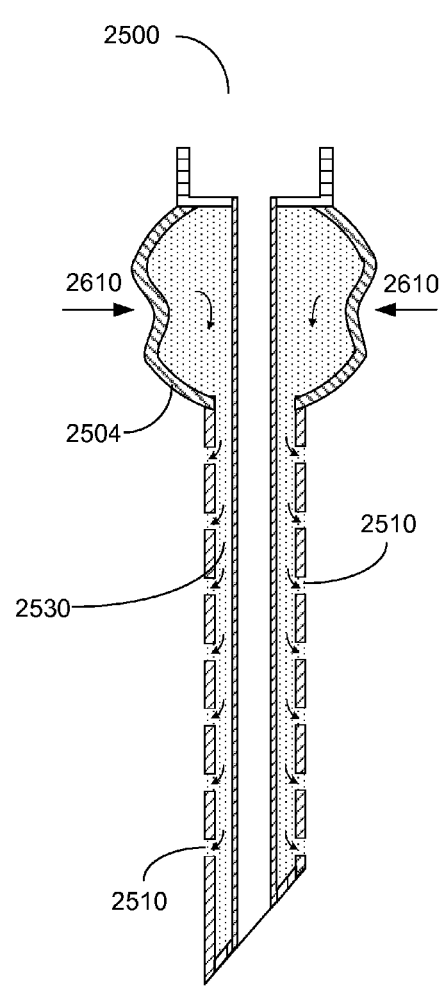

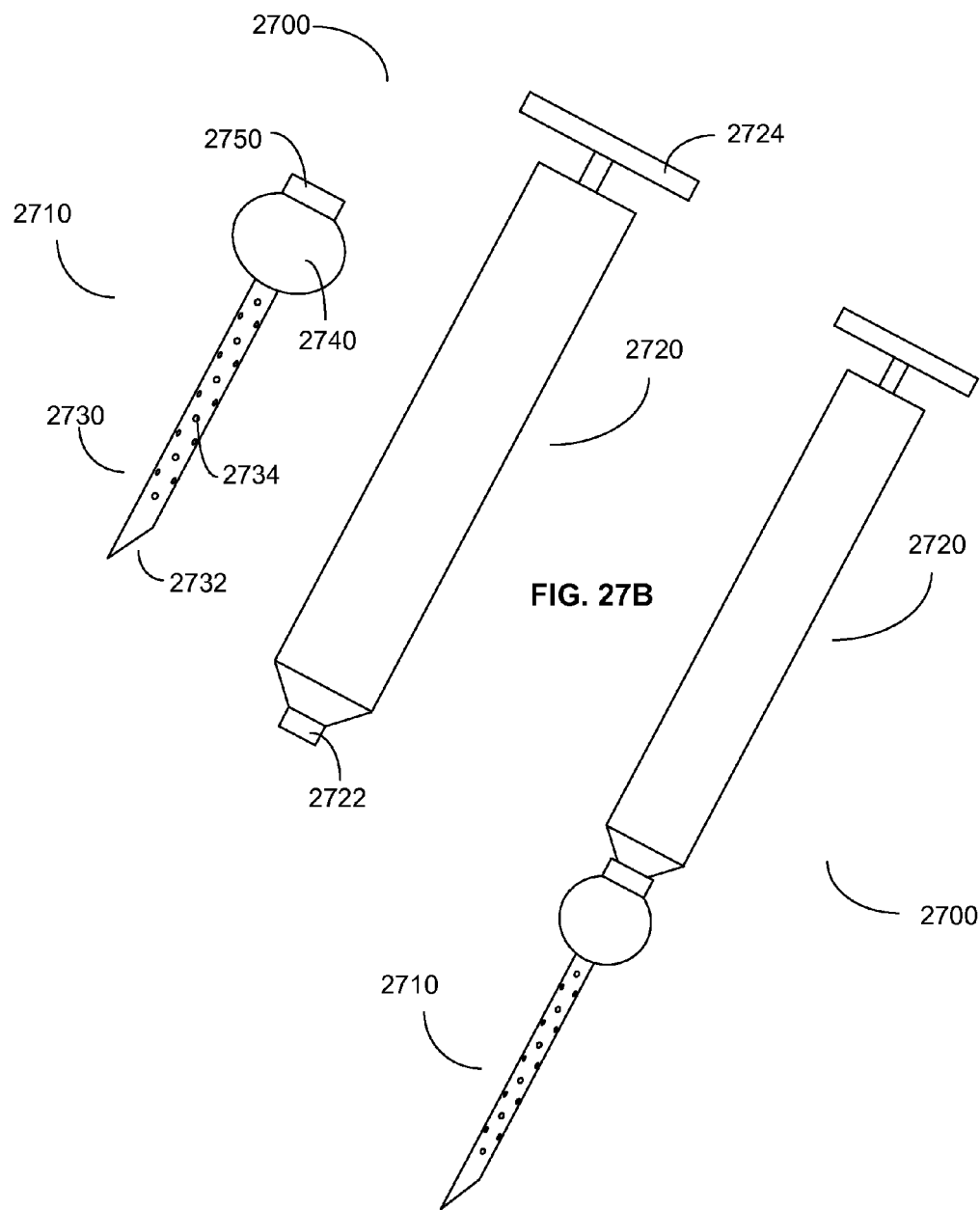

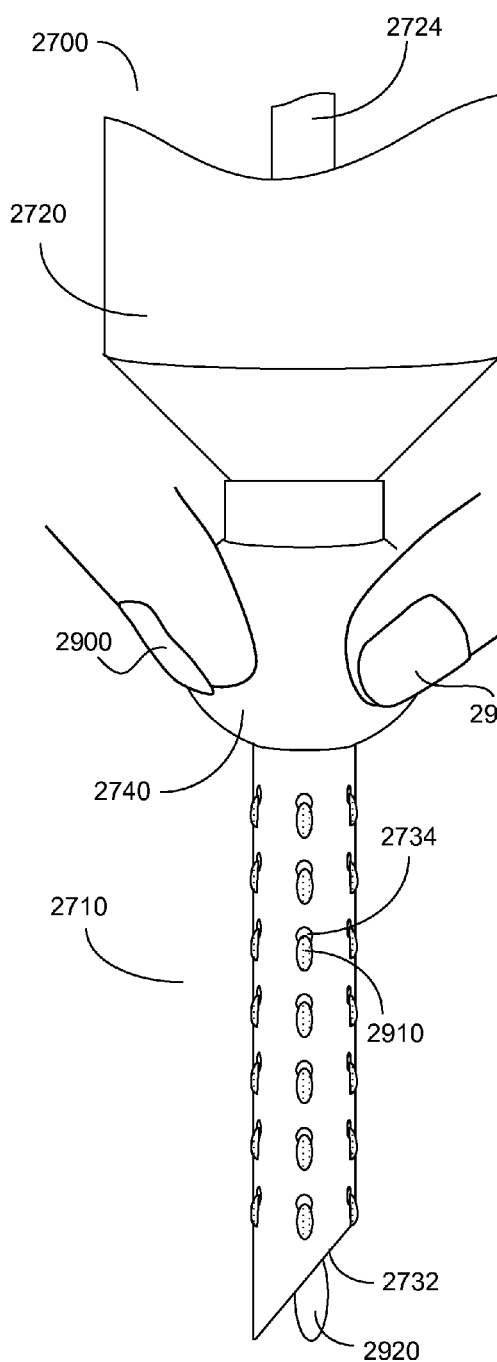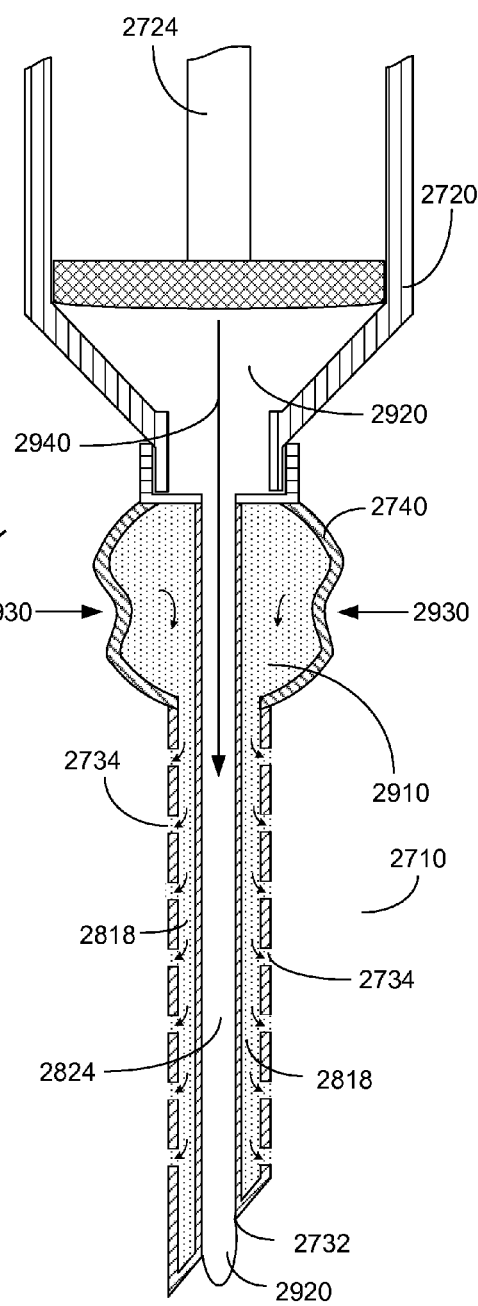

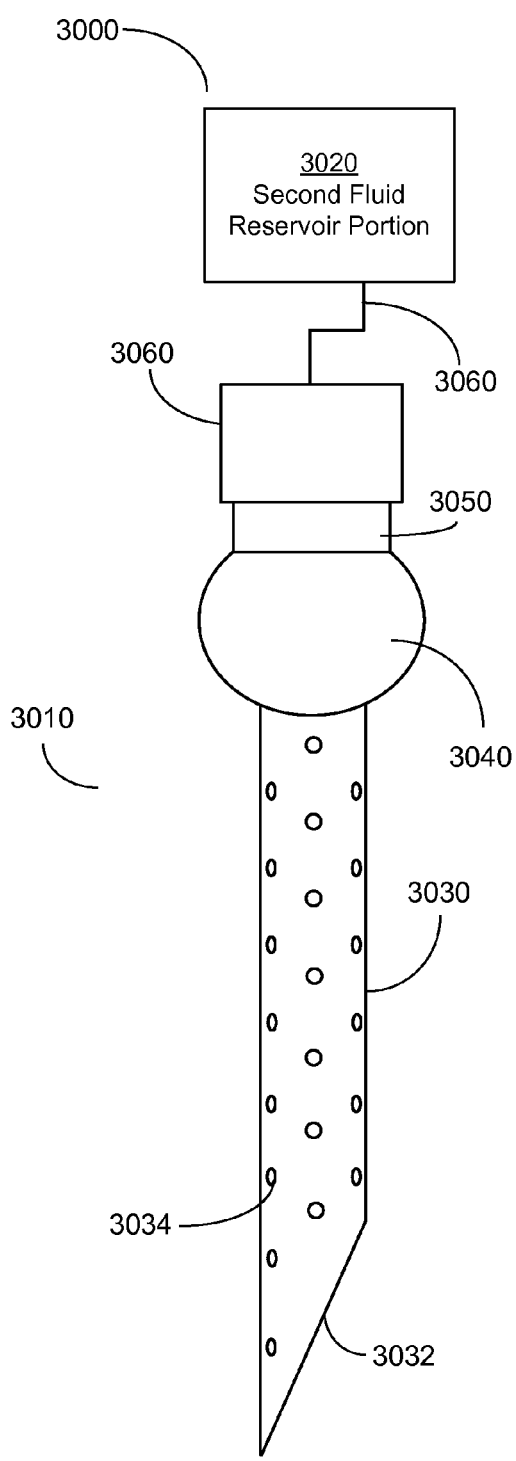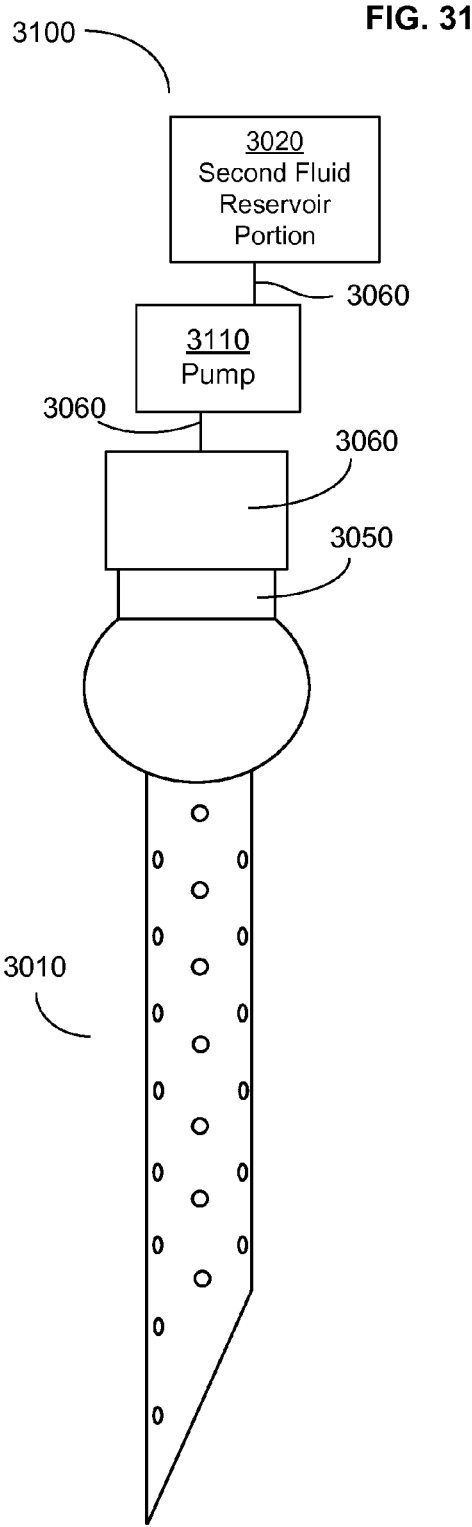
FIG. 30
FIG. 31

ACTIVE LUBRICATION OF PENETRATING DEVICES

If an Application Data Sheet (ADS) has been filed on the filing date of this application, it is incorporated by reference herein. Any applications claimed on the ADS for priority under 35 U.S.C. § § 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

PRIORITY APPLICATIONS

None

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a penetrating device includes, but is not limited to, a first hollow cylinder having a first end and a second end, the first hollow cylinder including a plurality of pores; a second hollow cylinder having a first end and a second end, the second hollow cylinder disposed within the first hollow cylinder and substantially coaxial to the first hollow cylinder; a substantially ring-shaped end piece have an outer edge and an inner edge, the outer edge of the substantially ring-shaped end piece secured to the first end of the first hollow cylinder and the inner edge of the of the substantially ring-shaped end piece secured to the first end of the second hollow cylinder, wherein the first hollow cylinder, the second hollow cylinder, and the substantially ring-shaped end piece form a penetrating edge; an internal fluid conduit defined by a space between the first hollow cylinder and the substantially coaxial second hollow cylinder, the internal fluid conduit in fluid communication with the plurality of pores along the length of the first hollow cylinder; a connector portion with a first end and a second end, the connector portion disposed over and coaxial to a region of the second hollow cylinder proximal to the second end of the second hollow cylinder, the first end of the connector portion attached proximal to the second end of the first hollow cylinder, the connector portion in fluid communication with the internal fluid conduit; a lumen defined by the second hollow cylinder, the lumen having a first end and a second end, the first end of the lumen in fluid communication with the penetrating edge; a first fluid reservoir portion for holding a first fluid composition, the first fluid reservoir portion associated with the second end of the connector portion, the first fluid reservoir portion in fluid communication with the connector portion and the internal fluid conduit; a second fluid reservoir portion, the second fluid reservoir portion associated with the second end of the second hollow cylinder, the second fluid reservoir portion in fluid communication with the lumen defined by the second hollow cylinder; a first initiator configured to induce flow of the first fluid composition from the first fluid reservoir portion, through the internal fluid conduit, and out at least one of the plurality of pores; and a second initiator configured to induce flow into or out of the second fluid reservoir portion, through the lumen defined by the second hollow cylinder. In addition to the foregoing, other device aspects are described in the claims, drawings, and text forming a part of the present disclosure.

In an aspect, a penetrating system includes, but is not limited to, a penetrating device and a computing device, the penetrating device including a first hollow cylinder having a first end and a second end, the first hollow cylinder including a plurality of pores; a second hollow cylinder having a first end and a second end, the second hollow cylinder disposed within the first hollow cylinder and substantially coaxial to the first hollow cylinder; a substantially ring-shaped end piece have an outer edge and an inner edge, the outer edge of the substantially ring-shaped end piece secured to the first end of the first hollow cylinder and the inner edge of the of the substantially ring-shaped end piece secured to the first end of the second hollow cylinder, wherein the first hollow cylinder, the second hollow cylinder, and the substantially ring-shaped end piece form a penetrating edge; an internal fluid conduit defined by a space between the first hollow cylinder and the substantially coaxial second hollow cylinder, the internal fluid conduit in fluid communication with the plurality of pores along the length of the first hollow cylinder; a connector portion with a first end and a second end, the connector portion disposed over and coaxial to a region of the second hollow cylinder proximal to the second end of the second hollow cylinder, the first end of the connector portion attached proximal to the second end of the first hollow cylinder, the connector portion in fluid communication with the internal fluid conduit; a lumen defined by the second hollow cylinder, the lumen having a first end and a second end, the first end of the lumen in fluid communication with the penetrating edge; a first fluid reservoir portion for holding a first fluid composition, the first fluid reservoir portion associated with the second end of the connector portion, the first fluid reservoir portion in fluid communication with the connector portion and the internal fluid conduit; a second fluid reservoir portion, the second fluid reservoir portion associated with the second end of the second hollow cylinder, the second fluid reservoir portion in fluid communication with the lumen defined by the second hollow cylinder; a first initiator configured to induce flow of the first fluid composition from the first fluid reservoir portion, through the internal fluid conduit, and out at least one of the plurality of pores; and a second initiator configured to induce flow into or out of the second fluid reservoir portion, through the lumen defined by the second hollow cylinder; and a computing device including a processor and operably coupled to the penetrating device, the computing device including circuitry configured to controllably actuate at least one of the first initiator to the second initiator. In addition to the foregoing, other system aspects are described in the claims, drawings, and text forming a part of the present disclosure.

In an aspect, a penetrating device includes, but is not limited to a first hollow cylinder having a first end and a second end, the first hollow cylinder including a plurality of pores, the second end of the first hollow cylinder having a connector portion; a second hollow cylinder having a first end and a second end, the second hollow cylinder disposed within the first hollow cylinder and substantially coaxial to the first hollow cylinder; a substantially ring-shaped first end piece having an outer edge and an inner edge, the outer edge of the substantially ring-shaped first end piece secured to the first end of the first hollow cylinder and the inner edge of the substantially ring-shaped first end piece secured to the first end of the second hollow cylinder, wherein the first hollow cylinder, the second hollow cylinder, and the substantially ring-shaped first end piece form a penetrating edge; a substantially ring-shaped second end piece having an outer edge and an inner edge, the outer edge of the substantially ring-shaped second end piece adjacent to a portion of the first hollow cylinder proximal to the second end of the first hollow cylinder and the inner edge of the substantially ring-shaped second end piece adjacent to a portion of the second hollow cylinder proximal to the second end of the second hollow cylinder, the substantially ring-shaped second end piece forming a deformable barrier; a fluid reservoir portion for holding a fluid composition, the fluid reservoir portion defined by the first hollow cylinder, the second hollow cylinder, the substantially ring-shaped first end piece, and the substantially ring-shaped second end piece, the fluid reservoir portion in fluid communication with the plurality of pores; and a lumen defined by the second hollow cylinder, the lumen having a first end and a second end, the first end of the lumen in fluid communication with the penetrating edge. In addition to the foregoing, other aspects of a device are described in the claims, drawings, and text forming a part of the present disclosure.

In an aspect, a penetrating system includes, but is not limited to, a penetrating device including a first hollow cylinder having a first end and a second end, the first hollow cylinder including a plurality of pores, the second end of the first hollow cylinder having a connector portion; a second hollow cylinder having a first end and a second end, the second hollow cylinder disposed within the first hollow cylinder and substantially coaxial to the first hollow cylinder; a substantially ring-shaped first end piece having an outer edge and an inner edge, the outer edge of the substantially ring-shaped first end piece secured to the first end of the first hollow cylinder and the inner edge of the substantially ring-shaped first end piece secured to the first end of the second hollow cylinder, wherein the first hollow cylinder, the second hollow cylinder, and the substantially ring-shaped first end piece form a penetrating edge; a substantially ring-shaped second end piece having an outer edge and an inner edge, the outer edge of the substantially ring-shaped second end piece adjacent to a portion of the first hollow cylinder proximal to the second end of the first hollow cylinder and the inner edge of the substantially ring-shaped second end piece adjacent to a portion of the second hollow cylinder proximal to the second end of the second hollow cylinder, the substantially ring-shaped second end piece forming a deformable barrier; a first fluid reservoir portion for holding a first fluid composition, the first fluid reservoir portion defined by the first hollow cylinder, the second hollow cylinder, the substantially ring-shaped first end piece, and the substantially ring-shaped second end piece, the first fluid reservoir portion in fluid communication with the plurality of pores; and a lumen defined by the second hollow cylinder, the lumen having a first end and a second end, the first end of the lumen in fluid communication with the penetrating edge; and a second fluid reservoir portion for holding a second fluid composition, the second fluid reservoir portion including an initiator, the second fluid reservoir portion attached to the penetrating device through the connector portion of the first hollow cylinder, the second fluid reservoir portion in fluid communication with the second end of the lumen defined by the second hollow cylinder. In addition to the foregoing, other aspects of a system are described in the claims, drawings, and text forming a part of the present disclosure.

In an aspect, a penetrating device includes, but is not limited to, a first hollow cylinder having a first end and a second end, the first hollow cylinder including a plurality of pores; a second hollow cylinder having a first end and a second end, the second hollow cylinder disposed within the first hollow cylinder and substantially coaxial to the first hollow cylinder, the second end of the second hollow cylinder having a connector portion; a substantially ring-shaped end piece having an outer edge and an inner edge, the outer edge of the substantially ring-shaped end piece secured to the first end of the first hollow cylinder and the inner edge of the substantially ring-shaped end piece secured to the first end of the second hollow cylinder, wherein the first hollow cylinder, the second hollow cylinder, and the substantially ring-shaped end piece form a penetrating edge; an internal fluid conduit defined by a space between the first hollow cylinder and the substantially coaxial second hollow cylinder, the internal fluid conduit in fluid communication with the plurality of pores along the length of the first hollow cylinder; a fluid reservoir portion for holding a fluid composition, the fluid reservoir portion including a hollow structure with a first end and a second end, the hollow structure disposed over and substantially coaxial to a region of the second hollow cylinder proximal to the second end of the second hollow cylinder, the first end of the hollow structure secured to the second end of the first hollow cylinder and the second end of the hollow structure secured proximal to the second end of the second hollow cylinder, the hollow structure in fluid communication with the internal fluid conduit; and a lumen defined by the second hollow cylinder, the lumen having a first end and a second end, the first end of the lumen in fluid communication with the penetrating edge. In addition to the foregoing, other aspects of a device are described in the claims, drawings, and text forming a part of the present disclosure.

In an aspect, a penetrating system includes, but is not limited to, a penetrating device including a first hollow cylinder having a first end and a second end, the first hollow cylinder including a plurality of pores; a second hollow cylinder having a first end and a second end, the second hollow cylinder disposed within the first hollow cylinder and substantially coaxial to the first hollow cylinder, the second end of the second hollow cylinder having a connector portion; a substantially ring-shaped end piece having an outer edge and an inner edge, the outer edge of the substantially ring-shaped end piece secured to the first end of the first hollow cylinder and the inner edge of the substantially ring-shaped end piece secured to the first end of the second hollow cylinder, wherein the first hollow cylinder, the second hollow cylinder, and the substantially ring-shaped end piece form a penetrating edge; an internal fluid conduit defined by a space between the first hollow cylinder and the substantially coaxial second hollow cylinder, the internal fluid conduit in fluid communication with the plurality of pores along the length of the first hollow cylinder; a first fluid reservoir portion for holding a first fluid composition, the first fluid reservoir portion including a hollow structure with a first end and a second end, the hollow structure disposed over and substantially coaxial to a region of the second hollow cylinder proximal to the second end of the second hollow cylinder, the first end of the hollow structure secured to the second end of the first hollow cylinder and the second end of the hollow structure secured proximal to the second end of the second hollow cylinder, the hollow structure in fluid communication with the internal fluid conduit; and a lumen defined by the second hollow cylinder, the lumen having a first end and a second end, the first end of the lumen in fluid communication with the penetrating edge; and a second fluid reservoir portion including an initiator, the second fluid reservoir portion attached to the penetrating device through the connector portion of the second hollow cylinder, the second fluid reservoir portion in fluid communication with the second end of the lumen defined by the second hollow cylinder. In addition to the foregoing, other aspects of a system are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 5A shows a schematic of an external view of a penetrating device with parallel fluid reservoirs.
FIG. 5B shows a schematic of a longitudinal cross-section through a penetrating device with parallel fluid reservoirs.
FIG. 6A shows a schematic of an external view of a penetrating device connected to a first and second fluid reservoir portion through a flow conduit.
FIG. 6B shows a schematic of a longitudinal cross-section through a penetrating device connected to a first and second fluid reservoir portion through a flow conduit.
FIG. 7A shows a schematic of an initiator of a penetrating device.
FIG. 7B shows a schematic of an initiator of a penetrating device.
FIG. 14A shows a schematic of an external view a penetrating device.
FIG. 14B shows a schematic of a longitudinal cross-section through a penetrating device.
FIG. 15A shows a schematic of a longitudinal cross-section through a penetrating device including a deformable substantially ring-shaped second end piece.
FIG. 15B shows a schematic of a longitudinal cross-section through a penetrating device including a deformable substantially ring-shaped second end piece.
FIG. 16A shows a schematic of a longitudinal cross-section through a penetrating device including a moveable substantially ring-shaped second end piece.
FIG. 16B shows a schematic of a longitudinal cross-section through a penetrating device including a moveable substantially ring-shaped second end piece.
FIG. 20A shows a schematic of a longitudinal cross-section through a penetrating system including a moveable substantially ring-shaped second end piece.
FIG. 20B shows a schematic of a longitudinal cross-section through a penetrating system including a moveable substantially ring-shaped second end piece.
FIG. 21 shows a schematic of a penetrating system including a second fluid reservoir portion attached to a penetrating device through a flow conduit.
FIG. 22 shows a schematic of a penetrating system including a second fluid reservoir portion and a pump attached a penetrating device through a flow conduit.
FIG. 25A shows a schematic of an external view of a penetrating device.
FIG. 25B shows a schematic of a longitudinal cross-section through a penetrating device.
FIG. 26A shows a schematic of an external view of a penetrating device and a flow pattern of a fluid composition in response to an applied pressure.
FIG. 26B shows a schematic of a longitudinal cross-section through a penetrating device and a flow pattern of a fluid composition in response to an applied pressure.
FIG. 27A shows a schematic of a penetrating system.
FIG. 27B shows a schematic of a penetrating system.

FIG. 29A shows a schematic of an external view of a penetrating system and a flow pattern of a fluid composition in response to an applied pressure.

FIG. 29B shows a schematic of a longitudinal cross-section through a penetrating system and a flow pattern of a fluid composition in response to an applied pressure.

FIG. 30 shows a schematic of a penetrating system including a second fluid reservoir portion attached to a penetrating device through a flow conduit.

FIG. 31 shows a schematic of a penetrating system including a second fluid reservoir portion and a pump attached to a penetrating device through a flow conduit.

DETAILED DESCRIPTION

Figure 1:
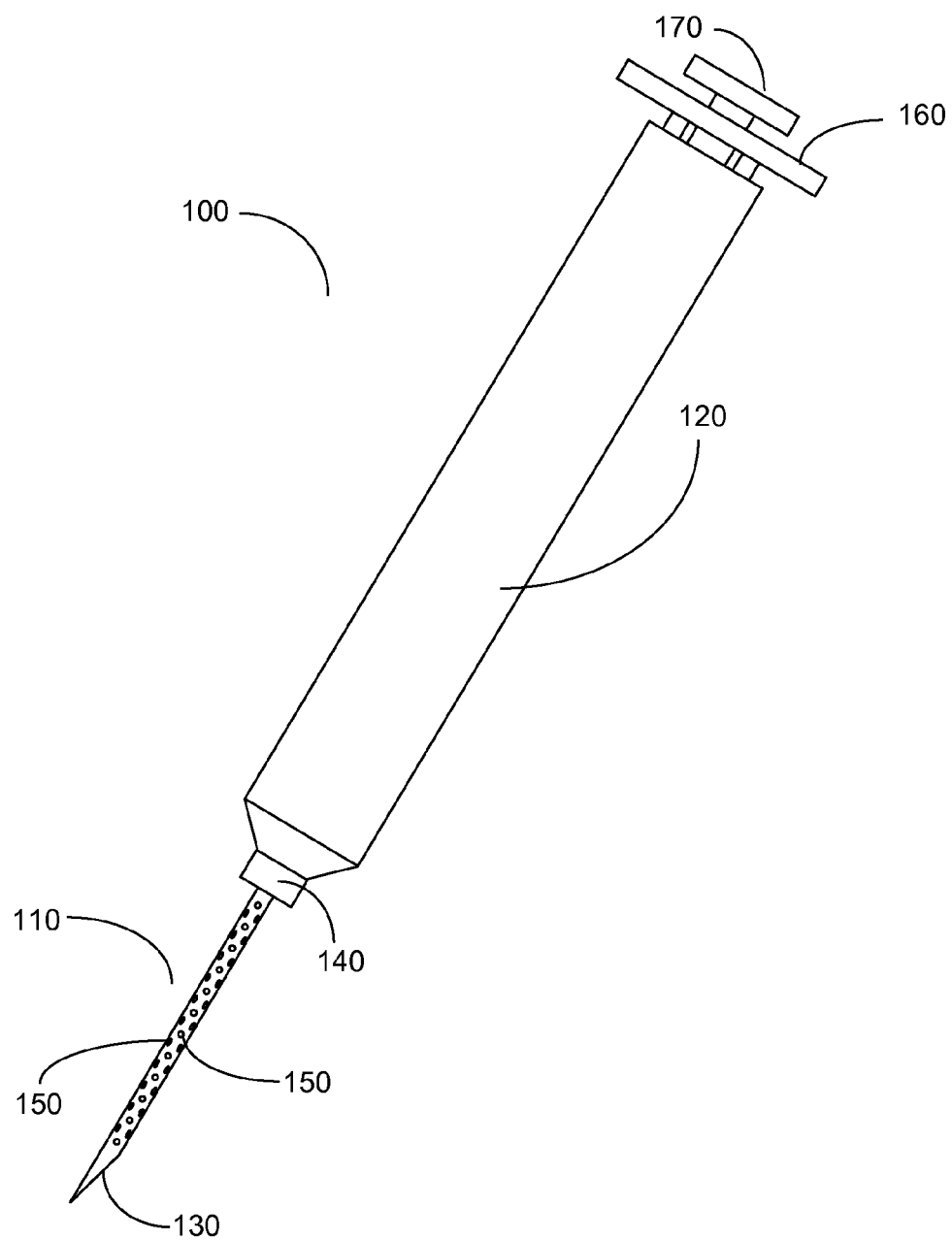
FIG. 1 shows a schematic of a penetrating device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In general, penetration of a medium by a penetrating device, e.g., a needle, must overcome friction, which can damage the medium or the device and cause an increase in time spent during penetration. In particular, mammalian tissue penetration by a penetrating device, e.g., a hypodermic needle, can induce pain during the injection process, both from the initial piercing of the tissue and the sliding friction of the needle surface against the tissue. See, e.g., Gill & Prausnitz (2007) *J. Diabetes Sci. Technol.* 1:725-729, which is incorporated herein by reference. In addition, the tissue injection process is associated with an increased risk of infection at the injection site. See, e.g., Hutin et al. (2003) *Bulletin of the World Health Organization* 81(7), which is incorporated herein by reference. Described herein are penetrating systems and devices, the systems and devices including a plurality of pores distributed along the length of a penetrating portion of the systems and devices, the plurality of pores in fluid communication with a fluid reservoir, the fluid reservoir configured to hold a fluid composition, wherein the fluid composition flows laterally out of the plurality of pores to aide in the injection process.

With reference to FIG. 1, shown is an example of a penetrating device. Penetrating device 100 includes penetrating portion 110 and a reservoir portion 120. Penetrating portion 110 includes penetrating edge 130, connector portion 140, and a plurality of pores 150. Reservoir portion 120 is attached to penetrating portion 110 through connector portion 140. Reservoir portion 120 includes a first fluid reservoir portion for holding a first fluid composition and a second fluid reservoir portion. Reservoir portion 120 further includes first initiator 160 and second initiator 170. First initiator 160 is configured to induce flow of the first fluid composition from the first fluid reservoir portion through an internal fluid conduit of penetrating portion 110, and out at least one of the plurality of pores 150. Second initiator 170 is configured to induce flow into or out of the second fluid reservoir portion through a central lumen and out penetrating edge 130.

Figure 2A:
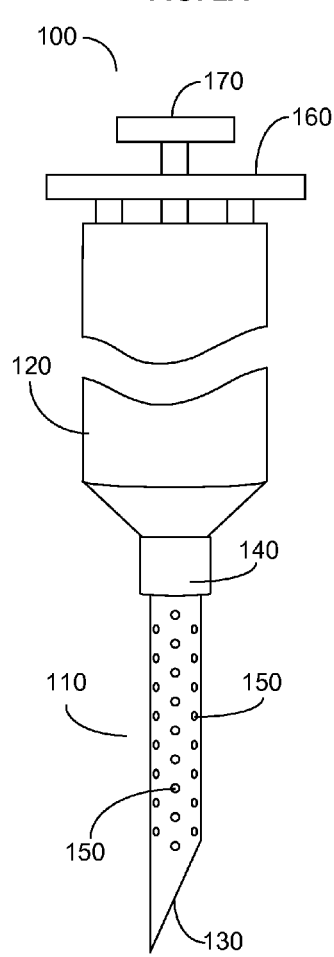
FIG. 2A shows a schematic of an external view of a penetrating device.
Figure 2B:
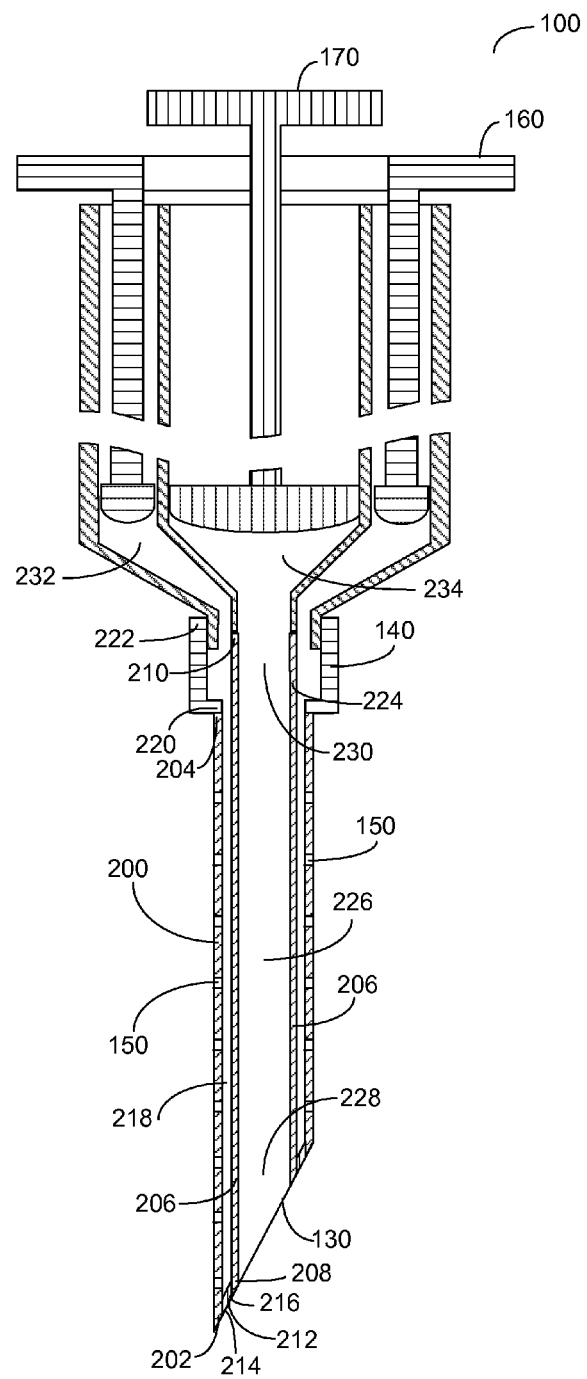
FIG. 2B shows a schematic of a longitudinal cross-section through a penetrating device.

FIGS. 2A and 2B illustrate further aspects of a penetrating device such as shown in FIG. 1. FIG. 2A shows a schematic of an exterior view of penetrating device 100. Penetrating device 100 includes penetrating portion 110 and reservoir portion 120. Penetrating portion 110 includes penetrating edge 130, connector portion 140, and plurality of pores 150. Penetrating portion 110 is connected to reservoir portion 120 through connector portion 140. Reservoir portion 120 includes first initiator 160 and second initiator 170.

FIG. 2B shows a schematic of a longitudinal cross-section through penetrating device 100. Penetrating device 100 includes a first hollow cylinder 200 having a first end 202 and a second end 204, the first hollow cylinder 200 including plurality of pores 150. Penetrating device 100 further includes a second hollow cylinder 206 having a first end 208 and a second end 210, the second hollow cylinder 206 is disposed within the first hollow cylinder 200 and substantially coaxial to the first hollow cylinder 200. Penetrating device 100 further includes a substantially ring-shaped end piece 212 having an outer edge 214 and an inner edge 216, the outer edge 214 of the substantially ring-shaped end piece 212 secured to the first end 202 of the first hollow cylinder 200 and the inner edge 216 of the substantially ring-shaped end piece 212 secured to the first end 208 of the second hollow cylinder 206, wherein the first hollow cylinder 200, the second hollow cylinder 206, and the substantially ring-shaped end piece 212 form a penetrating edge 130. Penetrating device 100 further includes internal fluid conduit 218 defined by a space between the first hollow cylinder 200 and the substantially coaxial second hollow cylinder 206, the internal fluid conduit 218 in fluid communication with the plurality of pores 150 along the length of first hollow cylinder 200. Penetrating device 100 includes a connector portion 140 with a first end 220 and a second end 222, the connector portion 140 disposed over and coaxial to a region 224 of second hollow cylinder 206 proximal to the second end 210 of the second hollow cylinder 206, the first end 220 of the connector portion 140 attached proximal to the second end 204 of the first hollow cylinder 200, the connector portion 140 in fluid communication with the internal fluid conduit 218. Penetrating device 100 further includes a lumen 226 defined by the second hollow cylinder 206, the lumen 226 having a first end 228 and a second end 230, the first end 228 of the lumen 226 in fluid communication with the penetrating edge 130. Reservoir portion 120 of penetrating device 100 includes first fluid reservoir portion 232 for holding a first fluid composition, the first fluid reservoir portion 232 associated with the second end 222 of the connector portion 140, the first fluid reservoir portion in fluid communication with the connector portion 140 and the internal fluid conduit 218. Reservoir portion 120 of penetrating device 100 includes second fluid reservoir portion 234, the second fluid reservoir portion 234 associated with the second end 210 of the second hollow cylinder 206, the second fluid reservoir portion 234 in fluid communication with the lumen 226 defined by the second hollow cylinder 206. Penetrating device 100 includes a first initiator 160 configured to induce flow of the first fluid composition from the first fluid reservoir portion 232, through the internal fluid conduit 218, and out at least one of the plurality of pores 150. Penetrating device 100 includes a second initiator 170 configured to induce flow into or out of the second fluid reservoir portion 234, through the lumen 226 defined by the second hollow cylinder 206.

Figure 3:
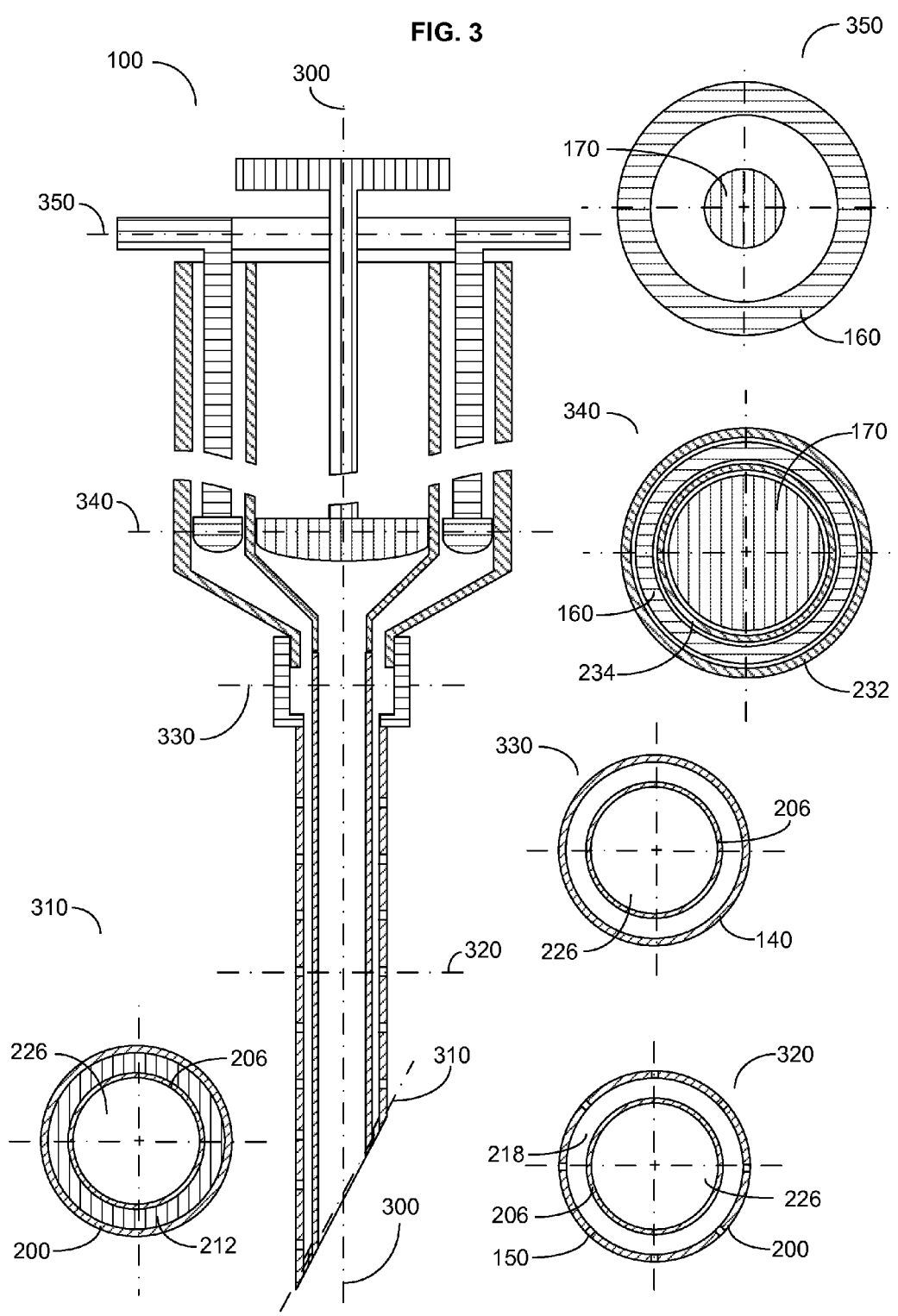
FIG. 3 shows a schematic of longitudinal and transverse cross-sections through a penetrating device.

FIG. 3 illustrates further aspects of penetrating device 100. Shown are cross-sections 310, 320, 330, 340, and 350 through the central axis 300 of penetrating device 100. Cross-section 310 shows a diagonal cross-sectional view through first hollow cylinder 200, second hollow cylinder 206, and substantially ring-shaped end piece 212. The outer edge of substantially ring-shaped end piece 212 is secured to first hollow cylinder 200 and the inner edge of substantially ring-shaped end piece 212 is secured to second hollow cylinder 206. The central portion of cross-section 310 includes lumen 226 defined by second hollow cylinder 206. Cross-section 320 shows a transverse cross-sectional view through first hollow cylinder 200 and second hollow cylinder 206. First hollow cylinder 200 further includes a plurality of pores 150. Also shown is internal fluid conduit 218 defined by a space between first hollow cylinder 200 and second hollow cylinder 206. In an aspect, the space between the first hollow cylinder and the second hollow cylinder is not contiguous. For example, the first hollow cylinder and the second hollow cylinder may be connected through one or more struts. The central portion of cross-section 320 includes lumen 226 defined by second hollow cylinder 206. Cross-section 330 shows a transverse cross-sectional view through connector portion 140 and second hollow cylinder 206. Connector portion 140 is shown disposed coaxial to second hollow cylinder 206. Connector portion 140 and second hollow cylinder 206 define a space in fluid communication with the internal fluid conduit. The central portion of cross-section 330 includes lumen 226 defined by second hollow cylinder 206. Cross-section 340 shows a transverse cross-sectional view through first initiator 160 and second initiator 170. In an aspect, first initiator 160 and second initiator 170 each include a plunger, e.g., a syringe plunger. Cross-section 340 includes first fluid reservoir portion 232 and second fluid reservoir portion 234. In an aspect, second fluid reservoir portion 234 is disposed within the first fluid reservoir portion 232 and substantially coaxial to the first fluid reservoir portion 232. First initiator 160 is disposed in first fluid reservoir portion 232 and second initiator 170 is disposed in second fluid reservoir portion 234. Cross-section 350 shows a transverse cross-sectional view through another portion of first initiator 160 and second initiator 170. In an aspect, a portion of second initiator 170 is disposed within first initiator 160 and substantially coaxial to first initiator 160.

Figure 4:
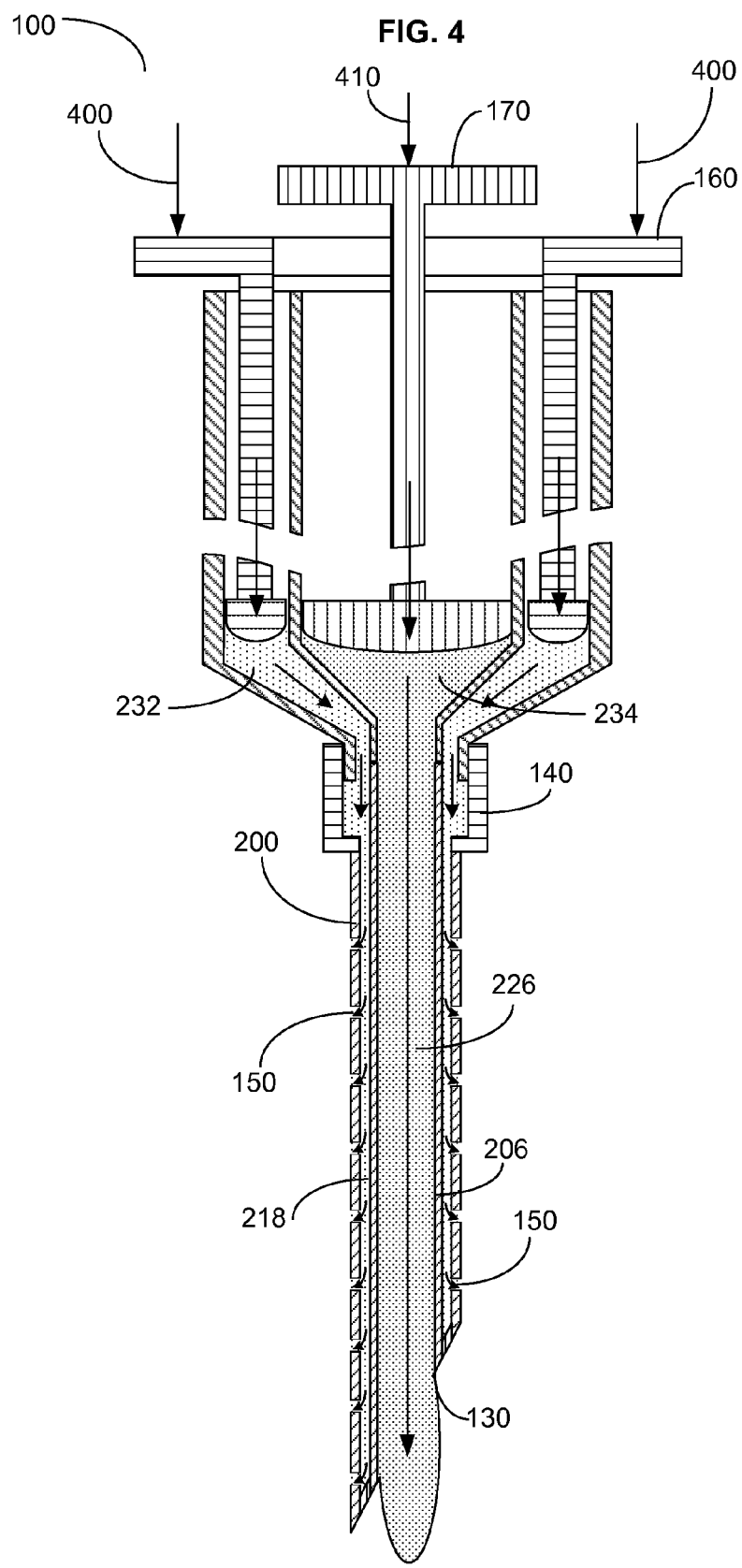
FIG. 4 shows a schematic of a longitudinal cross-section through a penetrating device.

FIG. 4 illustrates further aspects of penetrating device 100. FIG. 4 shows a schematic of fluid flow in response to actuation of first initiator 160 and second initiator 170 of penetrating device 100. Shown is actuation of first initiator 160 with downward pressure 400 into first fluid reservoir portion 232, inducing flow of the first fluid composition from first fluid reservoir portion 232, through connector portion 140, into internal flow conduit 218, and out at least one of the plurality of pores 150 along the length of first hollow cylinder 200. Also shown is actuation of second initiator 170 with downward pressure 410 into second fluid reservoir portion 234, inducing flow from second fluid reservoir portion 234, through lumen 226 defined by second hollow cylinder 206, and out penetrating edge 130. In an aspect, the first fluid composition flows out laterally along the length of the penetrating portion while the second fluid composition flows out the end of the penetrating portion.

In an aspect, first initiator 160 is actuated with downward pressure to induce flow of the first fluid composition from the first fluid reservoir portion, through the connector portion, into the internal flow conduit, and out at least one of the plurality of pores while second initiator 170 is actuated with upward pressure to induce flow of a second fluid composition through the lumen and into the second fluid reservoir portion. For example, the second initiator can be actuated with upward pressure to draw a fluid composition into the second fluid reservoir portion. For example, the second initiator can be actuated with upward pressure to aspirate a captured sample, e.g., blood, tissue, marrow, or cerebral spinal fluid, into the lumen defined by the second hollow cylinder and into the second fluid reservoir portion.

Penetrating device 100 includes first hollow cylinder 200. In an aspect, the diameter of the first hollow cylinder is dependent upon the material being penetrated, e.g., pierced, by the penetrating device. In an aspect, the diameter of the first hollow cylinder is sized for use in administering to an animal, e.g., a mammalian subject, an injectable agent, e.g., a vaccine or therapeutic agent, into a tissue of the animal. In an aspect, the diameter of the first hollow cylinder is sized for use in removing from an animal a bodily tissue, e.g., blood or other aspirate, or solid or semi-solid material. In an aspect, the diameter of the first hollow cylinder is sized for use in both delivering and removing fluid from an animal a bodily tissue, e.g., as in a wash aspirate. In an aspect, the cross-sectional diameter of the first hollow cylinder is about 5 millimeters to about 0.1 millimeters. For example and without limitation, the cross-section diameter of the first hollow cylinder can be 5 millimeters, 4.8 millimeters, 4.6 millimeters, 4.4 millimeters, 4.2 millimeters, 4.0 millimeters, 3.8 millimeters, 3.6 millimeters, 3.4 millimeters, 3.2 millimeters, 3.0 millimeters, 2.8 millimeters, 2.6 millimeters, 2.4 millimeters, 2.2 millimeters, 2.0 millimeters, 1.8 millimeters, 1.6 millimeters, 1.4 millimeters, 1.2 millimeters, 1.0 millimeters, 0.9 millimeters, 0.8 millimeters, 0.7 millimeters, 0.6 millimeters, 0.5 millimeters, 0.4 millimeters, 0.3 millimeters, 0.2 millimeters, or 0.1 millimeters.

In an aspect, the cross-sectional diameter of the first hollow cylinder is sized for agricultural use. For example, the first hollow cylinder can be sized for piercing a plant (e.g., a tree, shrub, flowering plant, food plant, etc.). For example, the first hollow cylinder can be sized for piercing a tissue (e.g, a stem or root) of a plant. For example, the first hollow cylinder can be sized for piercing a plant bed, plant container, or planted soil. In an aspect, the diameter of the first hollow cylinder is sized for use in agriculture for administering a substance to a plant or its environs. In an aspect, the diameter of the first hollow cylinder is sized for use in agriculture for removing a substance from a plant (e.g., tapping) or its environs. For example and without limitation, the cross-sectional diameter of the first hollow cylinder is about 0.1 centimeters to about 10 centimeters.

In an aspect, the cross-sectional diameter of the first hollow cylinder is sized for industrial use. For example, the first hollow cylinder can be sized for piercing metal, wood, concrete, plastic, polymer, fiberglass, resin, acrylic, latex, rubber, paper, or fabric. In an aspect, the diameter of the first hollow cylinder is sized for use in manufacturing (e.g., in dispensing). For example and without limitation, the cross-sectional diameter of the first hollow cylinder is about 0.5 centimeters to about 10 centimeters.

In an aspect, the length of the first hollow cylinder is dependent upon the material being penetrated, e.g., pierced, by the penetrating device. In an aspect, the length of the penetrating portion of the penetrating device is dependent upon the length of the first hollow cylinder. In an aspect, the length of the first hollow cylinder is appropriately sized for piercing a tissue of an animal. In an aspect, the length of the first hollow cylinder is appropriately sized for piercing a tissue of a mammalian subject. In an aspect, the length of the first hollow cylinder is comparable to the length of a standard hypodermic needle. In an aspect, the first hollow cylinder is about ½ inch to about 2 inch in length. For example, the first hollow cylinder can be ½ inch, ⅝ inch, 1 inch, 1½ inches, or 2 inches in length. In an aspect, the length of the first hollow cylinder is comparable to the length of a standard fine biopsy needle. In an aspect, the length of the first hollow cylinder is comparable to the length of a standard bone-access device, e.g., a bone biopsy or delivery device. In an aspect, the length of the first hollow cylinder is comparable to the length of a standard biopsy needle. In an aspect, the first hollow cylinder is about ½ inch to about 20 inches in length. For example, the first hollow cylinder can be ½ inch, 1 inch, 1½ inches, 2 inches, 2½ inches, 3 inches, 3½ inches, 4 inches, 4½ inches, 5 inches, 5½ inches, 6 inches, 6½ inches, 7 inches, 7½ inches, 8 inches, 8½ inches, 9 inches, 9½ inches, 10 inches, 10½ inches, 11 inches, 11½ inches, 12 inches, 12½ inches, 13 inches, 13½ inches, 14 inches, 14½ inches, 15 inches, 15½ inches, 16 inches, 16½ inches, 17 inches, 17½ inches, 18 inches, 18½ inches, 19 inches, 19½ inches, or 20 inches in length.

In an aspect, the length of the first hollow cylinder is sized for agricultural use. For example, the first hollow cylinder can be sized for piercing a tissue of a plant, such as a flowering plant or tree, or its environs. In an aspect, the cross-sectional diameter of the first hollow cylinder is sized for industrial use. For example and without limitation, the length of the first hollow cylinder is about ½ inch to about 20 inches in length.

In an aspect, the first hollow cylinder is formed from stainless-steel. In an aspect, the first hollow cylinder is formed from type 304 or A2 stainless-steel tubing including 18% chromium and 8% nickel. In an aspect, the first hollow cylinder is formed from 304L, 316, or 316L types of steel. In an aspect, the first hollow cylinder is formed from a stainless-steel tube through the process of tube drawing. For example, the first hollow cylinder can be formed from a stainless-steel tube by drawing the tube through progressively smaller dies until an appropriate outer diameter is achieved. Non-limiting examples of tube drawing techniques include tube sinking, mandrel drawing, stationary mandrel, moving mandrel, or floating mandrel, wherein a mandrel, e.g., a steel rod, is used to define the inner diameter of the stainless-steel tube as the tube is drawn through the die.

In an aspect, the first hollow cylinder is formed from at least one metal, alloy, plastic, glass, polymer, or ceramic. In an aspect, the first hollow cylinder is formed from at least one metal, e.g., iron, titanium, molybdenum, cobalt, chromium, zinc, magnesium, and nickel. In an aspect, the first hollow cylinder is formed from an alloy, e.g., iron-chromium-nickel alloys, cobalt-chromium alloys, cobalt-nickel-chromium-molybdenum alloys, nickel-titanium alloys, or magnesium alloys.

In an aspect, the first hollow cylinder is formed from at least one material capable of being shaped, molded, or printed to form the first hollow cylinder. Non-limiting examples of shapeable, moldable, or printable materials includes acrylic, nylon, plastic, ceramic, resin, rubber, epoxy, thermoplastic, photopolymer, polyurethane, silicone, or latex. In an aspect, the first hollow cylinder is formed from a polymer. In an aspect, the first hollow cylinder is formed from plastic. For example, the first hollow cylinder can be formed from at least one of polystyrene, polymethylmethacrylate, or nylon using micro injection molding. See, e.g., Kim & Colton (2005) *J. Med. Eng. Technol.* 29:181-186, which is incorporated herein by reference. In an aspect, the first hollow cylinder is formed using one or more thermoplastic resins, non-limiting examples of which include polyether ether ketone (PEEK), polyetherimide (PEI), liquid crystal polymers (LCP), nylon, thermoplastic elastomer (TPE), thermoplastic polyurethane (TPU). In an aspect, the first hollow cylinder is formed using glass filled nylons or carbon filled LCP. Other non-limiting examples of injection molding materials include acrylonitrile butadiene styrene (ABS), acetal, nylon, polyetherimide (PEI), polycarbonate, polylactic acid, polypropylene, polyvinyl chloride, and thermoplastic elastomers.

In an aspect, the first hollow cylinder is formed from a porous material. In an aspect, the first hollow cylinder is formed from porous glass. For example, the first hollow cylinder can be formed from porous glass including nanometer and/or micrometer pores through metastable phase separation of borosilicate glasses, followed by liquid extraction of one of the formed phases, through a sol-gel process, or through sintering of glass powder. In an aspect, the first hollow cylinder is formed from porous ceramic. For example, the first hollow cylinder can be formed from aluminum oxide and/or silicon carbide.

In an aspect, the first hollow cylinder is manufactured from a porous material formed by sintering thermoplastic powders. Non-limiting examples of thermoplastic powders include polyethylene (PE), polypropylene (PP), polyvinylidene fluoride (PVDF), polytetrafluoroethylene (PTFE), PP-PE copolymers, and nylon.

In an aspect, the first hollow cylinder is formed from at least one of sintered metal particulate, glass particulate, or ceramic particulate. For example, the first hollow cylinder can be formed using an additive manufacturing process using a metal, glass, or ceramic particulate and a laser to sinter the particulate material into a solid structure defined by a 3D model. For example, the first hollow cylinder can be formed using selective laser melting to fully melt the particulate material. In an aspect, the metal particulate includes a metal alloy. Non-limiting examples of metal alloys include stainless steel, maraging steel, cobalt chromium, inconel (nickel-chromium alloys), and titanium alloys. In an aspect, the sintered ceramic particulate includes aluminum oxide, zirconium dioxide, or calcium hydroxylapatite.

In an aspect, the first hollow cylinder is formed using an additive manufacturing process. Additive manufacturing refers to a class of manufacturing process in which a three-dimensional object is built by adding layers of material upon one another. Other terms include layered manufacturing, direct digital manufacturing, or solid freeform fabrication. Non-limiting examples of additive manufacturing processes include liquid-based processes, e.g., stereolithography, jetted photopolymer, and ink jet printing; powder-based processes, e.g., selective laser sintering, direct metal laser sintering, and three-dimensional printing; and solid-based processes, e.g., laminated object manufacturing, fused deposition modeling. In an aspect, the first hollow cylinder is formed using a subtractive manufacturing process. Subtractive manufacturing refers to a class of manufacturing process in which a three-dimensional object is built by cutting away material. Non-limiting examples of subtractive manufacturing processes include machining, milling, turning, and drilling. Other non-limiting examples of manufacturing processes include molding, e.g., blow molding, injection molding, or thermoforming; and casting, e.g., centrifugal casting, die casting, sand casting, shell mold casting.

In an aspect, the first hollow cylinder is generated using stereolithography using one or more optically curable photopolymers. Non-limiting examples of materials useful for stereolithography include poly(ethylene glycol) 1500, Accura 60, Accura 25, Accura Xtreme, Somos 9420, Somos 11122, Somos 18420, Somos DMX, Rigi2200, TuskXC2700T/Tusk2700W, Nano5000, Flex45, Flex65, Flex70B, Flex 80, Protogen White. Other non-limiting examples of stereolithography include three-dimensional printing (3D printing), optical fabrication, photo-solidification, solid free-form fabrication, and solid imaging.

In an aspect, the first hollow cylinder is generated by 3D printing using an inkjet technology, e.g., PolyJet™ (from Objet Ltd) in which photopolymer materials are jetted in ultra-thin layers onto a build tray and cured layer by layer with UV light. Non-limiting examples of materials for use in generating a wearable injection guide using inkjet technology include Fullcure 720, VeroWhite, VeroBlack, VeroBlue, and VeroGray for rigid structures; Durus for semi-flexible structures; and Tango Elastomers for rubber-like structures. Other examples of 3D printers include ProJet and ZPrinters available from 3D Systems Corporation, Rock Hill S.C. and Freeform Pico, Asiga, Anaheim Hills, Calif.

In an aspect, the first hollow cylinder is generated using selective laser sintering in which a high power laser, e.g., a carbon dioxide laser, is used to fuse small particles of plastic, metal, ceramic, glass powders, or combinations thereof into a mass that has a desired three-dimensional shape. Non-limiting examples of material for use in generating a first hollow cylinder using laser sintering include polyamide, nylon, carbon, hydroxyapatite, glass filled polyamide, and alumide.

In an aspect, the first hollow cylinder is generated using fused deposition modeling. Fused deposition modeling is an extrusion based three-dimensional modeling process using thermoplastic materials. Non-limiting examples of materials for use in fused deposition modeling include the thermoplastics ABS, ABS/F1, polycarbonate, and Ultem 9085. The uPrint SE from Stratasys (Eden Prairie, Minn.) or the Dimension Elite 3D printer from Dimension, Inc. (Eden Prairie, Minn.) are non-limiting examples of systems for fused deposition modeling with thermoplastics.

In an aspect, all or part of device 100 is manufactured using a manufacturing process in combination with computer-aided engineering software. For example, a three-dimensional rendering of all or part of device 100 can be created using a computer-aided engineering software practice, the three-dimensional rendering used as a template for micro injection molding with a thermoplastic resin. For example, a stereolithography file including a three-dimensional rendering of all or part of the device can be generated using a computer-aided design (CAD) program. Non-limiting examples of modeling software include MoldFlow®, Modex3D®, CADMOULD®, and SIGAMA®. See, e.g., Xie et al (2011) Modelling and Simulation for Injection Molding Process, in "Computational Fluid Dynamics Technology" ed. Igor Minin, InTech, ISBN 978-953-307-169-5, which is incorporated herein by reference.

The first hollow cylinder includes a plurality of pores. In an aspect each of the plurality of pores is substantially perpendicular to a central axis of the first hollow cylinder. In an aspect, each of the plurality of pores is oriented at 90 degrees relative to the central axis of the first hollow cylinder. In an aspect, each of the plurality of pores is oriented at 45 degrees relative to the central axis of the first hollow cylinder. In an aspect, each of the plurality of pores is oriented at about 90 degrees to about 20 degrees relative to the central axis of the first hollow cylinder. For example, each of the plurality of pores can be oriented at 90 degrees, 85 degrees, 80 degrees, 75 degrees, 70 degrees, 65 degrees, 60 degrees, 55 degrees, 50 degrees, 45 degrees, 40 degrees, 35 degrees, 30 degrees, 25 degrees, or 20 degrees relative to the central axis of the first hollow cylinder. In an aspect, each of the plurality of pores is at substantially the same angle relative to the central axis of the first hollow cylinder. For example, each of the plurality of pores can be machined at a substantially 90 degrees relative to the central axis of the first hollow cylinder. In an aspect, one or more of the plurality of pores are at different angles relative to the central axis of the first hollow cylinder. For example, a first hollow cylinder manufactured from a porous material, e.g., porous ceramic, may have pores angled at varied degrees relative to the central axis of the first hollow cylinder.

In an aspect, the plurality of pores includes at least two pores. In an aspect, the plurality of pores includes 2 pores to about 100 pores. For example, the plurality of pores can include 2 pores, 3 pores, 4 pores, 5 pores, 6 pores, 7 pores, 8 pores, 9 pores, 10 pores, 15 pores, 20 pores, 25 pores, 30 pores, 35 pores, 40 pores, 45 pores, 50 pores, 55 pores, 60 pores, 65 pores, 70 pores, 75 pores, 80 pores, 85 pores, 90 pores, 95 pores, or 100 pores. In an aspect, the plurality of pores includes about 100 pores to about 100,000 pores. In an aspect, the plurality of pores includes over 100,000 pores. In an aspect, the number of pores is dependent upon the manufacturing process. For example, forming the plurality of pores by manufacturing the first hollow cylinder from a porous material may include substantially more pores than forming the plurality of pores by machining the pores into the first hollow cylinder.

In an aspect, the plurality of pores is distributed over the entirety of the first hollow cylinder. In an aspect, the plurality of pores is distributed over a portion of the first hollow cylinder. For example, the plurality of pores can be distributed towards the first end of the first hollow cylinder. For example, the plurality of pores can be distributed towards the second end of the first hollow cylinder. For example, the plurality of pores can be concentrated to side of the first hollow cylinder.

In an aspect, the plurality of pores includes pores of at least one first size and pores of at least one second size. The plurality of pores of the first size may be distributed in a first location along the length of the first hollow cylinder and the plurality of pores of the second size may be distributed in a second location along the length of the first hollow cylinder. In an aspect, the plurality of pores include at least one first set of pores at a first angle relative to the central axis of the first hollow cylinder and at least one second set of pores at a second angle relative to the central axis of the first hollow cylinder. The plurality of pores at the first angle may be distributed in a first location along the length of the first hollow cylinder and the plurality of pores at the second angle may be distributed in a second location along the length of the first hollow cylinder.

In an aspect, each of the plurality of pores is machined into the first hollow cylinder. In an aspect, each of the plurality of pores is machined into the first hollow cylinder with a drill. In an aspect, each of the plurality of pores is machined into the first hollow cylinder using pins and/or needles. For example, the plurality of pores can be machined into the first hollow cylinder using a rotary pinned perforation roller with either cold or hot pins. In an aspect, each of the plurality of pores is machined into the first hollow cylinder with a laser. Non-limiting examples of lasers for laser cutting and/or boring include $CO_2$ lasers, neodymium (Nd) lasers, or neodymium yttrium-aluminum-garnet (Nd-YAG) lasers. In an aspect, each of the plurality of pores is machined into the first hollow cylinder using a waterjet cutter. For example, each of the plurality of pores can be machined into the first hollow cylinder using a waterjet cutter with or without an added abrasive, e.g., garnet or aluminum oxide.

Penetrating device 100 includes second hollow cylinder 206. In an aspect, the second hollow cylinder is formed from stainless steel. In an aspect, the second hollow cylinder is formed from at least one of metal, alloy, plastic, glass, polymer, or ceramic. Non-limiting examples of stainless steel, metals, alloys, plastics, glass, polymers, and ceramics have been described above herein. In an aspect, the second hollow cylinder is formed from the same material as the first hollow cylinder. In an aspect, the second hollow cylinder is formed from a material that differs from that used to form the first hollow cylinder.

In an aspect, the cross-sectional diameter of the second hollow cylinder is about 5 millimeters to about 0.2 millimeters. For example, the cross-section diameter of the first hollow cylinder can be 5 millimeters, 4.8 millimeters, 4.6 millimeters, 4.4 millimeters, 4.2 millimeters, 4.0 millimeters, 3.8 millimeters, 3.6 millimeters, 3.4 millimeters, 3.2 millimeters, 3.0 millimeters, 2.8 millimeters, 2.6 millimeters, 2.4 millimeters, 2.2 millimeters, 2.0 millimeters, 1.8 millimeters, 1.6 millimeters, 1.4 millimeters, 1.2 millimeters, 1.0 millimeters, 0.9 millimeters, 0.8 millimeters, 0.7 millimeters, 0.6 millimeters, 0.5 millimeters, 0.4 millimeters, 0.3 millimeters, or 0.2 millimeters. In an aspect, the cross-sectional diameter of the second hollow cylinder is about 0.5 centimeters to about 30 centimeters. In an aspect, the cross-sectional diameter of the second hollow cylinder is less than the cross-sectional diameter of the first hollow cylinder. For example, the cross-sectional diameter of the second hollow cylinder is appropriately sized relative to the first hollow cylinder to allow the second hollow cylinder to be disposed within the first hollow cylinder. In an aspect, the cross-sectional diameter of the second hollow cylinder relative to the cross-sectional diameter of the first hollow cylinder dictates the thickness of the internal fluid conduit.

Penetrating device 100 includes substantially ring-shaped end piece 212. The substantially ring-shaped end piece is configured to attach to the first end of the first hollow cylinder and to the first end of the second hollow cylinder to form an enclosed or sealed end to the internal fluid conduit formed between the first and second hollow cylinders. In an aspect, the substantially ring-shaped end piece is formed from at least one of stainless steel, metal, alloy, plastic, glass, polymer, or ceramic. In an aspect, the substantially ring-shaped end piece and the second hollow cylinder are substantially non-porous. For example, the substantially ring-shaped end piece and the second hollow cylinder are substantially impervious to the first fluid composition as it flows from the first fluid reservoir portion through the internal fluid conduit and out at least one of the plurality of pores along the length of the first hollow cylinder. In an aspect, the first hollow cylinder, the second hollow cylinder, and the substantially ring-shaped end piece are formed from the same material. In an aspect, the first hollow cylinder, the second hollow cylinder, and/or the substantially ring-shaped end piece are formed as a single unit. For example, the first hollow cylinder, the second hollow cylinder, and the substantially ring-shaped end piece can be formed using one of the fabrication methods described above herein. In an aspect, the first hollow cylinder, the second hollow cylinder, and/or the substantially ring-shaped end piece are formed from different materials. In an aspect, the first hollow cylinder, the second hollow cylinder, and the substantially ring-shaped end piece are formed as separate pieces and connected together. For example, the first hollow cylinder, the second hollow cylinder, and/or the substantially ring-shaped end piece can be formed as separate pieces and glued together with an adhesive. Alternatively, the separate pieces can be adhered together using a heat welding method, e.g., to melt and/or fuse together the separate pieces. Alternatively, the separate pieces can include male and/or female connector parts for use in snapping the separate pieces together.

In an aspect, the outer edge of the substantially ring-shaped end piece is secured to the first hollow cylinder at a location that is not the first end of the first hollow cylinder and the inner edge of the substantially ring-shaped end piece is secured to the second hollow cylinder at a location that is not the first end of the second hollow cylinder. For example, the substantially ring-shaped end piece can be secured to the first and second hollow cylinders at a location between the first ends and the second ends of the first and second hollow cylinders along the length of the first and second hollow cylinders. For example, the substantially ring-shaped end piece can be secured to the first and second hollow cylinders at a location equidistant between the first and second ends of the first and second hollow cylinders.

First hollow cylinder 200 and second hollow cylinder 206 and substantially ring-shaped end piece 212 form penetrating edge 130. In an aspect, the penetrating edge includes a sharp piercing edge. In an aspect, the penetrating edge includes a sharp beveled edge. In an aspect, the penetrating edge includes at least one sharp edge able to pierce a material. In an aspect, the penetrating edge includes a standard bevel. In an aspect, the penetrating edge includes a short bevel. In an aspect, the penetrating edge includes a true short bevel. In an aspect, the penetrating edge includes a cone needle tip. In an aspect, the penetrating edge includes a bias grind edge, a vet point edge, a lancet point edge, a deflected point edge, a razor edge, a probe point (blunt end) edge, a trocar edge, a diamond point edge, a Trephine edge, or a Menghini edge. In an aspect, the penetrating edge includes at least one sharp edge able to pierce metal, wood, concrete, plastic, polymer, fiberglass, resin, acrylic, latex, rubber, paper, or fabric.

In an aspect, the penetrating edge includes at least one sharp edge able to pierce a body tissue of an animal. In an aspect, the penetrating edge includes at least one sharp edge able to pierce skin, endothelium, muscle, adipose, bone, cartilage, eye tissue, neural tissue, or internal organ tissue. In an aspect, the penetrating edge includes at least one sharp edge able to pierce a plant tissue or environs. In an aspect, the penetrating edge includes at least one sharp edge able to pierce an industrial material.

Penetrating device 100 includes connector portion 140. The second end of connector portion 140 is associated with the first fluid reservoir portion. Connector portion 140 is configured to attach the penetrating portion of penetrating device 100 to the first and second fluid reservoir portions. In an aspect, the first fluid reservoir portion 232 is attached to the second end of connector portion 140. In an aspect, connector portion 140 forms a seal with at least a portion of a wall defining the first fluid reservoir portion 232. In an aspect, the seal is a frictional seal. For example, at least a part of the connector portion and at least a part of the first fluid reservoir portion can be sized to fit into one another, e.g., through a male/female coupling. In an aspect, the seal is an adherent seal. For example, at least a part of the connector portion and at least a part of the first fluid reservoir portion may be glued or otherwise secured to one another.

In an aspect, connector portion 140 includes a fitting. For example, the connector portion can include a fitting that enables attachment to the first fluid reservoir portion. In an aspect, the connector portion 140 includes a slip-tip fitting. In an aspect, the connector portion is sized to slip over an appropriately sized portion of the first fluid reservoir portion. For example, the connector portion can include an inner diameter just large enough for insertion of a portion of the first fluid reservoir portion. In an aspect, the connector portion is sized to slip into an appropriately sized portion of the first fluid reservoir portion. For example, the connector portion can include an outer diameter just small enough to slip into a portion of the first fluid reservoir portion. In an aspect, connector portion 140 includes a Luer lock fitting. For example, the connector portion and/or a portion of the first fluid reservoir portion can include threads that allow the two portions to be connected to one another, e.g., by screwing the matched threads together. In an aspect, the connector portion includes external threads while the first fluid reservoir portion includes internal threads, such that the connector portion screws on over a portion of the first fluid reservoir portion. In an aspect, the connector portion includes internal threads while the first fluid reservoir portion includes external threads, such that the connector portion screws into a portion of the first fluid reservoir portion.

In an aspect, connector portion 140 is manufactured from metal or metal alloy, e.g., stainless steel. In an aspect, connector portion 140 is manufactured from plastic. In an aspect, connector portion 140 is manufactured from plastic using an injection molding technique. In an aspect, the connector portion is formed from the same material as the first hollow cylinder. In an aspect, the connector portion is formed from a material that differs from the material used to form the first hollow cylinder. In an aspect, the connector portion and the first hollow cylinder are formed as one piece. In an aspect, the connector portion and the first hollow cylinder are formed as separate pieces and subsequently secured to one another, e.g., by adhesive or heat welding.

Reservoir portion 120 further includes second fluid reservoir portion 234 associated with the second end of second hollow cylinder 206. Second fluid reservoir portion 234 is in fluid communication with the lumen defined by the second hollow cylinder. In an aspect, the second fluid reservoir portion is configured to hold a second fluid composition, e.g., a vaccine, therapeutic agent, dye, or other fluid composition. For example, the second fluid reservoir portion can hold a vaccine, therapeutic agent, and/or dye intended for delivery to an animal subject. In an aspect, the second fluid reservoir portion is configured to hold a captured sample, e.g., a blood sample, a marrow sample, and/or a tissue sample. For example, the second fluid reservoir portion can hold a captured sample drawn up or aspirated from an animal subject. In an aspect, the second fluid reservoir portion is configured to hold a second fluid composition at a first time point and a captured sample at a second time point. For example, the second fluid reservoir portion of the penetrating device can be used for a wash aspirate in which a wash solution, e.g., saline, is delivered from the second fluid reservoir portion, and a captured sample, e.g., a nasal sample including the wash solution, is aspirated back into the second fluid reservoir portion.

In an aspect, second fluid reservoir portion 234 forms a seal with at least a portion of the second end of second hollow cylinder 206. In an aspect, the seal is a frictional seal. For example, at least a part of the second fluid reservoir portion and at least a part of the second end of second hollow cylinder 206 can be sized to fit into one another, e.g., through a male/female coupling. In an aspect, the seal is an adherent seal. For example, at least a part of the second fluid reservoir portion and at least a part of the second end of second hollow cylinder 206 may be glued or otherwise secured to one another.

In an aspect, the first fluid reservoir portion includes a first hollow tube and the second fluid reservoir portion includes a second hollow tube, the second hollow tube disposed within the first hollow tube. For example, the first fluid reservoir portion and the second fluid reservoir portion can be concentric to one another. See, e.g., U.S. Patent Application No. 2007/0083155 to Muller and titled "Multi-lumen injection apparatus," which is incorporated herein by reference.

In an aspect, the first fluid reservoir portion and the second fluid reservoir portion are parallel to one another. In an aspect, the first fluid reservoir portion and the second fluid reservoir portion are parallel and concentric to one another, as illustrated in FIGS. 2-4. In an aspect, the first fluid reservoir portion and the second fluid reservoir portion are parallel to one another but not concentric. For example, the first fluid reservoir portion can include a first hollow tube and the second fluid reservoir portion can include a second hollow tube, the first hollow tube and the second hollow tube substantially parallel to one another. See, e.g., U.S. Pat. No. 6,972,005 to Boehm & Melnick titled "Dual chamber syringe and dual lumen needle," which is incorporated herein by reference.

FIGS. 5A and 5B illustrate aspects of a penetrating device including parallel first and second fluid reservoir portions. FIG. 5A is an external view of penetrating device 500 including a penetrating portion 510, a connector portion 520, and a fluid reservoir portion 530. Penetrating portion 510 includes a plurality of pores 512 and a penetrating edge 514. Connector portion 520 is configured to connect penetrating portion 510 to fluid reservoir portion 530. Fluid reservoir portion 530 includes first fluid reservoir portion 532 for holding a first fluid composition and a second fluid reservoir portion 534. In an aspect, the second fluid reservoir portion is configured to hold a second fluid composition. In an aspect, the second fluid reservoir portion is configured to hold a captured sample. First fluid reservoir portion 532 includes first initiator 536 configured to induce flow of the first fluid composition from first fluid reservoir portion 532, through an internal fluid conduit, and out at least one of the plurality of pores 512. Second fluid reservoir portion 534 includes a second initiator 538 configured to induce flow into or out of second fluid reservoir portion 534. FIG. 5B illustrates further aspects of penetrating device 500. Shown is a longitudinal cross-section through penetrating device 500. Penetrating device 500 includes a first hollow cylinder 540 having a first end 542 and a second end 544, first hollow cylinder 540 including plurality of pores 512. Penetrating device 500 includes second hollow cylinder 546 having a first end 548 and a second end 550, second hollow cylinder 546 disposed within first hollow cylinder 540 and substantially coaxial to first hollow cylinder 540. A substantially ring-shaped end piece 552 is attached to the first end 542 of first hollow cylinder 540 and first end 548 of second hollow cylinder 546, first hollow cylinder 540, second hollow cylinder 546, and substantially ring-shaped end piece 552 forming penetrating edge 514. Internal fluid conduit 554 is defined by a space between first hollow cylinder 540 and substantially coaxial second hollow cylinder 546, internal fluid conduit 554 in fluid communication with the plurality of pores 512 along the length of first hollow cylinder 540. Connector portion 520 includes a first end 556 attached proximal to the second end 544 of first hollow cylinder 540. Lumen 558 is defined by second hollow cylinder 546 and is in fluid communication with penetrating edge 514. First fluid reservoir portion 532 is attached to a portion of connector portion 520 and is in fluid communication with connector portion 520 and internal fluid conduit 554. Second fluid reservoir portion 534 is attached to the second end 550 of second hollow cylinder 546 and is in fluid communication with lumen 558 defined by second hollow cylinder 546. First initiator 536 is configured to induce flow of the first fluid composition from first fluid reservoir portion 532, through internal fluid conduit 554, and out at least one of the plurality of pores 512. Second initiator 538 is configured to induce flow into or out of second fluid reservoir portion 534, through lumen 558 defined by second hollow cylinder 546.

In an aspect, the first fluid reservoir portion is in fluid communication with the connector portion and the internal fluid conduit through a length of tubing. In an aspect, the second fluid reservoir portion is in fluid communication with the lumen defined by the second hollow cylinder through a length of tubing. FIGS. 6A and 6B illustrate an example of a penetrating device including a first fluid reservoir portion and/or a second fluid reservoir portion in fluid communication respectively with a connector portion and a lumen defined by the second hollow cylinder. FIG. 6A is a schematic showing an external view of penetrating device 600. Penetrating device 600 includes penetrating portion 610, connector portion 620, first fluid reservoir portion 630, and second fluid reservoir portion 640. Penetrating portion 610 includes plurality of pores 612 and penetrating edge 614. Connector portion 620 includes lid portion 650. Lid portion 650 includes first inlet 652 with a first tubing 654 attached to first fluid reservoir portion 630 and second inlet 656 attached with a second tubing 658 to second fluid reservoir portion 640. FIG. 6B is a schematic of a longitudinal cross-section of penetrating device 600. Penetrating device 600 includes first hollow cylinder 660 including a plurality of pores 612; second hollow cylinder 665 disposed within first hollow cylinder 660 and substantially coaxial to first hollow cylinder 660; substantially ring-shaped end piece 670 attached to a first end 662 of first hollow cylinder 660 and to a first end 668 of second hollow cylinder 665, wherein first hollow cylinder 660, second hollow cylinder 665, and substantially ring-shaped end piece 670 form penetrating edge 614; internal fluid conduit 675 defined by a space between first hollow cylinder 660 and second hollow cylinder 665, internal fluid conduit 675 in fluid communication with the plurality of pores 612; connector portion 620 disposed over and coaxial to a region 622 of second hollow cylinder 665, a first end 624 of connector portion 620 attached proximal to a second end 664 of first hollow cylinder 660, connector portion 620 in fluid communication with internal fluid conduit 675; and a lumen 680 defined by second hollow cylinder 665. Connector portion 620 further includes lid portion 650 which is secured to a second end 669 of second hollow cylinder 665 to form a seal and with a second end 626 of connector portion 620 to form a seal. Lid portion 650 includes inlet 652 with tubing 654 in fluid communication with first fluid reservoir portion 630 and inlet 656 with tubing 658 in fluid communication with second fluid reservoir portion 640.

In an aspect, the first fluid reservoir portion is configured for holding a first fluid composition. In an aspect, the first fluid composition includes at least one lubricant. In an aspect, the first fluid composition includes at least one lubricant intended to make piercing of a material by the penetrating portion of the penetrating device easier. In an aspect, the at least one lubricant includes a form of silicone. For example, the at least one lubricant can include at least one of silicone oil, silicone grease, silicone rubber, or silicone resin.

In an aspect, the at least one lubricant includes a biocompatible lubricant for use in piercing a tissue of a mammalian subject. For example, Dow Corning® MDX4-4159, a silicone fluid, has been described for coating hypodermic needles. See, e.g., U.S. Patent Application No. 2012/0059333 to Singhal titled "Apparatus and methods for reuse of injection needle for home users," which is incorporated herein by reference. For example, the biocompatible lubricant can include Endo-Glide™, a lubricant gel approved for used by the United States Food & Drug Administration that is biocompatible with tissues and all hollow viscera. For example, the biocompatible lubricant can include polyethylene glycol, for which a range of average molecular weights may be used, such as about 200 to about 600 g/mole. See, e.g., U.S. Pat. No. 6,259,953 to Lucchesi et al. titled "Cardiac lead with active fixation and biocompatible lubricant," which is incorporated herein by reference. In an aspect, the at least one lubricant includes a natural gum product with bacteriostatic properties. For example, the at least one lubricant can include a natural gum product with bacteriostatic properties such as, for example, Surgilube Bacteriostatic Sterile Lubricating Jelly™. In an aspect, the at least one lubricant includes a biocompatible lubricant comprising a biological agent. For example, the at least one lubricant includes liposomes or other lipid-based or fat-based agents. For example, the at least one lubricant includes hyaluronan.

In an aspect, the first fluid composition of the first fluid reservoir portion includes at least one of an anesthetic or an analgesic. In an aspect, the first fluid composition includes at least one local anesthetic, non-limiting examples of which includes lidocaine, procaine, amethocaine, cocaine, prilocaine, bupivacaine, levobupivacaine, ropivacaine, mepivacaine, or dibucaine. In an aspect, the first fluid composition includes at least one analgesic. Non-limiting examples of analgesics include non-steroidal anti-inflammatory drugs, e.g., salicylates or ibuprofen, opioids, e.g., morphine, codeine, oxycodone, or hydrocodone, paracetamol, acetaminophen, or cyclooxygenase inhibitors, e.g., COX-2 inhibitors.

In an aspect, the first fluid composition of the first fluid reservoir portion includes at least one antiseptic. In an aspect, the at least one antiseptic includes at least one disinfectant and/or sterilant. Non-limiting examples of antiseptics include isopropanol, silver compounds, ethanol, povidone, iodine, glutaraldehyde, formaldehyde, chlorhexidine gluconate, sodium hypochlorite, quaternary ammoniums compounds, hydrogen peroxide, and phenols.

In an aspect, the first fluid composition of the first fluid reservoir portion includes at least one antimicrobial agent. In an aspect, the first fluid composition includes at least one of an antibacterial agent, an antifungal agent, or an antiviral agent. In an aspect, the first fluid composition includes at least one antibacterial agent configured to prevent or minimize a bacterial infection at an injection site. Non-limiting examples of antibacterial agents commonly used for topical applications include benzoyl peroxide, sodium sulfacetamide, erythromycin, mupirocin, retapamulin, bacitracin, neomycin, polymyxin b/e, silver sulfadiazine, or tetracycline. In an aspect, the first fluid composition includes at least one antiviral agent configured to prevent or treat a viral infection at an injection site. Non-limiting examples of antiviral agents commonly used for topical applications include acyclovir, docosanol, famciclovir, imiquimod, penciclovir, valacyclovir, and vidarabine. In an aspect, the first fluid composition includes at least one antifungal agent configured to prevent or treat a fungal infection at an injection site. Non-limiting examples of antifungal agents commonly used for topical applications include clotrimazole, amphotericin B, butaconazole, butenafine, ciclopirox olamine, econazole, ketoconazole, miconazole, naftifine, natamycin, nystatin, oxiconazole, sulconazole, terbinafine, terconazole, tioconazole, and tolnaftate.

In an aspect, the first fluid composition of the first fluid reservoir portion includes at least one anticoagulant. In an aspect, the first fluid composition includes at least one of an antithrombotic, fibrinolytic, or thrombolytic agent to prevent blood coagulation. Non-limiting examples of anticoagulants include coumarins, e.g., warfarin; heparin and derivatives thereof, e.g., low molecular weight heparin, fondaparinux, or idraparinux; factor Xa inhibitors, e.g., rivaroxaban, apixaban, or edoxaban; or thrombin inhibitors, e.g., hirudin, lepirudin, bivalirudin, argatroban, or dabigatran.

In an aspect, the first fluid composition of the first fluid reservoir portion includes at least one antihemorrhagic agent. In an aspect, the first fluid composition includes at least one substance that promotes hemostasis or stops bleeding. In an aspect, the at least one antihemorrhagic agent includes at least one styptic, e.g., an agent that contracts tissue to seal injured blood vessels. In an aspect, the at least one antihemorrhagic agent causes vasoconstriction and/or platelet aggregation. Non-limiting examples includes microfibrillar collagen, chitosan, anhydrous aluminum sulfate, and microporous zeolite aluminosilicate minerals.

In an aspect, the first fluid composition of the first fluid reservoir portion includes at least one sealant. In an aspect, the at least one sealant is formulated to seal up the puncture site after withdrawal of the penetrating portion from the pierced tissue. In an aspect, the sealant can include an adhesive. In an aspect, the sealant can include a biocompatible sealant. For example, the sealant can include at least one of cyanoacrylate, octyl-2-cyanoacrylate, or n-butyl-cyanoacrylate. For example, the sealant can include Dermabond® or Histoacryl®. For example, the sealant can include fibrin glue.

In an aspect, the first fluid composition of the first fluid reservoir portion includes at least one treatment agent. In an aspect, the at least one treatment agent can include at least one adjuvant to a therapeutic or preventative agent. For example, the at least one treatment agent can include a cytokine or a chemokine, e.g., for use with a vaccine. For example, the at least one treatment agent can include an adjuvant for a vaccine. Non-limiting examples of adjuvants include aluminum gels, aluminum salts, oil-in-water emulsions, e.g., squalene-oil-in-water, water-in-oil emulsions, Freund's adjuvant, pattern recognition receptor ligands, e.g., Toll-Like Receptor (TRL) ligands, pathogens associated molecular patterns (PAMPs), or other agents capable of enhancing an immune response to a vaccine.

In an aspect, the first fluid composition is incorporated into the first fluid reservoir portion at the time of manufacture. For example, the first fluid composition can be incorporated into the first fluid reservoir portion by suction using a first initiator, e.g., a plunger, and the device locked to a position to prevent loss of the first fluid composition prior to use. For example, the first fluid composition can be incorporated into the first fluid reservoir portion by dispensing the first fluid composition into the first fluid reservoir portion and sealing the first fluid reservoir portion.

In an aspect, the first fluid composition is incorporated into the first fluid reservoir portion at the time of use. For example, the first fluid composition can be incorporated into the first fluid reservoir portion by suction using a first initiator, e.g., a plunger. For example, the penetrating portion can be inserted through the septum of an injection vial and a first fluid composition, e.g., a lubricant and/or an analgesic, drawn up into the first fluid reservoir portion. For example, the first fluid composition can be incorporated into the first fluid reservoir portion by dispensing the first fluid composition into the first fluid reservoir portion. For example, the first fluid composition can be included in a first fluid reservoir portion that is a cartridge connected just prior to use to the penetrating portion of the penetrating device. In an aspect, the cartridge is connected directly, e.g., fitted to the second end of the of the connector portion, or indirectly, e.g., through a flow conduit that includes surgical tubing.

Penetrating device 100 includes second fluid reservoir portion 234. Second fluid reservoir portion 234 is associated with the second end of the second hollow cylinder and is in fluid communication with the lumen defined by the second hollow cylinder. In an aspect the second fluid reservoir portion is configured to hold a captured sample. In an aspect the second fluid reservoir portion provides vacuum for use in capturing a captured sample, for example by suction using a second initiator, e.g., a plunger. In an aspect, the penetrating device is a blood sampling device and the second fluid reservoir portion holds aspirated blood. In an aspect, the penetrating device is an aspiration device. For example, the penetrating device is an aspiration device for acquiring an aspiration from an organ or viscera, e.g., aspiration of ascites fluid, aspiration of fluid surrounding an organ, or bone marrow aspiration. In an aspect, the penetrating device is a biopsy device, and the second fluid reservoir portion is configured to hold a captured biopsy sample or provides suction for capturing and holding a captured biopsy sample. For example, the penetrating device is a biopsy device for use in acquiring a tissue biopsy, e.g., from a soft tissue or bone, to look for an indication of a pathology, e.g., abnormal cells indicative of cancer, or the presence of a microbe indicating an infection.

In an aspect, the second fluid reservoir portion 234 of penetrating device 100 is configured to hold a second fluid composition. In an aspect, the second fluid composition includes at least one vaccine. Non-limiting examples of vaccines include vaccines against small pox, hepatitis A, hepatitis B, polio, mumps, measles, rubella, diphtheria, pertussis, tetanus, HiB, chickenpox, rotavirus, influenza, meningococcal disease, pneumonia, typhoid, anthrax, yellow fever, and the like. It is anticipated that other vaccines currently in development for human immunodeficiency virus (HIV) and cancer, for example, will be of use in the systems and methods described herein.

In an aspect, the second fluid composition includes at least one therapeutic agent. In an aspect, the at least one therapeutic agent includes at least one of an anti-inflammatory agent, an antimicrobial agent, a chemotherapeutic agent, or a diabetes treatment agent. In an aspect, the at least one anti-inflammatory agent includes at least one injectable antibody, cytokine, non-steroidal anti-inflammatory drug, or steroidal anti-inflammatory drug. Non-limiting examples of anti-inflammatory agents include teriparatide, etanercept, interferon, abatacept, anakinra, bevacizumab, cetuximab, cyclophosphamide, gemtuzamab, muromonab-CD3, omalizumab, pegademase, immune globulin, tacrolimus, or tositumomab. In an aspect, the at least one antimicrobial agent includes at least one of an antibiotic, antifungal agent, or antiviral agent. Non-limiting examples of antibiotics include penicillins, e.g., penicillin, ampicillin, piperacillin; cephalosporins and other beta-lactam drugs, e.g., cefazolin, ertapenem; tetracyclines, e.g., doxycycline; macrolides, e.g., erythromycin; clindamycin; aminoglycosides, e.g., streptomycin, gentamicin; spectinomycin; sulfonamides; quinolones and fluoroquinolones. Non-limiting examples of antiviral agents include protease inhibitors, neuraminidase inhibitors, integrase inhibitors, reverse transcriptase inhibitors, viral entry inhibitors, uncoating inhibitors, and translation inhibitors. In an aspect, the at least one hormone includes at least one of a hypothalamic or pituitary hormone, synthetic analogs, and/or antagonist thereof, e.g., adrenocorticotropic hormone, corticotropin-releasing hormone, follicle stimulating hormone, gonadotropin-releasing hormone and synthetic analogs, luteinizing hormone, prolactin; at least one of an adrenocoricosteroid, synthetic analogs, and/or antagonists thereof, e.g., dexamethasone, hydrocortisone, prednisolone, methylprednisolone, triamicinolone; gonadal hormones, e.g., estrogens, progestins, androgens, and anabolic steroids; glucagon and analogs thereof. In an aspect, at least one cancer chemotherapeutic or associated therapy includes at least one of alpha interferon, erythropoietin and derivatives thereof, colony stimulating factor and analogs thereof, somatostatin and analogs thereof.

In an aspect, the at least one diabetes treatment agent includes a form of insulin. Non-limiting examples of insulin include rapid acting insulin, short-acting insulins, intermediate-acting insulins, premixed insulins, or long-acting insulins. Commercial sources of insulin are available from, e.g., Eli Lilly (Indianapolis, Ind.), Sanofi-Aventis (Bridgewater N.J.), Novo Nordisk Inc. (Princeton, N.J.), or Pfizer (New York, N.Y.).

In an aspect, the second fluid composition includes at least one cosmetic enhancement agent. In an aspect, the second fluid composition includes at least one neurotoxin, subcutaneous volume enhancer, or dermal filler. In an aspect, the at least one neurotoxin includes botulinum toxin. Non-limiting examples of botulinum toxin include onabotulinumtoxinA, abobotulinumtoxinA, incobotulinymtoxinA, rimabotulinumtoxinB and like agents (see, e.g., Park et al., Clin. Ophthalmol. (2011) 5:725-732, which is incorporated herein by reference). In an aspect, the at least one dermal filler includes at least one collagen filler. Non-limiting examples of bovine-, porcine-, or human-derived collagen fillers include Artefill, Cosmoplast/Cosmoderm, Evolence, and Zyderm/Zyplast. In an aspect, the at least one dermal filler includes at least one hyaluronic acid filler. Non-limiting examples of hyaluronic fillers include Belotero Balance (from Merz Aesthetics); Hyalaform, Juvederm Ultra and Juvederm Ultra Plus (from Allergan, Inc.); Perlane and Restylane (from Medicis Aesthetics Inc.) PREVELLE and Puragen (from Mentor Corp.). Other non-limiting examples of subcutaneous volume enhancers or dermal fillers include adipose, fibroblasts, calcium microspheres, or poly L lactic acid.

In an aspect, the second fluid composition includes a dye, for example a dye for injection into an internal organ prior to further examination such as radiography, e.g., transhepatic cholangiography.

In an aspect, the second fluid composition includes a wash solution, e.g., a saline solution, for an aspiration wash. For example, the second fluid reservoir portion can include a wash solution that is delivered to a tissue and subsequently aspirated back into the second fluid reservoir portion along with aspirated captured sample.

In an aspect, the second fluid composition of the second fluid reservoir portion is configured for at least one of percutaneous administration, intravenous administration, subcutaneous administration, intraocular administration, intraosseus administration, epidural administration, intraarticular administration, intraperitoneal administration, intraoral administration, or intramuscular administration.

In an aspect, the second fluid composition is incorporated into the second fluid reservoir portion at the time of manufacture. For example, the second fluid composition can be incorporated into the second fluid reservoir portion by suction using a second initiator, e.g., a plunger, and the device locked to a position to prevent loss of the second fluid composition prior to use. For example, the second fluid composition can be incorporated into the second fluid reservoir portion by dispensing the second fluid composition into the second fluid reservoir portion and sealing the second fluid reservoir portion.

In an aspect, the second fluid composition is incorporated into the second fluid reservoir portion at the time of use. For example, the second fluid composition can be incorporated into the second fluid reservoir portion by suction using a second initiator, e.g., a plunger. For example, the penetrating portion can be inserted through the septum of an injection vial and a vaccine and/or therapeutic agent drawn up into the second fluid reservoir portion. For example, the second fluid composition can be incorporated into the second fluid reservoir portion by pouring the second fluid composition into the second fluid reservoir portion. For example, the second fluid composition can be included in a second fluid reservoir portion that is a cartridge connected just prior to use to the penetrating portion of the penetrating device. In an aspect, the cartridge is connected directly, e.g., fitted to the second end of the second hollow cylinder, or indirectly, e.g., through a flow conduit that includes surgical tubing.

Penetrating device 100 includes first initiator 160 and second initiator 170. The first initiator is configured to induce flow of the first fluid composition from the first fluid reservoir portion, through the internal fluid conduit, and out at least one of the plurality of pores. The second initiator is configured to induce flow into or out of the second fluid reservoir portion, through the lumen defined by the second hollow cylinder. In an aspect, at least one of the first initiator or the second initiator includes an actuator.

In an aspect, at least one of the first initiator or the second initiator includes a plunger. In an aspect, the plunger includes aspects of a syringe plunger, e.g., a thumb press, a plunger rod, and a stopper that fits tightly within the first and/or second fluid reservoir portion. The thumb press can be used to pull out and push in the plunger. For example, the first initiator and/or the second initiator can include a plunger with a rubber stopper portion that fits tightly in respectively the first fluid reservoir portion and/or the second fluid reservoir portion. In an aspect, the plunger is formed from glass and includes a sintered surface. For example, the first initiator and/or the second initiator can include a plunger formed from sintered glass for use with a first fluid reservoir portion and/or a second fluid reservoir portion formed from glass. In an aspect, the plunger is formed from metal. For example, the first initiator and/or the second initiator can be formed from metal, e.g., stainless steel.

In an aspect, the first initiator is a first plunger and the second initiator is a second plunger. In an aspect, the first initiator is a first plunger and the second initiator is a second plunger, the first plunger sized to fit within the first fluid reservoir portion and to induce flow of the first fluid composition, the second plunger sized to fit within the second fluid reservoir portion and to induce flow of the second fluid composition. In an aspect, the first initiator is a first plunger, the first plunger substantially ring-shaped and sized to fit in a space between a first hollow tube and a second hollow tube forming the first fluid reservoir portion, and wherein the second initiator is a second plunger, the second plunger sized to fit in a second hollow tube forming the second fluid reservoir portion. In an aspect, the first plunger and the second plunger are concentric. FIGS. 7A and 7B illustrate aspects of a first and second plunger of a penetrating device. FIG. 7A shows a schematic of a portion of a first fluid reservoir portion 700 and a second fluid reservoir portion 710 of a penetrating device. First fluid reservoir portion 700 includes the space between first hollow tube 715 and second hollow tube 720. Second fluid reservoir portion 710 includes the internal space of second hollow tube 720. First plunger 725 includes a hollow cylindrical plunger rod 730 attached at one end to cylindrical stopper 735 and at the other end to cylindrical thumb press 740, first plunger 725 disposed within first fluid reservoir portion 700 between first hollow tube 715 and second hollow tube 720, cylindrical stopper 735 including a hole 738, cylindrical thumb press 740 including a hole 742. Second plunger 745 includes a plunger rod 750 attached at one end to stopper 755 and at the other end to thumb press 760, second plunger 745 disposed within second reservoir portion 710 within second hollow tube 720, plunger rod 750 is disposed within hole 742 of cylindrical thumb press 740 and stopper 755 is configured to pass through hole 738 of cylindrical stopper 735.

In an aspect, as illustrated in FIG. 7B, the first plunger can include two or more rods disposed in the cylindrical first fluid reservoir portion, the two or more rods attached at one end to a cylindrical stopper and at the other end to a cylindrical thumb press. FIG. 7B shows a schematic of a first fluid reservoir portion 700 and a second fluid reservoir portion 710. First fluid reservoir portion 700 includes the space between first hollow tube 715 and second hollow tube 720. Second fluid reservoir portion 710 includes the internal space of second hollow tube 720. First plunger 765 includes two or more plunger rods 770 attached at one end to cylindrical stopper 735 and at the other end to cylindrical thumb press 740, first plunger 725 disposed within first fluid reservoir portion 700 between first hollow tube 715 and second hollow tube 720, cylindrical stopper 735 including a hole 738, cylindrical thumb press 740 including a hole 742; second plunger 745 includes a plunger rod 750 attached at one end to stopper 755 and at the other end to thumb press 760, second plunger 745 disposed within second reservoir portion 710 within second hollow tube 720, plunger rod 750 is disposed within hole 742 of cylindrical thumb press 740 and stopper 755 is configured to pass through hole 738 of cylindrical stopper 735.

In an aspect, at least one of the first initiator or the second initiator includes a pump. In an aspect, a first pump is configured to induce flow of the first fluid composition from the first fluid reservoir portion, through the internal fluid conduit, and out at least one of the plurality of pores. In an aspect, the second pump is configured to induce flow into or out of the second fluid reservoir portion, through the lumen defined by the second hollow cylinder. In an aspect, at least one of the first pump or the second pump includes a positive displacement pump. Non-limiting examples of positive displacement pumps include rotary pumps, e.g., gear or screw pumps, peristaltic pumps with flexible tubing, plunger pumps, compressed-air-powered double-diaphragm pumps, and centrifugal pumps. In an aspect, the pump includes a syringe pump, syringe driver, or infusion pump. In an aspect, the second pump includes an aspiration pump or a suction pump to induce flow into the second fluid reservoir portion. In an aspect, at least one of the first pump or the second pump includes a valveless pump. In an aspect, a first pump pushes on the thumb press of a first plunger and/or a second pump pushes on the thumb press of a second plunger. In an aspect, a first pump pumps a gas, e.g., air, into the first fluid reservoir portion to induce flow of the first fluid composition and a second pump pumps a gas, e.g., air, into the second fluid reservoir portion to induce flow of a second fluid composition. In an aspect, a first pump pumps the first fluid composition from the first fluid reservoir portion through the internal fluid conduit and/or the a second pump pumps a second fluid composition from the second fluid reservoir portion through the lumen defined by the second hollow cylinder of the penetrating portion. For example, a first pump can include a first peristaltic pump with tubing attached at one end to the first fluid reservoir portion and at a second end to the connector portion of the first hollow cylinder, and a second pump can include a second peristaltic pump with tubing attached at one end to the second fluid reservoir portion and at a second end to the second hollow cylinder of the penetrating portion. In an aspect, a first pump pumps the first fluid composition from the first fluid reservoir portion through the internal fluid conduit and the second pump aspirates a captured sample into the second fluid reservoir portion through the lumen defined by the second hollow cylinder.

In an aspect, the first initiator and the second initiator are operably coupled. For example, actuating, e.g., moving, the first initiator automatically actuates the second initiator. In an aspect, the thumb press of the first initiator and the thumb press of the second initiator are operably coupled. For example, the thumb press of the first initiator can be physically attached to the thumb press of the second initiator such that moving the first initiator automatically causes movement of the second initiator and moving the second initiator automatically causes movement of the first initiator. For example, a first pump, e.g., an electric pump, can be operably coupled to a second pump such that actuating, e.g., turning on, the first pump actuates the second pump.

In an aspect, the first initiator and the second initiator are operably independent. In an aspect, a first plunger and a second plunger are operably independent. In an aspect, the thumb press of the first initiator and the thumb press of the second initiator are operably independent. For example, the thumb press of the first initiator can be moved independently of the thumb press of the second initiator. In an aspect, a first pump and a second pump are operably independent. For example, actuating the first pump does not automatically actuate the second pump.

Figure 8:
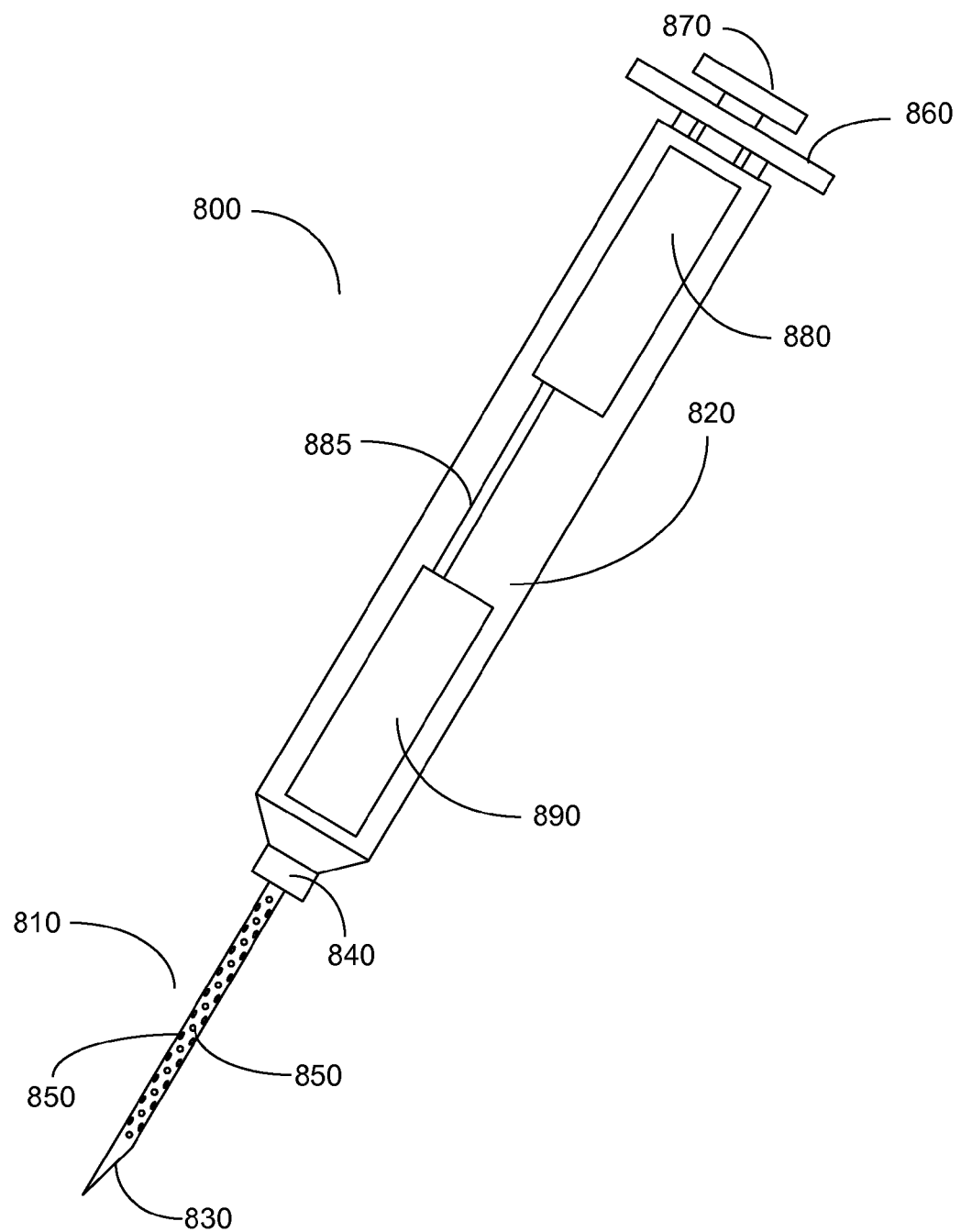
FIG. 8 shows a schematic of a penetrating device including a computing component and at least one sensor.

FIG. 8 illustrates further aspects of a penetrating device. In an aspect, penetrating device 800 includes penetrating portion 810 and reservoir portion 820. Penetrating portion 810 includes penetrating edge 830 and plurality of pores 850, connector portion 840, first initiator 860, and second initiator 870. Penetrating device 800 includes at least a portion of the internal components described in FIG. 2 for penetrating device 100, including a first fluid reservoir portion for holding a first fluid composition and associated with first initiator 860 and a second fluid reservoir portion associated with second initiator 870. In addition, penetrating device 800 includes computing component 880. Computing component 880 includes a microprocessor. In an aspect, the microprocessor includes a central processing unit (CPU) on a single integrated circuit. In an aspect, the microprocessor is programmable, including circuitry configured to accept digital data as input, process it according to instructions stored in its memory, and provide results as output.

In an aspect, computing component 880 is operably coupled to at least one of the first initiator 860 or the second initiator 870. For example, the computing component can be electrically wired to the first initiator and/or the second initiator. For example, the computing component can be electrically wired to a first spring-loaded mechanism associated with the first initiator and to a second spring-loaded mechanism associate with the second initiator. In an aspect, the computing component 880 includes circuitry configured to controllably actuate at least one of the first initiator 860 or the second initiator 870. In an aspect, the microprocessor of the computing component 880 includes one or more instructions for controllably actuating at least one of first initiator 860 or second initiator 870. In an aspect, the microprocessor of computing component 880 includes embedded software for controllably actuating at least one first initiator 860 or second initiator 870.

In an aspect, the computing component is operably coupled to a first initiator that is a first pump and/or a second initiator that is a second pump. For example, the computing component can include circuitry configured to send a signal, e.g., an electrical signal, to actuate a first and/or second pump.

In an aspect, computing component 880 includes circuitry configured to controllably actuate first initiator 860 and second initiator 870 simultaneously. In an aspect, computing component 880 includes circuitry configured to controllably actuate first initiator 860 and second initiator 870 sequentially. In an aspect, computing component 880 includes circuitry configured to controllably actuate at least one of first initiator 860 to deliver a fixed amount of the first fluid composition or second initiator 870 to deliver a fixed amount of a second fluid composition.

In an aspect, penetrating device 800 further includes at least one sensor 890 operably coupled to computing component 880. In an aspect, at least one sensor 890 is operably coupled to computing component 880 through a wired connection 885. In an aspect, at least one sensor 890 includes at least one of an accelerometer, a clock, a temperature sensor, a proximity sensor, a chemical sensor, or a pressure sensor. Non-limiting examples of other sensors include at least one of a flow sensor, a viscosity sensor, a shear sensor, a pH sensor, an optical sensor, an imaging device, an acoustic sensor, a biosensor, an electrical sensor, or a magnetic sensor. In an aspect, at least one sensor 890 is sized for attachment to penetrating device 800. In an aspect, at least one sensor 890 includes a micro-electromechanical systems (MEMS) sensor.

In an aspect, the at least one sensor 890 includes at least one accelerometer. For example, the penetrating device can include at least one sensor for tracking movement towards a target tissue, e.g., accelerometers and/or proximity sensors, to indicate when the first and/or second initiator should be actuated. For example, the at least one sensor can include at least one chip-based accelerometer, gyroscope, magnetometers, and inertia sensor commonly used in smart devices, e.g., smart phones. For example, the accelerometer can include one or more piezoelectric, piezoresistive, or capacitive components for converting mechanical motion into an electrical signal. For example, a piezoelectric accelerometer can include a piezoceramic (e.g., lead zirconate titanate) or crystals (e.g., quartz or tourmaline). For example, the accelerometer can include a micro electro-mechanical system (MEMS) including a cantilever beam. In an aspect, the accelerometer is used in combination with computing component 880 for an inertial navigation system to calculate the position, orientation, and velocity of the penetrating device. Accelerometers of various sizes and types are available from commercial sources (e.g., from Mouser Electronics®, Mansfield, Tex.).

In an aspect, at least one sensor 890 includes at least one proximity sensor. For example, the penetrating device can include a proximity sensor for sensing proximity of the penetrating edge with a surface, e.g., a tissue surface. In an aspect, the proximity sensor can include capacitive, inductive, magnetic, optical or ultrasonic sensing. Proximity sensors of various sizes and types are available from commercial sources (e.g., from Mouser Electronics®, Mansfield, Tex.).

In an aspect, at least one sensor 890 includes at least one pressure sensor. For example, the penetrating device can include a pressure sensor for sensing contact of the penetrating edge with a surface, e.g., a tissue surface. For example, a pressure sensor can be used to detect when the penetrating portion of the penetrating device comes in contact with a surface, e.g., a tissue surface. For example, the at least one pressure sensor can include a piezoresistive strain gauge. For example, the at least one pressure sensor can include a capacitive pressure sensor including a metal, ceramic, or silicon diaphragms. For example, the at least one pressure sensor can include a quartz-based piezoelectric pressure sensor. Pressure sensors of various sizes and types are available from commercial sources (e.g., from Mouser Electronics®, Mansfield, Tex.).

In an aspect, at least one sensor 890 includes at least one timer. For example, the at least one timer can be used to measure the interval between actuation of the first initiator and actuation of the second initiator, the actuation of the first and/or second initiator with respect to acceleration of device, or proximity to target. In an aspect, at least one sensor 890 includes at least one clock.

In an aspect, at least one sensor 890 includes at least one temperature sensor. For example, the penetrating device can include a temperature sensor for sensing proximity of the penetrating edge with a heated surface, e.g., a skin surface. Temperature sensors or thermostats in various sizes and types are available from commercial sources (e.g., from Mouser Electronics®, Mansfield, Tex.).

In an aspect, at least one sensor 890 includes at least one chemical sensor. For example, the penetrating device can include a chemical sensor for sensing chemicals upon contact with or penetration through a surface, e.g., chemical markers on the skin surface or in the underlying dermal layers of the skin. For example, the penetrating device can include a chemical sensor that is an "artificial nose" for sensing a gas phase analyte. In an aspect, the chemical sensor can include at least one sensor responsive to changes in capacitance. See, e.g., Berggren et al., "Capacitive Biosensors," *Electroanalysis vol.* 13, no. 3, 173-180, (2001), which is incorporated herein by reference. For example, one or more sensors can include a micromechanical biosensor with a fixed-fixed beam attached to an interdigitated capacitor (see, for example, Lim et al., "A Micromechanical Biosensor with Interdigitated Capacitor Readout," *Proceedings of the* 2011 *IEEE/ICME International Conference on Complex Medical Engineering*, May 22-25, Harbin, China, which is incorporated herein by reference). Sensors may also include nanowire nanosensors, for example as described in Cui et al., "Nanowire Nanosensors for Highly Sensitive and Selective Detection of Biological and Chemical Species," *Science*, vol. 293, 1289-1292 (2001), which is incorporated herein by reference. Sensors can include those utilizing antibodies secured to a graphene substrate. See Tehrani et al., "Detection of Monoclonal Antibodies using Chemically Modified Graphite Substances," *IEEE Sensors* 2010 *Conference Proceedings*, 428-431, (2010), which is incorporated herein by reference. In some embodiments, sensors include aptamer-modified graphene field-effect transistors, see Ohno et al., "Graphene Field-Effect Transistors for Label-Free Biological Sensors," *IEEE Sensors* 2010 *Conference Proceedings*, 903-906, (2010), which is incorporated herein by reference. A sensor can include a field effect transistor (FET), such as described in U.S. Pat. No. 7,507,675 to Zuilhof et al., titled "Device Manufacturing Method and Device," which is incorporated herein by reference. A sensor can include a nano-cantilever device, such as described in U.S. Pat. No. 7,612,424 to Espinosa and Ke, titled "Nano-electromechanical Bistable Cantilever Device," which is incorporated herein by reference.

In an aspect, computing component 880 includes circuitry configured to actuate at least one of first initiator 860 or second initiator 870 in response to input from at least one sensor 890. For example, the computing component can include circuitry configured to actuate at least one of the first initiator or the second initiator in response to input from an accelerometer measuring velocity of the device as it approaches a tissue target and from a proximity sensor measuring proximity of the device to the tissue target. For example, the computing component can include circuitry configured to actuate the first initiator just prior to contact with a tissue surface, as measured by a proximity sensor, and circuitry configured to actuate the second initiator just after piercing the tissue surface, as measured by a pressure sensor.

Figure 9:
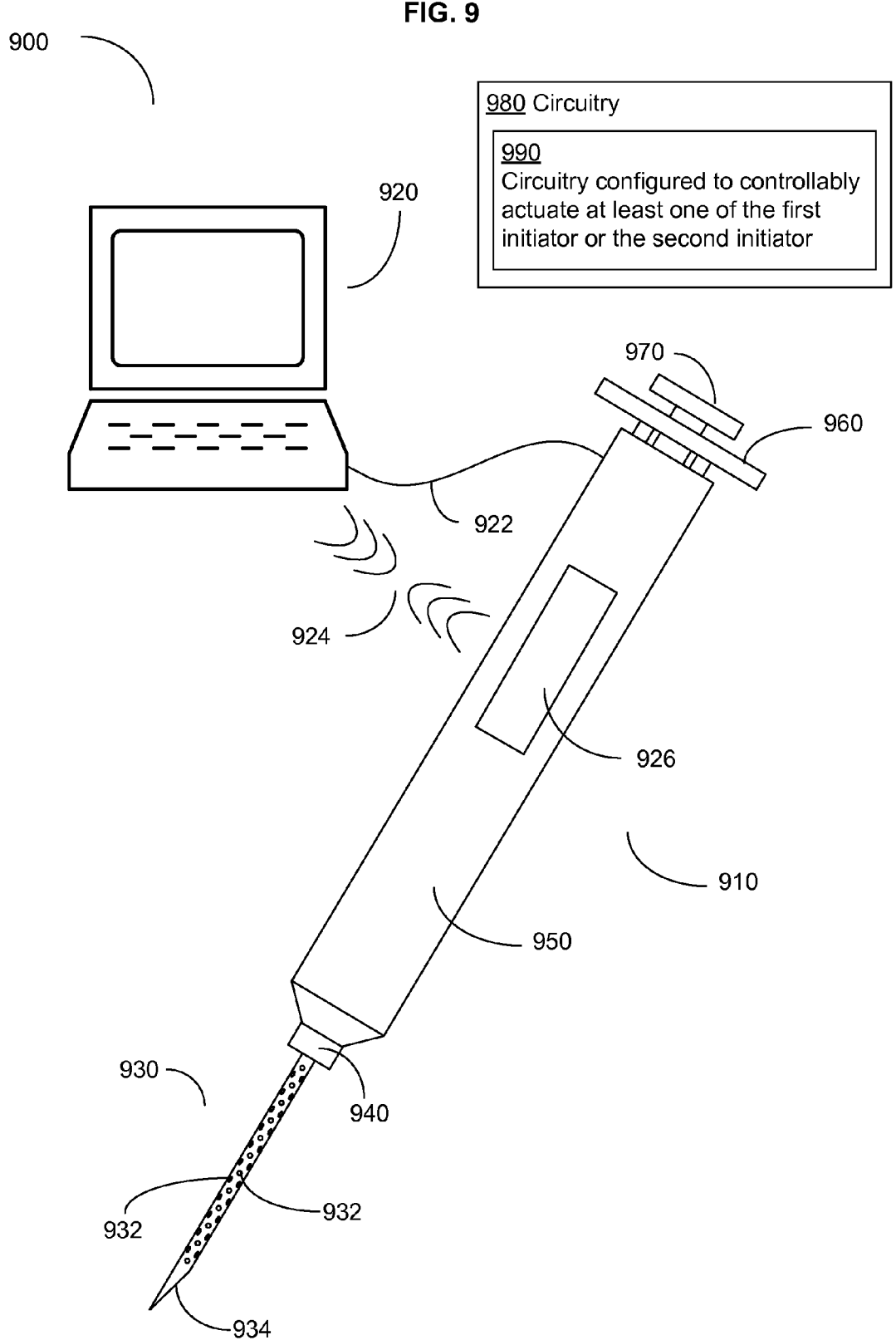
FIG. 9 shows a schematic of a penetrating system having a penetrating device and a computing device.

With reference to FIG. 9, shown is a schematic of a penetrating system. Penetrating system 900 includes penetrating device 910 and computing device 920. Penetrating device 910 includes penetrating portion 930, connector portion 940, fluid reservoir portion 950, first initiator 960, and second initiator 970. Penetrating portion 930 further includes a plurality of pores 932 and penetrating edge 934. Penetrating device 910 is operably coupled to computing device 920 through either a wired communications link 922 or a wireless communications link 924 through transmission unit 926. Computing device 920 of penetrating system 900 includes a processor and circuitry 980 including circuitry 990 configured to controllably actuate at least one of the first initiator 960 or the second initiator 970. For example, computing device 920 can include circuitry configured to send a signal to a release mechanism, e.g., a release mechanism associated with a spring, to actuate at least one of the first initiator 960 or the second initiator 970. For example, computing device 920 can include circuitry configured to send a signal to turn on or off a small motor associated with first initiator 960 or second initiator 970.

Figure 10:
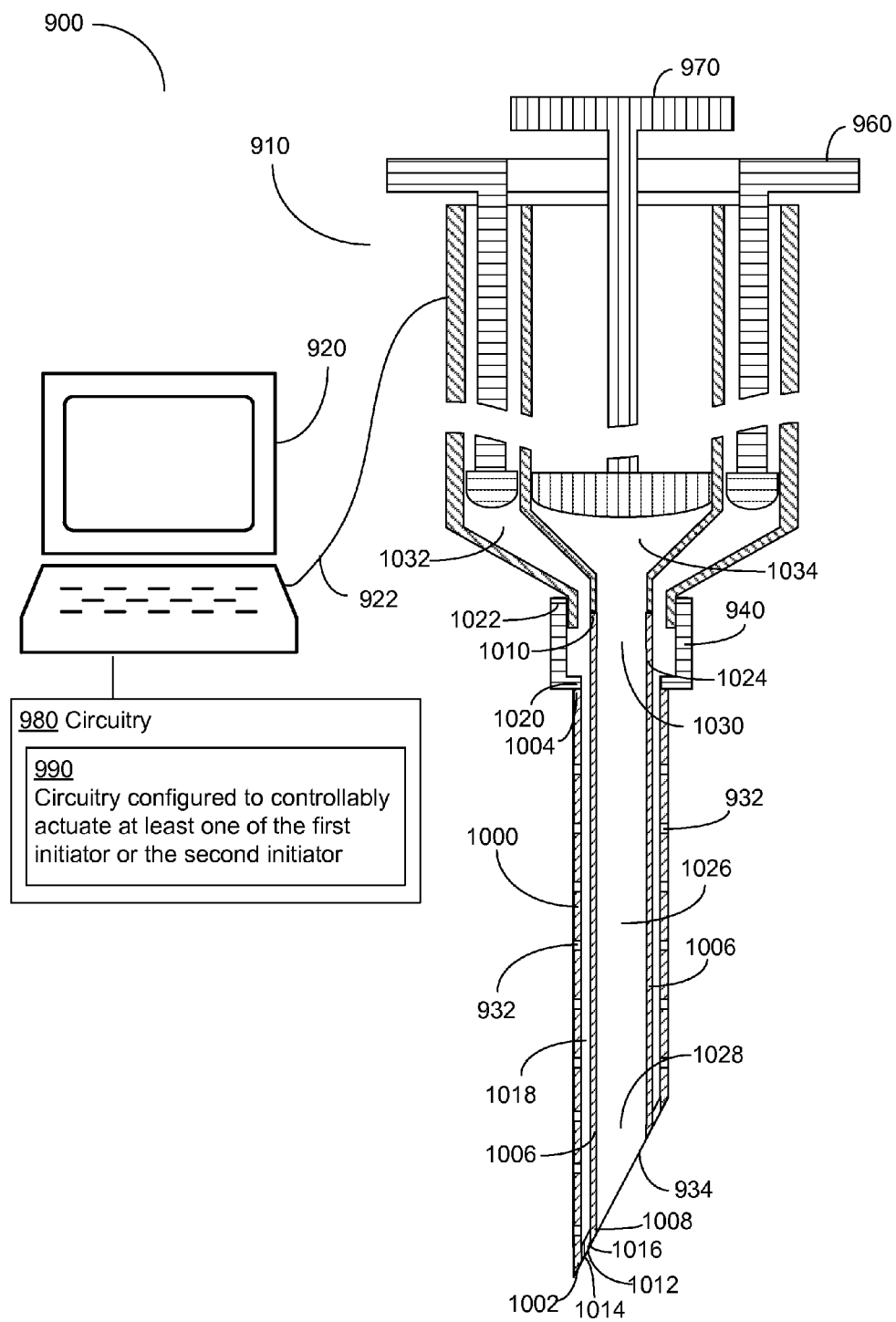
FIG. 10 shows further aspects of a penetrating system such as shown in FIG. 9.

FIG. 10 illustrates further aspects of penetrating system 900 including penetrating device 910 operably coupled to computing device 920. FIG. 10 shows a schematic of a longitudinal cross-section through penetrating device 910. Penetrating device 910 of penetrating system 900 includes a first hollow cylinder 1000 having a first end 1002 and a second end 1004, the first hollow cylinder 1000 including a plurality of pores 932. Penetrating device 910 of penetrating system 900 further includes a second hollow cylinder 1006 having a first end 1008 and a second end 1010, the second hollow cylinder 1006 disposed within the first hollow cylinder 1000 and substantially coaxial to the first hollow cylinder 1000. Penetrating device 910 of penetrating system 900 further includes a substantially ring-shaped end piece 1012 having an outer edge 1014 and an inner edge 1016, the outer edge 1014 of substantially ring-shaped end piece 1012 secured to the first end 1002 of the first hollow cylinder 1000 and the inner edge 1016 of the substantially ring-shaped end piece 1012 secured to the first end 1008 of the second hollow cylinder 1006, wherein the first hollow cylinder 1000 and the second hollow cylinder 1006 and the substantially ring-shaped end piece 1012 form penetrating edge 934. Penetrating device 910 of penetrating system 900 further includes an internal fluid conduit 1018 defined by a space between the first hollow cylinder 1000 and the substantially coaxial second hollow cylinder 1006, the internal fluid conduit 1018 in fluid communication with the plurality of pores 932 along the length of the first hollow cylinder 1000. Penetrating device 910 of penetrating system 900 includes a connector portion 940 with a first end 1020 and a second end 1022, the connector portion 940 disposed over and coaxial to a region 1024 of the second hollow cylinder 1006 proximal to the second end 1010 of the second hollow cylinder 1006, the first end 1020 of the connector portion 940 attached proximal to the second end 1004 of the first hollow cylinder 1000, the connector portion 940 in fluid communication with the internal fluid conduit 1018. Penetrating device 910 of penetrating system 900 further includes a lumen 1026 defined by the second hollow cylinder 1006, the lumen 1026 having a first end 1028 and a second end 1030, the first end 1028 of the lumen 1026 in fluid communication with the penetrating edge 934. Penetrating device 910 of penetrating system 900 includes a first fluid reservoir portion 1032 and second fluid reservoir portion 1034. A first fluid reservoir portion 1032 for holding a first fluid composition is associated with the second end 1022 of connector portion 940 and is in fluid communication with the connector portion 940 and the internal fluid conduit 1018. A second fluid reservoir portion 1034 is associated with the second end 1010 of the second hollow cylinder 1006, the second fluid reservoir portion 1034 in fluid communication with the lumen 1026 defined by the second hollow cylinder 1006. Penetrating device 910 of penetrating system 900 includes a first initiator 960 configured to induce flow of the first fluid composition from the first fluid reservoir portion 1032, through the internal fluid conduit 1018, and out at least one of the plurality of pores 932. Penetrating device 910 of penetrating system 900 includes a second initiator 970 configured to induce flow into or out of the second fluid reservoir 1034, through the lumen 1026 defined by the second hollow cylinder 1006.

In an aspect, the first hollow cylinder 1000 is formed from stainless steel. In an aspect, the first hollow cylinder 1000 is formed from at least one of metal, alloy, plastic, glass, polymer, or ceramic. In an aspect, the first hollow cylinder 1000 is formed from a porous material. In an aspect, the first hollow cylinder 1000 is formed from at least one of sintered metal particulate, glass particulate, or ceramic particulate. In an aspect, each of the plurality of pores 932 is machined into the first hollow cylinder 1000. In an aspect, each of the plurality of pores 932 is substantially perpendicular to a central axis of the first hollow cylinder 1000. Further non-limiting aspects of a first hollow cylinder have been described above herein.

In an aspect, the second hollow cylinder 1006 is formed from stainless steel. In an aspect, the second hollow cylinder 1006 is formed from at least one of metal, alloy, plastic, glass, polymer, or ceramic. In an aspect, the substantially ring-shaped end piece 1012 is formed from at least one of stainless steel, metal, alloy, plastic, glass, polymer, or ceramic. In an aspect, the second hollow cylinder 1006 and the substantially ring-shaped end piece 1012 are substantially non-porous. Further non-limiting aspects of a second hollow cylinder and/or a substantially ring-shaped end piece have been described above herein.

In an aspect, the penetrating edge 934 includes a sharp piercing edge. In an aspect, the penetrating edge 934 includes a sharp beveled edge. In an aspect, penetrating edge 934 includes at least one sharp edge able to pierce a material. In an aspect, the penetrating edge 934 includes at least one sharp edge able to pierce metal, wood, concrete, plastic, polymer, fiberglass, resin, acrylic, latex, rubber, paper, or fabric. In an aspect, the penetrating edge 934 includes at least one sharp edge able to pierce plant material. In an aspect, the penetrating edge 934 includes at least one sharp edge able to pierce a body tissue of an animal. In an aspect, the penetrating edge 934 includes at least one sharp edge able to pierce skin, endothelium, muscle, adipose, bone, cartilage, eye tissue, neural tissue, or internal organ tissue.

Penetrating device 910 includes connector portion 940 associated with first fluid reservoir portion 1032. In an aspect, connector portion 940 is directly secured to a portion of first fluid reservoir portion 1032. In an aspect, the first fluid reservoir portion 1032 is attached to the second end 1022 of the connector portion 1032. For example, a first end of first fluid reservoir portion 1032 can be secured, e.g., glued or fused, to the second end 1022 of connector portion 940. In an aspect, the connector portion 940 includes a fitting. For example, connector portion 940 can include an internal diameter sized to fit into or over a first end of the first fluid reservoir portion. In an aspect, the connector portion 940 includes a slip-tip fitting. In an aspect, the connector portion 940 includes a lock fitting. In an aspect, the lock fitting includes a screw fitting. In an aspect, the lock fitting includes a Luer lock fitting.

Penetrating device 910 further includes second fluid reservoir portion 1034 associated with the second end 1010 of second hollow cylinder 1006. In an aspect, the second fluid reservoir portion 1034 is attached to the second end 1010 of the second hollow cylinder 1006. For example, a first end of second fluid reservoir portion 1034 can be secured, e.g., glued, fused, or welded, to the second end 1010 of second hollow cylinder 1006.

In an aspect, the first fluid reservoir portion 1032 is in fluid communication with the connector portion 940 and the internal fluid conduit 1018 through a flow conduit. In an aspect, the second fluid reservoir portion 1034 is in fluid communication with the lumen 1026 defined by the second hollow cylinder 1006 through a flow conduit. In an aspect, the flow conduit includes a length of tubing, e.g., surgical tubing. See, e.g., FIGS. 6A and 6B for a non-limiting example.

In an aspect, the first fluid reservoir portion 1032 includes a first hollow tube and the second fluid reservoir portion 1034 includes a second hollow tube, the second hollow tube disposed within the first hollow tube. In an aspect, the second hollow tube of the second fluid reservoir portion 1034 is substantially coaxial to the first hollow tube of the first fluid reservoir portion 1032. In an aspect, the first fluid reservoir portion 1032 and the second fluid reservoir portion 1034 are parallel to one another. For example, the first fluid reservoir portion and the second fluid reservoir portion can be parallel and concentric as shown in FIG. 10. For example, the first fluid reservoir portion and the second fluid reservoir portion can be parallel and not concentric, a non-limiting example of which is shown in FIG. 5.

First fluid reservoir portion 1032 is configured to hold a first fluid composition. In an aspect, the first fluid composition includes at least one of an anesthetic or an analgesic. In an aspect, the first fluid composition of the first fluid reservoir portion includes at least one antiseptic. In an aspect, the first fluid composition of the first fluid reservoir portion includes at least one antimicrobial agent. In an aspect, the first fluid composition of the first fluid reservoir portion includes at least one anticoagulant. In an aspect, the first fluid composition of the first fluid reservoir portion includes at least one antihemorrhagic agent. In an aspect, the first fluid composition of the first fluid reservoir portion includes at least one treatment agent. In an aspect, the first fluid composition of the first fluid reservoir portion includes at least one lubricant. In an aspect, the first fluid composition of the first fluid reservoir portion includes at least one sealant. Non-limiting examples of anesthetics, analgesics, antiseptics, antimicrobial agents, anticoagulants, antihemorrhagic agents, treatment agents, lubricants, and sealants have been described above herein. In an aspect, the first fluid composition is incorporated into first fluid reservoir portion 1032 at the time of manufacture. In an aspect, the first fluid composition is incorporated into first fluid reservoir portion 1034 at the time of use.

In an aspect, second fluid reservoir portion 1034 is configured to hold a second fluid composition. In an aspect, the second fluid composition of the second fluid reservoir portion includes at least one vaccine. In an aspect, the second fluid composition of the second fluid reservoir portion includes at least one therapeutic agent. In an aspect, the at least one therapeutic agent includes at least one of an anti-inflammatory agent, an antimicrobial agent, a chemotherapeutic agent, or a diabetes agent. In an aspect, the second fluid composition of the second fluid reservoir portion includes a dye. In an aspect, the second fluid composition of the second fluid reservoir portion includes a wash solution.

In an aspect, the second fluid composition of the second fluid reservoir portion 1034 is configured for at least one of percutaneous administration, intravenous administration, subcutaneous administration, intraocular administration, intraosseus administration, epidural administration, intraarticular administration, intraperitoneal administration, intraoral administration, or intramuscular administration. Non-limiting examples of vaccines and therapeutic agents have been described above herein. In an aspect, the second fluid composition is incorporated into the second fluid reservoir portion 1034 at the time of manufacture. In an aspect, the second fluid composition is incorporated into the second fluid reservoir portion 1034 at the time of use.

In an aspect, the second fluid reservoir portion 1034 is configured to hold a captured sample, e.g., a biopsy sample. In an aspect, the captured sample includes a blood sample, bone marrow sample, tissue sample, lavage sample, or other sample captured from an animal subject. In an aspect, the captured sample includes a sample taken from a plant, e.g., a tree.

The penetrating device of system 900 includes first initiator 960 and second initiator 970. In an aspect, at least one of the first initiator 960 or the second initiator 970 includes a plunger. In an aspect, the first initiator 960 includes a first plunger and the second initiator 970 includes a second plunger. In an aspect the first plunger and the second plunger are concentric. See, e.g., FIGS. 7A and 7B. In an aspect, the first initiator 960 is a first plunger and the second initiator 970 is a second plunger, the first plunger sized to fit within the first fluid reservoir portion 1032 and to induce flow of the first fluid composition, the second plunger sized to fit within the second fluid reservoir portion 1034 and to induce flow into or out of the second fluid reservoir portion 1034. In an aspect, the first initiator 960 is a first plunger, the first plunger substantially ring-shaped and sized to fit in a space between a first hollow tube and a second hollow tube forming the first fluid reservoir portion 1032, and wherein the second initiator 970 is a second plunger, the second plunger sized to fit in the second hollow tube forming the second fluid reservoir portion 1034. Non-limiting aspects of penetrating devices including plungers have been described above herein.

In an aspect, at least one of the first initiator 960 or the second initiator 970 includes a pump. In aspect, the system includes at least one peristaltic pump connected to at least one of the first fluid reservoir portion or the second fluid reservoir portion. In an aspect, the system includes a first pump for actuating a thumb press of a first plunger and a second pump for actuating a thumb press of a second plunger. For example, the system can include a syringe pump or infusion pump into which the penetrating device including a first plunger and a second plunger is inserted, the syringe pump operably coupled to the computing device of the system to control actuation of the first and second plungers of the penetrating device.

In an aspect, at least one of the first initiator 960 or the second initiator 970 includes a valve. For example, a first valve and/or a second valve can be opened or closed to control flow of the first fluid composition and/or a second fluid composition. In an aspect, a first valve and a second valve are operably coupled and controllably actuated by computing device 920. In an aspect, a first valve and a second valve are operably independent and independently actuated by computing device 920.

In an aspect, the first initiator 960 and the second initiator 970 are operably coupled. For example, actuation, e.g., movement, of first initiator 960 causes actuation of second initiator 970. In an aspect, the first initiator 960 and the second initiator 970 are operably independent. For example, operation of first initiator 960 is independent of second initiator 970.

In an aspect, the computing device 920 and the penetrating device 910 are operably connected through a wired communication link 922. For example, the computing device may be linked to the penetrating device through a cable, e.g., a universal serial bus (USB) cable.

Figure 11:
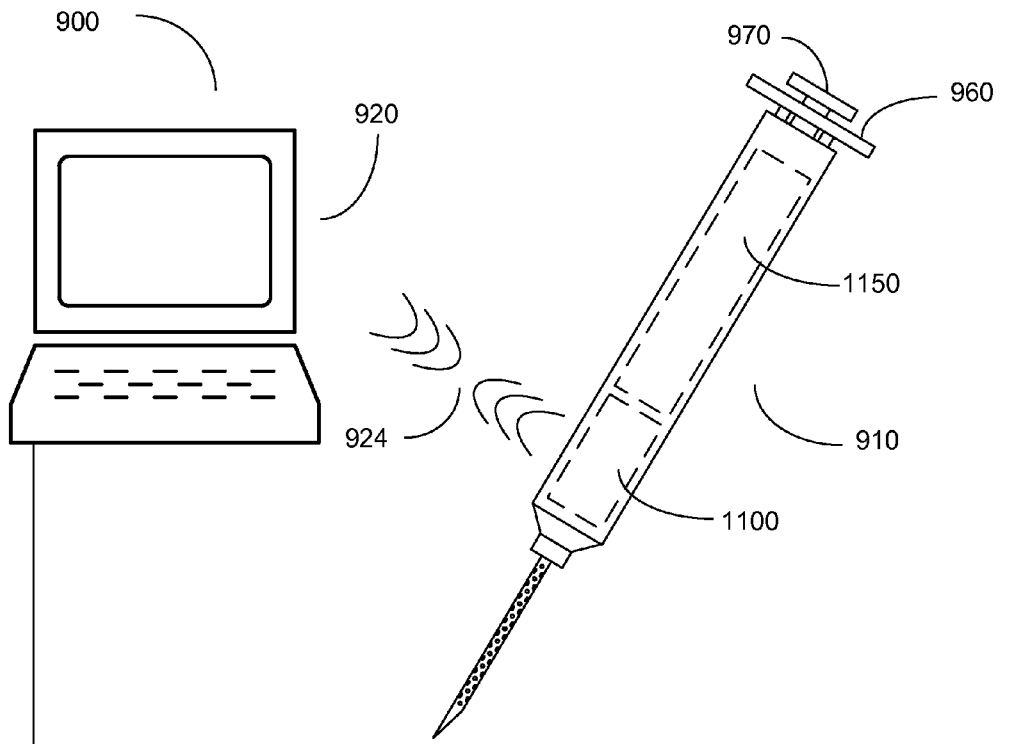
FIG. 11 shows a schematic of a penetrating system including a first and second pump.

FIG. 11 shows further aspects of penetrating system 900. Penetrating system 900 includes penetrating device 910 and computing device 920. In an aspect, the computing device 920 is operably coupled to the penetrating device 910 through a wireless communication link 924 mediated by transmission unit 1100.

In an aspect, the penetrating device 910 includes a transmission unit 1100 including an antenna. A "transmission unit," as used herein, can be one or more of a variety of units that are configured to send and/or receive signals, such as signals carried as electromagnetic waves. A transmission unit generally includes at least one antenna and associated circuitry. A transmission unit can include a transmitter and a receiver. A transmission unit can include volatile or non-volatile memory. A transmission unit can include a processor and/or be operably connected to a processor. A transmission unit can be operably connected to an energy source, such as a battery. A transmission unit can include an energy harvesting unit, such as a unit configured to obtain energy from electromagnetic waves. A transmission unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmission unit can include an oscillator and encoder configured to generate a programmable pulse position-modulated signal in the radio frequency range (see, e.g., U.S. Pat. No. 4,384,288, which is incorporated herein by reference). A transmission unit can include a radio frequency identification device (RFID), which can be a passive RFID device, a semi-passive RFID device, or an active RFID device, depending on the embodiment (see, e.g., Chawla & Ha, "An Overview of Passive RFID," *IEEE Applications and Practice*, 11-17 (September 2007), which is incorporated herein by reference). A transmission unit including an RFID device can be configured to transmit signals in the UHF standard range. A transmission unit can include a battery-assisted passive RFID device, such as sold by Alien Technology®, Morgan Hill, Calif. A transmission unit can include an optical transmission unit. A transmission unit can include a hybrid backscatter system configured to function in an RFID, IEEE 802.11x standard and Bluetooth system (see, e.g., U.S. Pat. No. 7,215,976, which is incorporated herein by reference). A transmission unit can include a near field communication (NFC) device. A transmission unit can include a Wireless Identification and Sensing Platform (WISP) device.

Computing device 920 of penetrating system 900 includes a microprocessor and circuitry 980. Circuitry 980 further includes circuitry 990 configured to controllably actuate at least one of first initiator 960 or second initiator 970. In an aspect, the computing device 920 includes circuitry 1110 configured to controllably actuate the first initiator 960 and the second initiator 970 simultaneously. For example, the computing device can include circuitry configured to send signals simultaneously to the first and second initiators to simultaneously actuate, e.g., initiate movement of, the first and second initiators. For example, flow of the first fluid composition from the first fluid reservoir portion and flow into or out of the second fluid reservoir portion can be simultaneously initiated. In an aspect, computing device 920 includes circuitry 1120 configured to controllably actuate the first initiator 960 and the second initiator 970 sequentially. For example, the computing device can include circuitry configured to send sequential signals to the first and second initiators to sequentially actuate, e.g., initiate movement of, the first and second initiators. For example, a dosing protocol may include administering a first fluid composition, e.g., an analgesic such as lidocaine, as the penetrating portion is entering the skin followed by administering a second fluid composition, a therapeutic agent. In an aspect, computing device 920 includes circuitry 1130 configured to controllably actuate at least one of the first initiator 960 to deliver a fixed amount of the first fluid composition or the second initiator 970 to deliver a fixed amount of the second fluid composition. For example, the computing device can include a user interface, e.g., a keyboard and display, for entering dosing information. In an aspect, computing device 920 includes circuitry 1140 configured to controllably actuate at least one of the first initiator 960 to deliver the first fluid composition or the second initiator 970 to deliver the second fluid composition based on time from entering an injection site. For example, the first initiator may be actuated as the penetrating edge of the penetrating device touches the skin surface and the second initiator may be actuated at a subsequent time point, e.g., milliseconds or microseconds later.

In an aspect, computing device 920 includes circuitry configured to execute one or more instructions for controlling actuation of the first and second initiators. In an aspect, the computing device includes circuitry configured to execute one or more instructions for controllably actuating at least one of the first initiator or the second initiator. In an aspect, the computing device includes circuitry configured to execute one or more instructions for controllably actuating the first initiator and the second initiator simultaneously. In an aspect, the computing device includes circuitry configured to execute one or more instructions for controllably actuating the first initiator and the second initiator sequentially. In an aspect, the computing device includes circuitry configured to execute one or more instructions for controllably actuating at least one of the first initiator to deliver a fixed amount of the first fluid composition or the second initiator to deliver a fixed amount of a second fluid composition. In an aspect, the computing device includes circuitry configured to execute one or more instructions for controllably actuating at least one of the first initiator to deliver the first fluid composition or the second initiator to deliver the second fluid composition based on time from entering an injection site.

In an aspect, the computing device includes a processor, e.g., a central processing unit, for controlling one or more functions of the penetrating device or other peripheral components, e.g., pumps. The computing device further includes a system memory and a system bus that couples various system components including the system memory to the processor. The processor can include a microprocessor, a processing unit, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an aspect, the computing component includes one or more ASICs having a plurality of pre-defined logic components. In an aspect, the computing device includes one or more FPGA having a plurality of programmable logic commands.

In an aspect, the computing device is operably coupled to one or more input/output components. In an aspect, the one or more input/output components include the penetrating device. In an aspect, the one or more input/output components include one or more pumps. In an aspect, the one or more input/output components include one or more user interface components. Non-limiting examples of user interface components include a display, touchscreen, keyboard, keypad, microphone, speaker, mouse, joystick, stylus pen, dial, buttons, switches, or printer. In an aspect, the one or more input/output components are connected to the processor of the computing device through one or more user input interfaces that are coupled to the system bus, but may be connected by other interfaces and bus structures, such as a parallel port, game port, or a universal serial bus (USB). For example, external input components or output components may be connected to the processor through a USB port. For example, the penetrating device may be connected to the processor through a USB port. The computing device may further include or be capable of connecting to a flash card memory or other portable data storage device. The computing device may further include or be capable of connecting with a network through a network port and network interface, and through wireless port and corresponding wireless interface may be provided to facilitate communication with other peripheral devices, for example, a smart phone, a computer, a display monitor, and/or a printer. For example, the computing device can include a wireless interface to facilitate wireless communication with the transmission unit of the penetrating fluid deliver device.

In an aspect, the computing device includes image-based applications such as viewers and/or toolkits (e.g., Insight Segmentation and Registration Toolkit (ITK)). In an aspect, image segmentation or other image analysis algorithms may allow processing of images received from the at least one sensor associated with the penetrating device.

The computing device further includes a memory component. The memory component can include memory chips, e.g., ROM or flash memory chips, for providing storage of operating systems, look-up tables, references datasets, and algorithms for controllably actuating the first and second initiators of the penetrating device. The memory component of the computing device may include read-only memory (ROM) and random access memory (RAM). A number of program modules may be stored in the ROM or RAM, including an operating system, one or more application programs, other program modules and program data.

The computing device includes computer-readable media products and may include any media that can be accessed by the computing device including both volatile and nonvolatile media, removable and non-removable media. By way of example, and not of limitation, computer-readable media may include non-transitory signal-bearing media. Non-limiting examples of non-transitory signal-bearing media include a recordable type medium such as magnetic tape, a hard disk drive, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, flash memory, magnetic tape, MINIDISC, non-volatile memory card, EEPROM, optical disk, optical storage, RAM, ROM, system memory, web server, cloud, or the like. By way of example, and not of limitation, computer-readable media may include computer storage media, e.g., magnetic tape, magnetic disk storage, optical disk storage, memory cards, flash memory cards, electrically erasable programmable read-only memory (EEPROM), solid state RAM, and solid state ROM or any other medium which can be used to store the desired information and which can be accessed by the computing component. By way of further example, and not of limitation, computer-readable media may include a communication media, e.g., wired media, such as a wired network and a direct-wired connection, and wireless media such as acoustic, RF, optical, and infrared media.

In an aspect, system 900 further includes at least one sensor. In an aspect, the at least one sensor is a standalone sensor that monitors the use of penetrating device 910, e.g., an image capture device operably coupled to computing device 920. In an aspect, the at least one sensor is incorporated into penetrating device 910, e.g., sensor 1150. In an aspect, at least one sensor 1150 is operably coupled to computing device 920. In an aspect, at least one sensor 1150 is operably coupled to computing device 920 through a wireless communications link 924 via transmission unit 1100. In an aspect, at least one sensor 1150 is operably coupled to computing device 920 through a wired communications link. In an aspect, computing device 920 includes circuitry configured to actuate at least one of the first initiator 960 or the second initiator 970 in response to input from the at least one sensor 1150.

In an aspect, at least one sensor 1150 includes at least one accelerometer. For example, the accelerometer can include one or more piezoelectric, piezoresistive, or capacitive components for converting mechanical motion into an electrical signal. In an aspect, the accelerometer is used in combination with computing device 920 for an inertial navigation system to calculate the position, orientation, and velocity of the penetrating device. In an aspect, at least one sensor 1150 includes at least one proximity sensor. In an aspect, the at least one sensor 1150 includes at least one clock. In an aspect, at least one sensor 1150 includes at least one timer. In an aspect, the at least one sensor 1150 includes at least one pressure sensor. For example, a pressure sensor can be used to detect when the penetrating portion of the penetrating device comes in contact with a surface, e.g., a tissue surface. For example, the at least one pressure sensor can include a piezoresistive strain gauge. In an aspect, the at least one sensor 1150 includes at least one temperature sensor. For example, a temperature sensor can be used to detect when the penetrating portion of the penetrating device comes near or in contact with a heated surface, e.g., the surface of the skin. In an aspect, the at least one sensor 1150 includes at least one chemical sensor. Non-limiting examples of sensors have been described above herein.

Figure 12:
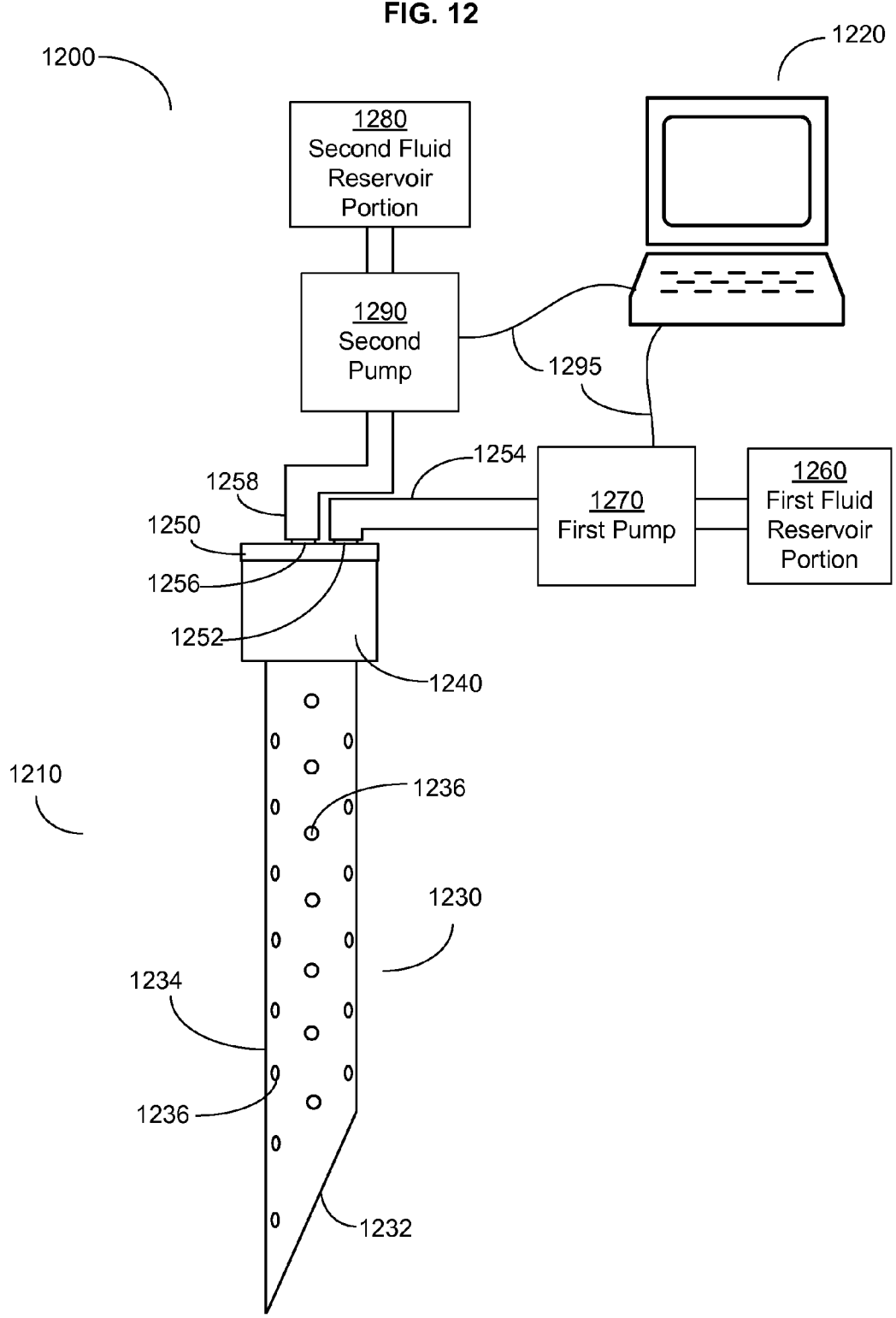
FIG. 12 shows further aspects of a penetrating system such as shown in FIG. 9.

FIG. 12 illustrates aspects of a penetrating system including at least one pump for inducing flow of the first and/or second fluid composition through the penetrating device. System 1200 includes penetrating device 1210 and computing device 1220. Penetrating device 1210 includes penetrating portion 1230 and connector portion 1240. Penetrating portion 1230 includes penetrating edge 1232, first hollow cylinder 1234, and a plurality of pores 1236. Internally, penetrating device 1210 includes a second hollow cylinder disposed within first hollow cylinder 1234, a substantially ring-shaped end piece attached to the first ends of the first and second hollow cylinders, an internal fluid conduit defined by the space between first hollow cylinder 1234 and the second hollow cylinder, and a lumen defined by the second hollow cylinder. Connector portion 1240 includes lid portion 1250. Lid portion 1250 includes first inlet 1252 in fluid communication with connector portion 1240, the internal flow conduit defined by the space between first hollow cylinder 1234 and the second hollow cylinder disposed within first hollow cylinder 1234, and at least one of the plurality of pores 1236. First inlet 1252 includes tubing 1254 attached to first fluid reservoir portion 1260 through first pump 1270. First pump 1270 controllably induces flow of a first fluid composition from first fluid reservoir portion 1260 through tubing 1254, inlet 1252, connector portion 1240, the internal flow conduit, and out at least one of the plurality of pores 1236. Lid portion 1250 further includes second inlet 1256 in fluid communication with the lumen defined by the second hollow cylinder. Second inlet 1256 includes tubing 1258 attached to second fluid reservoir portion 1280 through second pump 1290. Second pump 1290 controllably induces flow into or out of second fluid reservoir portion 1280 through a path defined by tubing 1258, inlet 1256, the lumen defined by the second hollow cylinder, and penetrating edge 1232. In an aspect first pump 1270 and second pump 1290 are separate pumps. In an aspect, first pump 1270 is an infusion pump and second pump 1290 is an aspiration pump. In an aspect first pump 1270 and second pump 1290 are part of the same pump system, e.g., a dual head or multichannel peristaltic pump. Non-limiting aspects of pumps have been described above herein. In an aspect, computing device 1220 is incorporated into a dual head or multichannel peristaltic pump including first pump 1270 and second pump 1290. In an aspect, first pump 1270 and/or second pump 1290 are situated upstream of first fluid reservoir portion 1260 and/or second fluid reservoir portion 1280, respectively. For example, the first and/or second pump can include a pump that pushes fluid out of the first and/or second fluid reservoir portion.

First pump 1270 and second pump 1290 are operably coupled to computing device 1220 through communication link 1295. Computing device 1220 includes circuitry configured to controllably actuate at least one of first pump 1270 or second pump 1290. In an aspect, computing device 1220 includes circuitry configured to actuate first pump 1270 and second pump 1290 simultaneously. In an aspect, computing device 1220 includes circuitry configured to actuate first pump 1270 and second pump 1290 sequentially. In an aspect, computing device 1220 includes circuitry configured to controllably actuate at least one of first pump 1270 to deliver a fixed amount of the first fluid composition or second pump 1290 to deliver a fixed amount of a second fluid composition. In an aspect, computing device 1220 includes circuitry configured to controllably actuate at least one of first pump 1270 to deliver the first fluid composition or second pump 1290 to deliver a second fluid composition based on time from entering an injection site.

In an aspect, the penetrating system further includes a needle actuation mechanism including at least one of a deployment mode and a retraction mode. For example, the penetrating device of the system can include a needle actuation mechanism for deploying the penetrating portion of the device just prior to piercing a surface and/or for retracting the penetrating portion following delivery of the second fluid composition or aspiration of a captured sample. In an aspect, the needle actuation mechanism includes a spring-loaded mechanism with tension and manual release. See, e.g., U.S. Pat. No. 7,744,582 to Sadowski et al. titled "Needle Assisted Jet Injector," which is incorporated herein by reference. In an aspect, the needle actuation mechanism includes use of a shape memory alloy. For example, the needle actuation mechanism can include a penetrating portion formed from shape memory alloy nickel titanium, which by changing shape is both deployable and retractable. See, e.g., U.S. Pat. No. 6,605,067 to Larsen titled "Injection Needle," which is incorporated herein by reference. In an aspect, the needle actuation mechanism is manually activated. For example, a coiled spring associated with deploying the penetrating portion can be actuated by pushing a button or flipping a switch that mechanically releases the spring-loaded penetrating portion. In an aspect, the needle actuation mechanism includes an ejection force controlled by electronics. See, e.g., U.S. Patent Application No. 2007/0197968 to Pongpairochana et al. titled "Hand-Held Electronically Controlled Injection Device for Injecting Liquid Medications," which is incorporated herein by reference. For example, the penetrating portion of the penetrating device can be associated with a piston that electronically ejects and/or retracts the penetrating portion. In an aspect, the computing device of the system includes circuitry configured to control the needle actuation mechanism. In an aspect, the computing device of the system includes circuitry configured to control speed of needle deployment. In an aspect, the needle actuation mechanism can include active refraction, e.g., wherein when the second initiator, e.g., plunger, is pressed to expel contents of the second reservoir portion, the base of the plunger attaches to the needle. Pulling back on the plunger causes the needle to retract into the barrel of the syringe. In an aspect, the needle actuation mechanism includes passive retraction. For example, contacting the plunger to the base of the syringe at the completion of injection triggers a spring mechanism which automatically retracts the penetrating needle portion. See, e.g., U.S. Pat. No. 6,572,584 to Shaw et al titled "Retractable Syringe with Reduce Retraction Force," which is incorporated herein by reference. For example, the penetrating portion can be fully fused to the syringe and spring-loaded such that the penetrating portion retracts into the barrel of the syringe when the plunger is completely depressed after the injection is given. In an aspect, the force associated with deploying the penetrating portion is sufficient to expel the first fluid composition from the first fluid reservoir portion and out at least one of the plurality of pores.

Figure 13A:
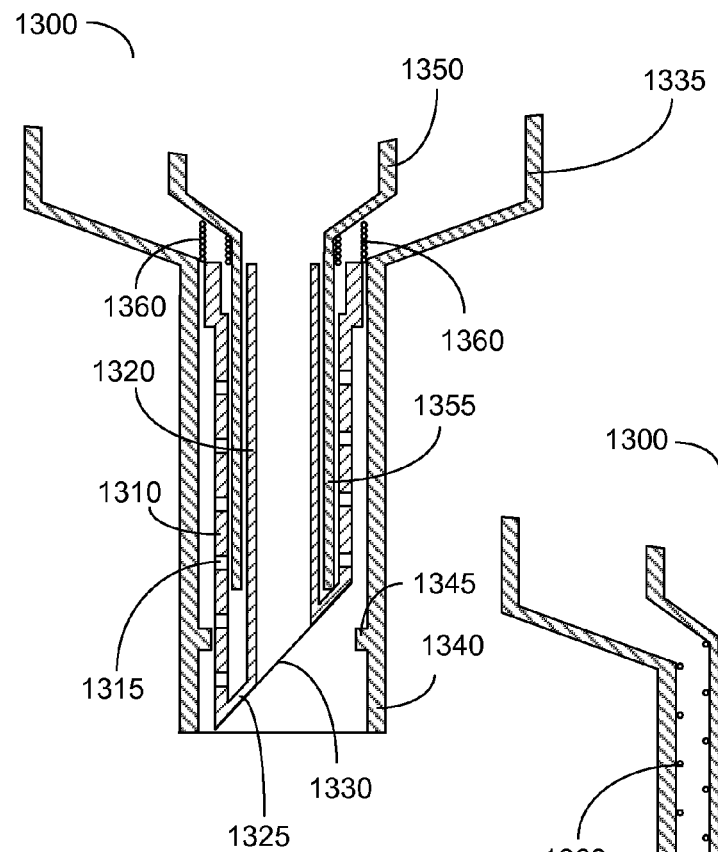
FIG. 13A shows a schematic of a longitudinal cross-section through a penetrating device including a needle actuation mechanism in a retracted state.
Figure 13B:
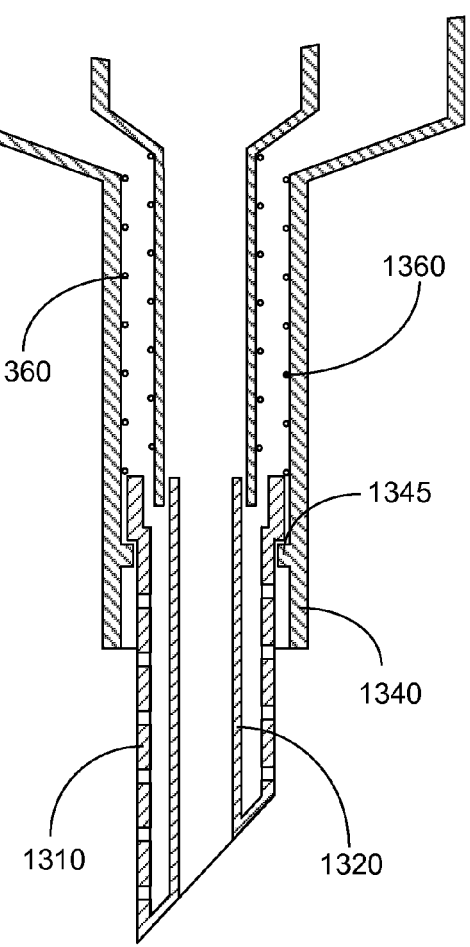
FIG. 13B shows a schematic of a longitudinal cross-section through a penetrating device including a needle actuation mechanism in a deployed state.

FIGS. 13A and 13B illustrates aspects of a penetrating device including a needle actuation mechanism. FIG. 13A is a longitudinal cross-section through a portion of penetrating device 1300 and shows the penetrating portion of the device in a refracted state. Penetrating device 1300 includes first hollow cylinder 1310 including a plurality of pores 1315. Penetrating device 1300 further includes second hollow cylinder 1320 disposed within and substantially coaxial to first hollow cylinder 1310. First hollow cylinder 1310 and second hollow cylinder 1320 are attached to substantially ring-shaped end piece 1325 to form penetrating edge 1330. Penetrating device 1300 further includes first fluid reservoir portion 1335 including first extension 1340 and stop portion 1345. First hollow cylinder 1310 is disposed within first extension 1340 of first fluid reservoir portion 1335. Penetrating device 1300 includes second fluid reservoir portion 1350 including second extension 1355. In the refracted state shown in FIG. 13A, second extension 1355 is disposed within the space between first hollow cylinder 1310 and second hollow cylinder 1320. Penetrating device 1300 further includes spring 1360. In FIG. 13A, spring 1360 is in a compressed form and first hollow cylinder 1310 and second hollow cylinder 1320 are completely refracted within first extension 1340. FIG. 13B is a longitudinal cross-section through a portion of penetrating device 1300 and shows the penetrating portion of the device in a deployed state. Spring 1360 has been actuated and is in a relaxed state. The penetrating portion including first hollow cylinder 1310 and second hollow cylinder 1320 are shown deployed beyond the end of first extension 1340. Stop portion 1345 limits the degree to which the penetrating portion can be deployed.

In an aspect, the computing device of the system includes circuitry configured to actuate a needle actuation mechanism in response to input from the at least one sensor. For example, the computing device can include circuitry configured to actuate the needle actuation mechanism to deploy the penetrating portion in response to input from a proximity sensor indicating proximity of the target tissue. For example, the computing device can include circuitry configured to actuate the needle actuation mechanism to retract the penetrating portion in response to input from a pressure sensor indicating cessation of pressure on a second initiator, e.g., a plunger, at completion of injecting a vaccine and/or therapeutic agent.

With reference to FIGS. 14A and 14B, shown are aspects of a penetrating device. FIG. 14A shows a schematic of an external view of penetrating device 1400. Penetrating device 1400 includes penetrating portion 1410 and connector portion 1420. Penetrating portion 1410 includes penetrating edge 1412 and a plurality of pores 1414. FIG. 14B shows a schematic of a longitudinal cross-section through penetrating device 1400. Penetrating device 1400 includes a first hollow cylinder 1430 having a first end 1432 and a second end 1434, the first hollow cylinder 1430 including a plurality of pores 1414, the second end 1434 of the first hollow cylinder 1430 having a connector portion 1420. Penetrating device 1400 includes a second hollow cylinder 1436 having a first end 1438 and a second end 1440, the second hollow cylinder 1436 disposed within the first hollow cylinder 1430 and substantially coaxial to the first hollow cylinder 1430. Penetrating device 1400 includes a substantially ring-shaped first end piece 1442 having an outer edge 1444 and an inner edge 1446, the outer edge 1444 of the substantially ring-shaped first end piece 1442 secured to the first end 1432 of the first hollow cylinder 1430 and the inner edge 1446 of the substantially ring-shaped first end piece 1442 secured to the first end 1438 of the second hollow cylinder 1436, wherein the first hollow cylinder 1430, the second hollow cylinder 1436, and the substantially ring-shaped first end piece 1442 form a penetrating edge 1412. Penetrating device 1400 includes a substantially ring-shaped second end piece 1448 having an outer edge 1450 and an inner edge 1452, the outer edge 1450 of the substantially ring-shaped second end piece 1448 adjacent to a portion of the first hollow cylinder 1430 proximal to the second end 1434 of the first hollow cylinder 1430 and the inner edge 1452 of the substantially ring-shaped second end piece 1448 adjacent to a portion of the second hollow cylinder 1436 proximal to the second end 1440 of the second hollow cylinder 1436, the substantially ring-shaped second end piece 1448 forming a deformable barrier. Penetrating device 1400 includes a fluid reservoir portion 1454 for holding a fluid composition, the fluid reservoir portion 1454 defined by the first hollow cylinder 1430, the second hollow cylinder 1436, the substantially ring-shaped first end piece 1442, and the substantially ring-shaped second end piece 1448, the fluid reservoir portion 1454 in fluid communication with the plurality of pores 1414. Penetrating device 1400 includes a lumen 1456 defined by the second hollow cylinder 1436, the lumen 1456 having a first end 1458 and a second end 1460, the first end 1458 of the lumen 1456 in fluid communication with the penetrating edge 1412.

Penetrating device 1400 includes a first hollow cylinder 1430. In an aspect, the first hollow cylinder 1430 is formed from stainless steel. In an aspect, the first hollow cylinder 1430 is formed from at least one of metal, alloy, plastic, glass, polymer, or ceramic. In an aspect, the first hollow cylinder 1430 is formed from a porous material. In an aspect, the first hollow cylinder 1430 is formed from at least one of sintered metal particulate, glass particulate, or ceramic particulate. Non-limiting aspects of forming a first hollow cylinder have been described above herein.

First hollow cylinder 1430 includes a plurality of pores 1414. In an aspect each of the plurality of pores is substantially perpendicular to a central axis of the first hollow cylinder. In an aspect, each of the plurality of pores is oriented at 90 degrees relative to the central axis of the first hollow cylinder. In an aspect, each of the plurality of pores is oriented at 45 degrees relative to the central axis of the first hollow cylinder. In an aspect, each of the plurality of pores is oriented at about 90 degrees to about 20 degrees relative to the central axis of the first hollow cylinder. For example, each of the plurality of pores can be oriented at 90 degrees, 85 degrees, 80 degrees, 75 degrees, 70 degrees, 65 degrees, 60 degrees, 55 degrees, 50 degrees, 45 degrees, 40 degrees, 35 degrees, 30 degrees, 25 degrees, or 20 degrees relative to the central axis of the first hollow cylinder. In an aspect, each of the plurality of pores is at substantially the same angle relative to the central axis of the first hollow cylinder. For example, each of the plurality of pores can be machined at a substantially 90 degrees relative to the central axis of the first hollow cylinder 1430. In an aspect, one or more of the plurality of pores are at different angles relative to the central axis of the first hollow cylinder 1430. For example, a first hollow cylinder manufactured from a porous material, e.g., porous ceramic, may have pores angled at varied degrees relative to the central axis of the first hollow cylinder.

In an aspect, the plurality of pores includes at least two pores. In an aspect, the plurality of pores includes 2 pores to about 100 pores. For example, the plurality of pores can include 2 pores, 3 pores, 4 pores, 5 pores, 6 pores, 7 pores, 8 pores, 9 pores, 10 pores, 15 pores, 20 pores, 25 pores, 30 pores, 35 pores, 40 pores, 45 pores, 50 pores, 55 pores, 60 pores, 65 pores, 70 pores, 75 pores, 80 pores, 85 pores, 90 pores, 95 pores, or 100 pores. In an aspect, the plurality of pores includes about 100 pores to about 100,000 pores. In an aspect, the plurality of pores includes over 100,000 pores. In an aspect, the number of pores is dependent upon the manufacturing process. For example, forming the plurality of pores by manufacturing first hollow cylinder 1430 from a porous material may include substantially more pores than forming the plurality of pores by machining the pores into the first hollow cylinder.

In an aspect, the plurality of pores is distributed over the entirety of the first hollow cylinder 1430. In an aspect, the plurality of pores is distributed over a portion of the first hollow cylinder 1430. For example, the plurality of pores can be distributed towards the first end of the first hollow cylinder. For example, the plurality of pores can be distributed towards the second end of the first hollow cylinder. For example, the plurality of pores can be concentrated to side of the first hollow cylinder.

In an aspect, the plurality of pores includes pores of at least one first size and pores of at least one second size. The plurality of pores of the first size may be distributed in a first location along the length of the first hollow cylinder and the plurality of pores of the second size may be distributed in a second location along the length of the first hollow cylinder. In an aspect, the plurality of pores include at least one first set of pores at a first angle relative to the central axis of the first hollow cylinder and at least one second set of pores at a second angle relative to the central axis of the first hollow cylinder. The plurality of pores at the first angle may be distributed in a first location along the length of the first hollow cylinder and the plurality of pores at the second angle may be distributed in a second location along the length of the first hollow cylinder.

In an aspect, each of the plurality of pores is machined into the first hollow cylinder. In an aspect, each of the plurality of pores is machined into the first hollow cylinder with a drill. In an aspect, each of the plurality of pores is machined into the first hollow cylinder using pins and/or needles. For example, the plurality of pores can be machined into the first hollow cylinder using a rotary pinned perforation roller with either cold or hot pins. In an aspect, each of the plurality of pores is machined into the first hollow cylinder with a laser. Non-limiting examples of lasers for laser cutting and/or boring include $CO_2$ lasers, neodymium (Nd) lasers, or neodymium yttrium-aluminum-garnet (Nd-YAG) lasers. In an aspect, each of the plurality of pores is machined into the first hollow cylinder using a waterjet cutter. For example, each of the plurality of pores can be machined into the first hollow cylinder using a waterjet cutter with or without an added abrasive, e.g., garnet or aluminum oxide.

First hollow cylinder 1430 further includes connector portion 1420. In an aspect, the connector portion 1420 of the second end 1434 of the first hollow cylinder 1430 is configured to connect to a second fluid reservoir portion. In an aspect, the second fluid reservoir portion includes a syringe. For example, the connector portion can be configured to connect to a 1 milliliter syringe. In an aspect, the syringe can include any of a number of standard syringes used for injection of vaccines and/or therapeutic agents. In an aspect, the syringe can include any of a number of standard syringes used for general blood draw. In an aspect, the syringe can include any of a number of standard syringes used for general aspiration. In an aspect, the syringe can include any of a number of standard syringes used for biopsy. Syringes such as those above are available from commercial sources, e.g., from Becton, Dickinson and Company, Franklin Lakes, N.J. or Covidien, Mansfield, Mass. In an aspect, the syringe can include any of a variety of sizes including, but not limited to, 0.05 ml, 0.1 ml, 0.5 ml, 1.0 ml, 3 ml, 5 ml, 6 ml, 10 ml, 20 ml, 35 ml, 50 ml, or 60 ml. In an aspect, the syringe is manufactured from plastic. In an aspect, the syringe is manufactured from glass. In an aspect, the syringe is intended for single use. In an aspect, the syringe includes any of a number of standard syringes, auto-disable syringes, or retractable syringes pre-qualified for use by the World Health Organization. See, e.g., Product List at WHO website accessed Dec. 10, 2013 at the following address http://apps.who.int/immunization_standards/vaccine_quality/pqs-_catalogue/categorypage.aspx?id_cat=37, which is incorporated herein by reference.

In an aspect, the connector portion 1420 of the second end 1434 of the first hollow cylinder 1430 is configured to connect to an aspiration device. In an aspect, the connector portion 1420 of the second end 1434 of the first hollow cylinder 1430 is configured to connect to a biopsy device. In an aspect, the connector portion 1420 of the second end 1434 of the first hollow cylinder 1430 is configured to connect to an evacuated tube, e.g., a BD Vacutainer® Blood Collection Tube from Becton, Dickinson and Company.

In an aspect, the connector portion 1420 of the second end 1434 of the first hollow cylinder 1430 includes a fitting sized for attachment to a syringe. In an aspect, the connector portion 1420 of the second end 1434 of the first hollow cylinder 1430 includes a slip-tip fitting. In an aspect, the connector portion 1420 of the second end 1434 of the first hollow cylinder 1430 includes a lock fitting. In an aspect, the connector portion 1420 of the second end 1434 of the first hollow cylinder 1430 includes a Luer lock fitting. In an aspect, the connector portion 1420 of the second end 1434 of the first hollow cylinder 1430 includes a screw fitting.

Penetrating device 1400 includes second hollow cylinder 1436. In an aspect, the second hollow cylinder 1436 is formed from stainless steel. In an aspect, the second hollow cylinder 1436 is formed form at least one of metal, alloy, plastic, glass, polymer, or ceramic. Non-limiting aspects of forming a second hollow cylinder are described above herein.

Penetrating device 1400 includes substantially ring-shaped first end piece 1442. In an aspect, the substantially ring-shaped first end piece 1442 is formed from at least one of stainless steel, metal, alloy, plastic, glass, polymer, or ceramic. In an aspect, the second hollow cylinder 1436 and the substantially ring-shaped first end piece 1442 are substantially non-porous. For example, the fluid composition in the fluid reservoir portion is able to flow through the plurality of pores in the first hollow cylinder but not through the second hollow cylinder or the substantially ring-shaped first end piece.

Penetrating device 1400 further includes a substantially ring-shaped second end piece 1448 which forms a deformable barrier. In an aspect, the substantially ring-shaped second end piece is formed from a deformable material. FIGS. 15A and 15B illustrates aspects of a penetrating device including a substantially ring-shaped second end piece formed from a deformable material. FIG. 15A is a schematic of a longitudinal cross-section through penetrating device 1500. Penetrating device 1500 includes a first hollow cylinder 1430 having a first end 1432 and a second end 1434, the first hollow cylinder 1430 including a plurality of pores 1414, the second end 1434 of the first hollow cylinder 1430 having a connector portion 1420; a second hollow cylinder 1436 having a first end 1438 and a second end 1440, the second hollow cylinder 1436 disposed within the first hollow cylinder 1430 and substantially coaxial to the first hollow cylinder 1430; a substantially ring-shaped first end piece 1442 having an outer edge 1444 and an inner edge 1446, the outer edge 1444 of the substantially ring-shaped first end piece 1442 secured to the first end 1432 of the first hollow cylinder 1430 and the inner edge 1446 of the substantially ring-shaped first end piece 1442 secured to the first end 1438 of the second hollow cylinder 1436, wherein the first hollow cylinder 1430, the second hollow cylinder 1436, and the substantially ring-shaped first end piece 1442 form a penetrating edge 1412; a substantially ring-shaped second end piece 1510 having an outer edge 1520 and an inner edge 1530, the outer edge 1520 of the substantially ring-shaped second end piece 1510 secured to a portion of the first hollow cylinder 1430 proximal to the second end 1434 of the first hollow cylinder 1430 and the inner edge 1530 of the substantially ring-shaped second end piece 1510 secured proximal to the second end 1440 of the second hollow cylinder 1436, the substantially ring-shaped second end piece 1510 formed from a deformable material; a fluid reservoir portion 1540 for holding a fluid composition (shown as stippling), the fluid reservoir portion 1540 defined by the first hollow cylinder 1430, the second hollow cylinder 1436, the substantially ring-shaped first end piece 1442, and the substantially ring-shaped second end piece 1510, the fluid reservoir portion 1540 in fluid communication with the plurality of pores 1414; and a lumen 1456 defined by the second hollow cylinder 1436, lumen 1456 having a first end 1458 and a second end 1460, the first end 1458 of lumen 1456 in fluid communication with the penetrating edge 1412.

FIG. 15B is a schematic of a longitudinal cross-section of penetrating device 1500 in the presence of a pressure 1550. In an aspect, pressure 1550 causes the deformable material of the substantially ring-shaped second end piece 1510 to deform. In an aspect, deformation of the deformable material of the substantially ring-shaped second end piece 1510 induces flow of the fluid composition (shown as stippling) from the fluid reservoir portion 1540 out at least one of the plurality of pores 1414. In an aspect, the deformation of the deformable material of the substantially ring-shaped second end piece is reversible, e.g., reversibly altering the shape of the substantially ring-shaped second end piece. In an aspect, the deformation of the deformable material of the substantially ring-shaped second end piece is irreversible, e.g., irreversibly altering the shape of the substantially ring-shaped second end piece.

In an aspect, the substantially ring-shaped second end piece 1510 is formed from a thin barrier of deformable material. For example, the substantially ring-shaped second end piece can be formed from a thin barrier of reversibly deformable material, e.g., an elastomer. For example, the substantially ring-shaped second end piece can be formed from a thin barrier of irreversibly deformable material, e.g., a thin barrier of aluminum. In an aspect, the substantially ring-shaped second end piece 1510 is formed from a deformable polymer. For example, the substantially ring-shaped second end piece can be formed from a deformable plastic or rubber. In an aspect, the substantially ring-shaped second end piece 1510 is formed from deformable plastic. For example, the substantially ring-shaped second end piece can be formed from a thin piece of molded low density polyethylene. Non-limiting examples of plastics include polyethylene terephthalate, polyethylene, polyvinyl chloride, polyvinylidene chloride, polypropylene, polystyrene, nylons, polycarbonate, or polyurethanes. In an aspect, the substantially ring-shaped second end piece 1510 is formed from a deformable metal. For example, the substantially ring-shaped second end piece can be formed from a thin sheet of aluminum. In an aspect, the deformable metal includes a ductile metal, e.g., copper, silver, or gold. In an aspect, the substantially ring-shaped second end piece is formed from a shape memory metal, e.g., nickel titanium alloy.

In an aspect, the substantially ring-shaped second end piece is formed from a rigid, low-friction material. FIGS. 16A and 16B illustrate aspects of a penetrating device including a substantially ring-shaped second end piece formed from a rigid, low-friction material. FIG. 16A is a schematic of a longitudinal cross-section through penetrating device 1600. Penetrating device 1600 includes a first hollow cylinder 1430 having a first end 1432 and a second end 1434, the first hollow cylinder 1430 includes a plurality of pores 1414, the second end 1434 of the first hollow cylinder 1430 having a connector portion 1420; a second hollow cylinder 1436 having a first end 1438 and a second end 1440, the second hollow cylinder 1436 disposed within the first hollow cylinder 1430 and substantially coaxial to the first hollow cylinder 1430; a substantially ring-shaped first end piece 1442 having an outer edge 1444 and an inner edge 1446, the outer edge 1444 of the substantially ring-shaped first end piece 1442 secured to the first end 1432 of the first hollow cylinder 1430 and the inner edge 1446 of the substantially ring-shaped first end piece 1442 secured to the first end 1438 of the second hollow cylinder 1436, wherein the first hollow cylinder 1430, the second hollow cylinder 1436, and the substantially ring-shaped first end piece 1442 form a penetrating edge 1412; a substantially ring-shaped second end piece 1610 having an outer edge 1620 and an inner edge 1630, the outer edge 1620 of the substantially ring-shaped second end piece 1610 adjacent to a portion of the first hollow cylinder 1430 proximal to the second end 1434 of the first hollow cylinder 1430 and the inner edge 1630 of the substantially ring-shaped second end piece 1610 adjacent to a portion of the second hollow cylinder 1436 proximal to the second end 1440 of the second hollow cylinder 1436, the substantially ring-shaped second end piece 1610 forming a movable barrier; a fluid reservoir portion 1640 for holding a fluid composition (shown as stippling), the fluid reservoir portion 1640 defined by the first hollow cylinder 1430, the second hollow cylinder 1436, the substantially ring-shaped first end piece 1442, and the substantially ring-shaped second end piece 1610, the fluid reservoir portion 1640 in fluid communication with the plurality of pores 1414; and a lumen 1456 defined by the second hollow cylinder 1436, the lumen 1456 having a first end 1458 and a second end 1460, the first end 1458 of the lumen 1456 in fluid communication with the penetrating edge 1412.

FIG. 16B is a schematic of a longitudinal cross-section of penetrating device 1600 in the presence of a pressure 1650.

In an aspect, pressure 1650 causes the substantially ring-shaped second end piece 1610 formed from a rigid, low friction material to move. In an aspect, movement of the substantially ring-shaped second end piece 1610 formed from the rigid, low friction material in the fluid reservoir portion 1640 induces flow of the fluid composition (shown as stippling) from the fluid reservoir portion 1640 out at least one of the plurality of pores 1414. In an aspect, the substantially ring-shaped second end piece 1610 is at least partially formed from a rigid, low-friction material. In an aspect, the rigid, low-friction material includes silicone.

In an aspect, the substantially ring-shaped second end piece forms a deformable barrier. In an aspect, deforming the deformable barrier induces flow of the fluid composition from the fluid reservoir portion and out at least one of the plurality of pores. In an aspect, the deformable barrier formed by the substantially ring-shaped second end piece is deformable in response to pressure. In an aspect, the deformable barrier formed by the substantially ring-shaped second end piece is deformable in response to manually applied pressure. In an aspect, the deformable barrier formed by the substantially ring-shaped second end piece is deformable in response to mechanically applied pressure. In an aspect, the pressure includes fluid pressure applied by in flow of a second fluid composition from a second fluid reservoir portion, e.g., a syringe. In an aspect, the pressure includes air pressure.

In an aspect, the deformable barrier formed by the substantially ring-shaped second end piece is deformable in response to applied energy. In an aspect, the deformable barrier formed by the substantially ring-shaped second end piece is deformable in response to electrical, thermal, optical, acoustic, magnetic, or electromagnetic energy. In an aspect, the substantially ring-shaped second end piece is formed from a deformable material responsive to at least one of electrical, thermal, optical, acoustic, magnetic, or electromagnetic energy.

Returning to FIG. 14, the penetrating portion of penetrating device 1400 includes penetrating edge 1412. In an aspect, the penetrating edge 1412 includes a sharp piercing edge. In an aspect, the penetrating edge 1412 includes a sharp bevelled edge. In an aspect, the penetrating edge 1412 includes at least one sharp edge able to pierce a material. In an aspect, the penetrating edge 1412 includes at least one sharp edge able to pierce metal, wood, concrete, plastic, polymer, fiberglass, resin, acrylic, latex, rubber, paper, or fabric. In an aspect, the penetrating edge 1412 includes at least one sharp edge able to pierce plant material. In an aspect, the penetrating edge 1412 includes at least one sharp edge able to pierce a body tissue of an animal. In an aspect, the penetrating edge 1412 includes at least one sharp edge able to pierce skin, endothelium, muscle, adipose, bone, cartilage, eye tissue, neural tissue, or internal organ tissue.

Penetrating device 1400 includes fluid reservoir portion 1454 for holding a fluid composition, the fluid reservoir portion 1454 defined by the first hollow cylinder 1430, the second hollow cylinder 1436, the substantially ring-shaped first end piece 1442, and the substantially ring-shaped second end piece 1448, the fluid reservoir portion 1454 in fluid communication with the plurality of pores 1414. In an aspect, the fluid composition of the fluid reservoir portion 1454 includes at least one lubricant. For example, the fluid reservoir portion can include glycerol. In an aspect, the fluid composition of the fluid reservoir portion 1454 includes at least one of an anesthetic or an analgesic. For example, the fluid reservoir portion can include lidocaine. In an aspect, the fluid composition of the fluid reservoir portion 1454 includes at least one antiseptic. For example, the fluid reservoir portion can include iodine. In an aspect, the fluid composition of the fluid reservoir portion 1454 includes at least one antimicrobial agent. For example, the fluid reservoir portion can include a topical antibiotic. In an aspect, the fluid composition of the fluid reservoir portion 1454 includes at least one anticoagulant. For example, the fluid reservoir portion can include heparin. In an aspect, the fluid composition of the fluid reservoir portion 1454 includes at least one antihemorrhagic. For example, the fluid reservoir portion can include a styptic agent. In an aspect, the fluid composition of the fluid reservoir portion 1454 includes at least one treatment agent. For example, the fluid reservoir portion can include a vaccine adjuvant. In an aspect, the fluid composition of the fluid reservoir portion 1454 includes at least one sealant. For example, the fluid reservoir portion can include a cyanoacrylate. Additional non-limiting examples of anesthetics, analgesics, antiseptics, antimicrobial agents, anticoagulants, antihemorrhagic agents, treatment agents, lubricants, and sealants have been described above herein. In an aspect, the fluid composition is incorporated into the fluid reservoir portion 1454 at the time of manufacture. In an aspect, the fluid composition is incorporated into the fluid reservoir portion 1454 at the time of use.

In an aspect, the second end of the lumen defined by the second hollow cylinder is in fluid communication with a second fluid reservoir portion. In an aspect, the second fluid reservoir portion includes a syringe, non-limiting examples of which have been described above herein. For example, the penetrating device can be connected to a standard syringe, e.g., a 3 milliliter syringe, through the connector portion associate with the first hollow cylinder. In an aspect, the second reservoir portion is in fluid communication with the second hollow cylinder through a flow conduit, e.g., rubber tubing. In an aspect, a piece of rubber tubing is attached to the connector portion of the first hollow cylinder of the penetrating device. In an aspect, the second fluid reservoir portion functions as an aspiration device. In an aspect, the second fluid reservoir portion functions as a biopsy device.

Figure 17A:
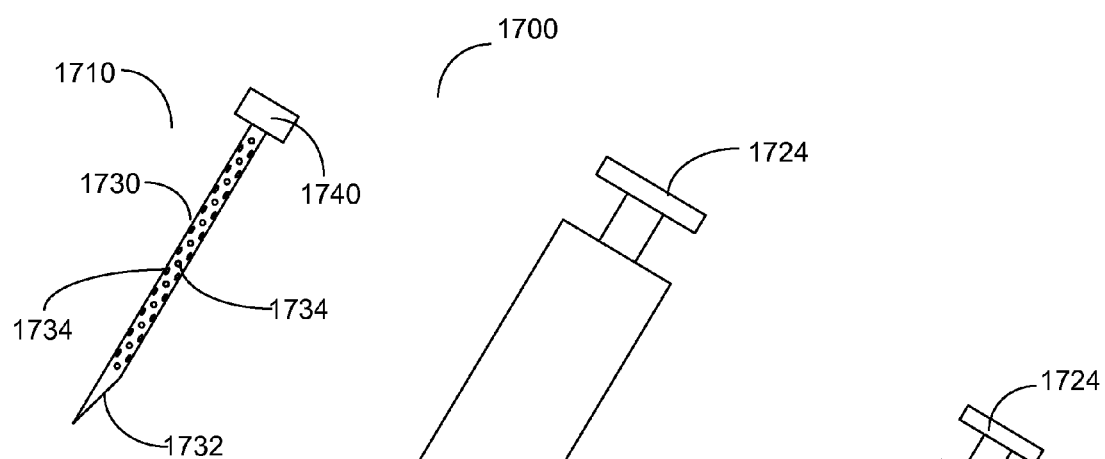
FIG. 17A shows a schematic of a penetrating system.
Figure 17B:
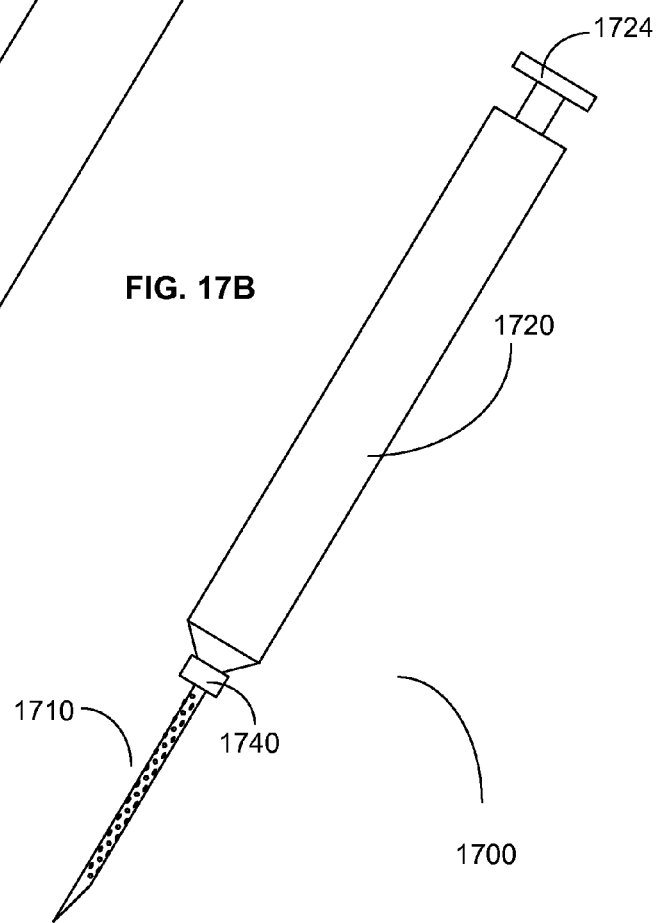
FIG. 17B shows a schematic of a penetrating system.

With reference to FIGS. 17A and 17B, shown are schematics of a penetrating system. FIG. 17A shows an external view of penetrating system 1700. Penetrating system 1700 includes penetrating device 1710 and second fluid reservoir portion 1720. Penetrating device 1710 includes penetrating portion 1730 and connector portion 1740. Penetrating portion 1730 includes penetrating edge 1732 and a plurality of pores 1734. Second fluid reservoir portion 1720 includes adaptor portion 1722 and initiator 1724. FIG. 17B illustrates an example of an assembled penetrating system 1700 including the connector portion 1740 of penetrating device 1710 disposed over the adaptor portion (1722 of FIG. 17A) of second fluid reservoir portion 1720, the second fluid reservoir portion 1720 in fluid communication with the penetrating device 1710.

Figure 18A:
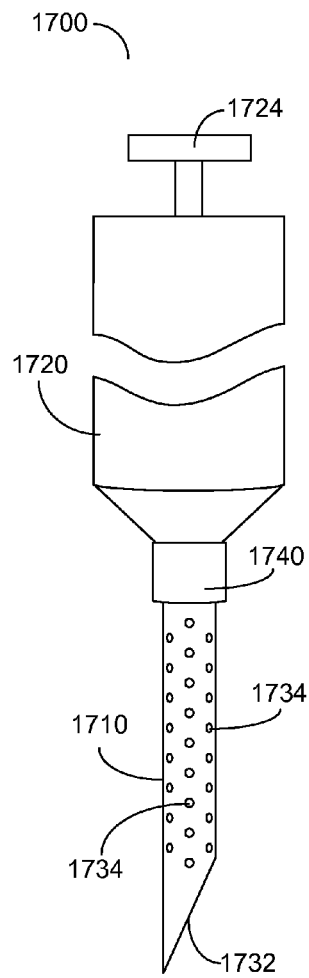
FIG. 18A shows a schematic of an external view of a penetrating system.
Figure 18B:
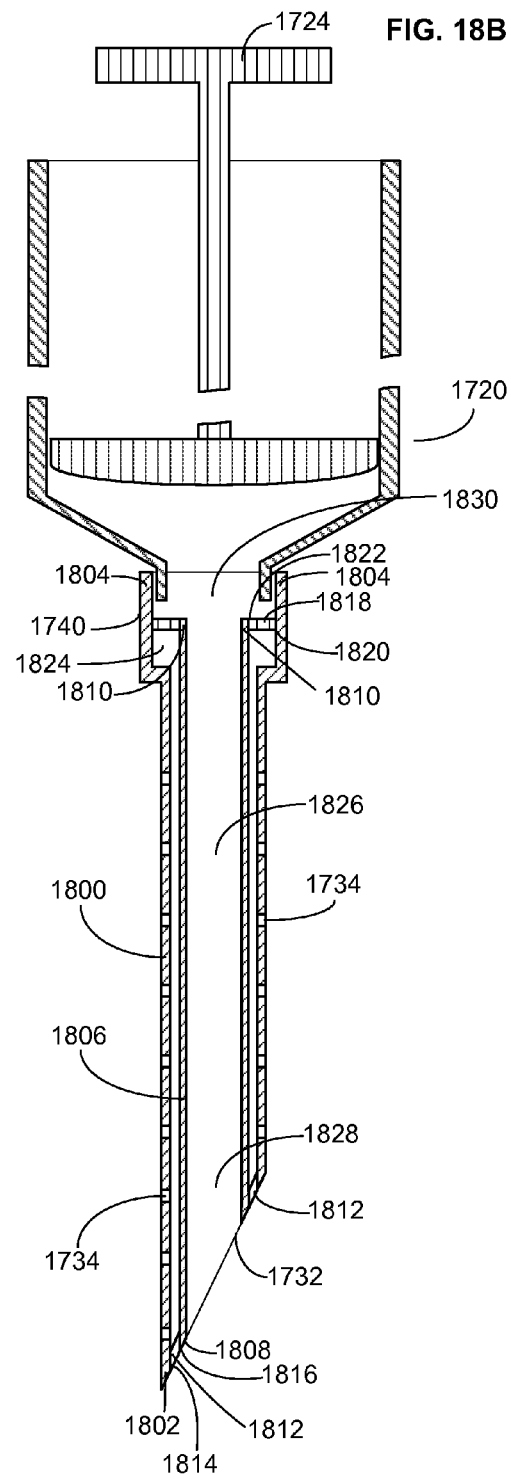
FIG. 18B shows a schematic of a longitudinal cross-section through a penetrating system.

FIGS. 18A and 18B illustrate further aspects of penetrating system 1700. FIG. 18 shows a schematic of a longitudinal cross-section through penetrating system 1700. Penetrating device 1710 includes a first hollow cylinder 1800 having a first end 1802 and a second end 1804, the first hollow cylinder 1800 including a plurality of pores 1734, the second end 1804 of the first hollow cylinder 1800 having a connector portion 1740. Penetrating device 1710 includes a second hollow cylinder 1806 having a first end 1808 and a second end 1810, the second hollow cylinder 1806 disposed within the first hollow cylinder 1800 and substantially coaxial to the first hollow cylinder 1800. Penetrating device 1710 includes a substantially ring-shaped first end piece 1812 having an outer edge 1814 and an inner edge 1816, the outer edge 1814 of the substantially ring-shaped first end piece 1812 secured to the first end 1802 of the first hollow cylinder 1800 and the inner edge 1816 of the substantially ring-shaped first end piece 1812 secured to the first end 1808 of the second hollow cylinder 1806, wherein the first hollow cylinder 1800, the second hollow cylinder 1806, and the substantially ring-shaped first end piece 1812 form a penetrating edge 1732. Penetrating device 1710 includes a substantially ring-shaped second end piece 1818 having an outer edge 1820 and an inner edge 1822, the outer edge 1820 of the substantially ring-shaped second end piece 1818 adjacent to a portion of the first hollow cylinder 1800 proximal to the second end 1804 of the first hollow cylinder 1800 and the inner edge 1822 of the substantially ring-shaped second end piece 1818 adjacent to a portion of the second hollow cylinder 1806 proximal to the second end 1810 of the second hollow cylinder 1806, the substantially ring-shaped second end piece 1818 forming a deformable barrier. Penetrating device 1710 includes a first fluid reservoir portion 1824 for holding a first fluid composition, the first fluid reservoir portion 1824 defined by the first hollow cylinder 1800, the second hollow cylinder 1806, the substantially ring-shaped first end piece 1812, and the substantially ring-shaped second end piece 1818, the first fluid reservoir portion 1824 in fluid communication with the plurality of pores 1734. Penetrating device 1710 includes a lumen 1826 defined by the second hollow cylinder 1806, the lumen 1826 having a first end 1828 and a second end 1830, the first end 1828 of the lumen 1826 in fluid communication with the penetrating edge 1732. Penetrating system 1700 further includes second fluid reservoir portion 1720 including an initiator 1724, the second fluid reservoir portion 1720 attached to the penetrating device 1710 through the connector portion 1740 of the first hollow cylinder 1800, the second fluid reservoir portion 1720 in fluid communication with the second end 1830 of the lumen 1826 defined by the second hollow cylinder 1806.

Penetrating system 1700 includes a penetrating device 1710 including a first hollow cylinder 1800. In an aspect, the first hollow cylinder 1800 is formed from stainless steel. In an aspect, the first hollow cylinder 1800 is formed from at least one of metal, alloy, plastic, glass, polymer, or ceramic. In an aspect, first hollow cylinder 1800 is formed from a porous material. In an aspect, the first hollow cylinder 1800 is formed from at least one of sintered metal particulate, glass particulate, or ceramic particulate. First hollow cylinder 1800 includes a plurality of pores 1734. In an aspect, each of the plurality of pores 1734 is substantially perpendicular to a central axis of the first hollow cylinder 1800. In an aspect, each of the plurality of pores 1734 is machined into the first hollow cylinder 1800. In an aspect, the connector portion 1740 of the second end 1804 of the first hollow cylinder 1800 includes a fitting sized for attachment to the second fluid reservoir portion 1720. In an aspect, the connector portion 1740 of the second end 1804 of the first hollow cylinder 1800 includes a slip-tip fitting. In an aspect, the connector portion 1740 of the second end 1804 of the first hollow cylinder 1800 includes a lock fitting, e.g., a screw fitting or a Luer lock fitting.

The penetrating device 1710 of system 1700 includes a second hollow cylinder 1806. In an aspect, the second hollow cylinder 1806 is formed from stainless steel. In an aspect, the second hollow cylinder 1806 is formed from at least one of metal, alloy, plastic, polymer, or ceramic. The penetrating device 1710 of system 1700 includes a substantially ring-shaped first end piece 1812. In an aspect, the substantially ring-shaped first end piece 1812 is formed from at least one of stainless steel, metal, alloy, plastic, glass, polymer, or ceramic. In an aspect, the second hollow cylinder 1806 and the substantially ring-shaped first end piece 1812 are substantially non-porous.

The penetrating device 1710 of system 1700 includes a substantially ring-shaped second end piece 1818. The substantially ring-shaped second end piece 1818 forms a deformable barrier. In an aspect, the deformable barrier includes a moveable barrier. In an aspect, the deformable barrier formed by the substantially ring-shaped second end piece is deformable in response to pressure. In an aspect, the deformable barrier formed by the substantially ring-shaped second end piece is deformable in response to manually applied pressure. In an aspect, the deformable barrier formed by the substantially ring-shaped second end piece is deformable in response to mechanically applied pressure.

In an aspect, the outer edge 1820 of the substantially ring-shaped second end piece is secured to a portion of the first hollow cylinder 1800 proximal to the second end 1804 of the first hollow cylinder 1800 and the inner edge 1822 of the substantially ring-shaped second end piece 1818 secured proximal to the second end 1810 of the second hollow cylinder 1806, the substantially ring-shaped second end piece 1818 formed from a deformable material. For example, the outer edge of the substantially ring-shaped second end piece is glued, welded, adhered, or otherwise secured to the inner wall of the first hollow cylinder and the inner edge of the substantially ring-shaped second end piece is glued, welded, adhered, or otherwise secured to the outer wall of the second hollow cylinder.

Figure 19A:
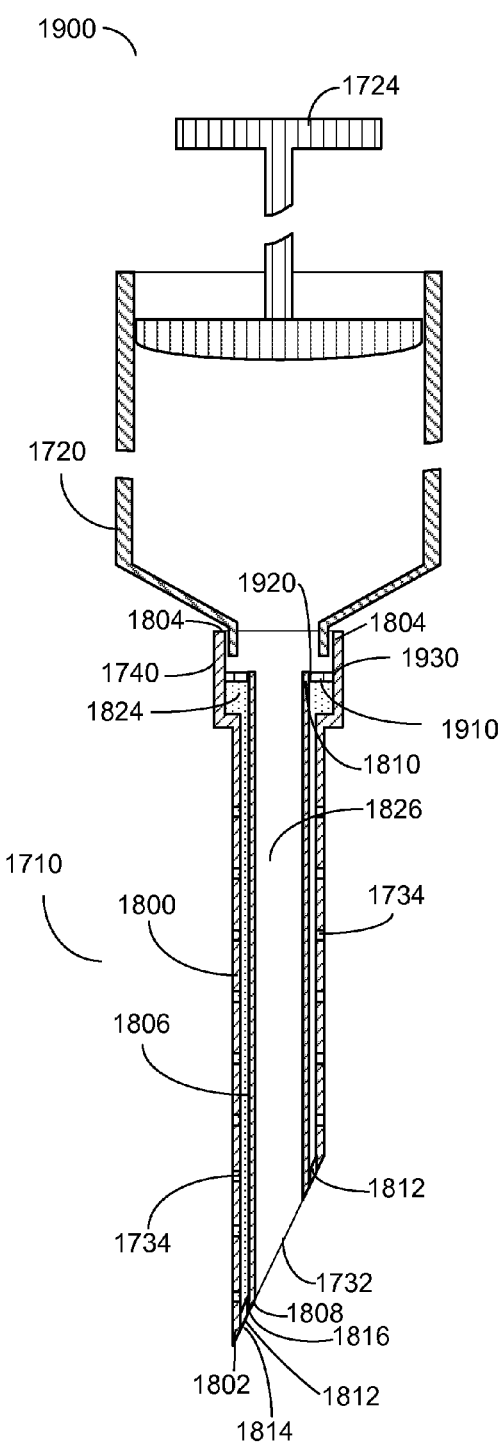
FIG. 19A shows a schematic of a longitudinal cross-section through a penetrating system including a deformable substantially ring-shaped second end piece.
Figure 19B:
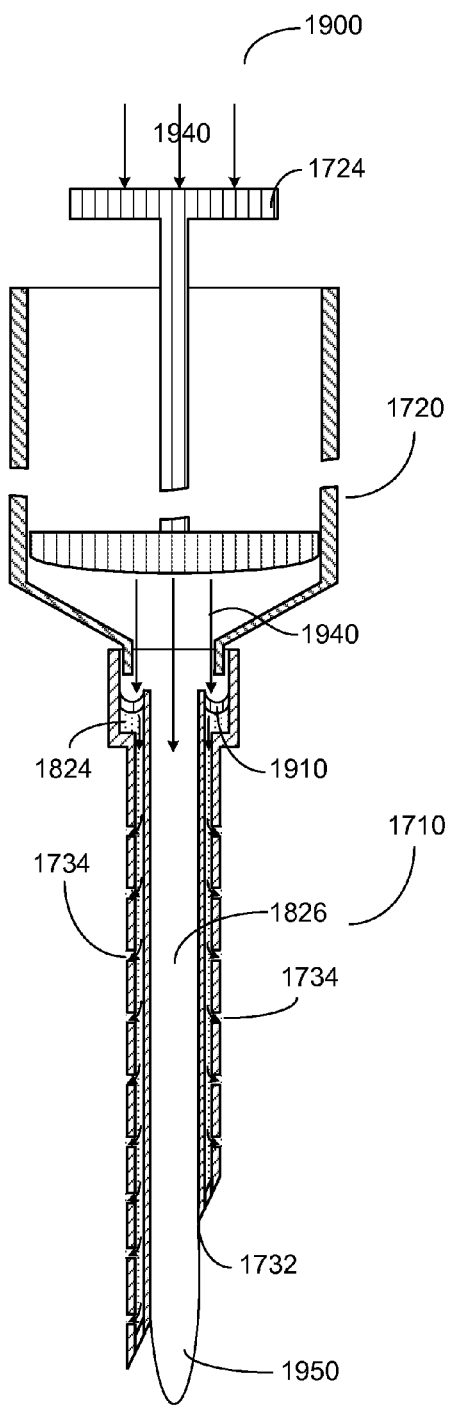
FIG. 19B shows a schematic of a longitudinal cross-section through a penetrating system including a deformable substantially ring-shaped second end piece.

FIGS. 19A and 19B illustrate aspects of a penetrating system 1900 including a substantially ring-shaped second end piece formed from a deformable material. FIG. 19A is a schematic of a longitudinal cross section through penetrating system 1900. Penetrating system 1900 includes penetrating device 1710 and second fluid reservoir portion 1720. Penetrating device 1710 includes a first hollow cylinder 1800 having a first end 1802 and a second end 1804, the first hollow cylinder 1800 including a plurality of pores 1734, the second end 1804 of the first hollow cylinder 1800 having a connector portion 1740. Penetrating device 1710 includes a second hollow cylinder 1806 having a first end 1808 and a second end 1810, the second hollow cylinder 1806 disposed within the first hollow cylinder 1800 and substantially coaxial to the first hollow cylinder 1800. Penetrating device 1710 includes a substantially ring-shaped first end piece 1812 having an outer edge 1814 and an inner edge 1816, the outer edge 1814 of the substantially ring-shaped first end piece 1812 secured to the first end 1802 of the first hollow cylinder 1800 and the inner edge 1816 of the substantially ring-shaped first end piece 1812 secured to the first end 1808 of the second hollow cylinder 1806, wherein the first hollow cylinder 1800, the second hollow cylinder 1806, and the substantially ring-shaped first end piece 1812 form a penetrating edge 1732. Penetrating device 1710 includes a substantially ring-shaped second end piece 1910 having an outer edge 1920 and an inner edge 1930, the outer edge 1920 of the substantially ring-shaped second end piece 1910 secured to a portion of the first hollow cylinder 1800 proximal to the second end 1804 of the first hollow cylinder 1800 and the inner edge 1930 of the substantially ring-shaped second end piece 1910 secured proximal to the second end 1810 of the second hollow cylinder 1806, the substantially ring-shaped second end piece 1910 forming a deformable barrier. Penetrating device 1710 includes a first fluid reservoir portion 1824 for holding a first fluid composition, the first fluid reservoir portion 1824 defined by the first hollow cylinder 1800, the second hollow cylinder 1806, the substantially ring-shaped first end piece 1812, and the substantially ring-shaped second end piece 1818, the first fluid reservoir portion 1824 in fluid communication with the plurality of pores 1734. Penetrating device 1710 includes a lumen 1826 defined by the second hollow cylinder 1806, the lumen 1826 having a first end and a second end, the first end of the lumen 1826 in fluid communication with the penetrating edge 1732. Penetrating system 1700 further includes second fluid reservoir portion 1720 including an initiator 1724, the second fluid reservoir portion 1720 attached to the penetrating device 1710 through the connector portion 1740 of the first hollow cylinder 1800, the second fluid reservoir portion 1720 in fluid communication with the second end of lumen 1826 defined by the second hollow cylinder 1806. In an aspect, the second fluid reservoir portion 1720 is configured to hold a second fluid composition. In an aspect, the second fluid reservoir portion is configured to hold a captured sample.

FIG. 19B shows a schematic of fluid flow through a longitudinal cross-section through penetrating system 1900 in the presence of pressure 1940. In an aspect, pressure 1940 is shown causing deformation of the deformable material of the substantially ring-shaped second end piece 1910. In an aspect, deformation of the deformable material of the substantially ring-shaped second end piece induces flow of the first fluid composition from the first fluid reservoir portion out at least one of the plurality of pores. Shown is flow of the first fluid composition (shown as stippling) from the first fluid reservoir portion 1824 and out at least one of the plurality of pores 1734 in response to deformation of a deformable material of substantially ring-shaped second end piece 1910. Also shown is outflow of the second fluid composition 1950 from the penetrating edge 1732 of penetrating device 1710 in response to actuation of initiator 1724. For example, downward pressure 1940 on initiator 1724, e.g., a plunger, forces the second fluid composition 1950 from second fluid reservoir portion 1720, through lumen 1826 of penetrating device 1710, and out penetrating edge 1732. In addition, but not illustrated in FIG. 19B, is optional subsequent inflow of aspirated captured sample past penetrating edge 1732 of penetrating device 1710 in response to reverse actuation of initiator 1724.

In an aspect, the deformation of the deformable material of the substantially ring-shaped second end piece is reversible, e.g., reversibly altering the shape of the substantially ring-shaped second end piece. In an aspect, the deformation of the deformable material of the substantially ring-shaped second end piece is irreversible, e.g., irreversibly altering the shape of the substantially ring-shaped second end piece.

In an aspect, the substantially ring-shaped second end piece 1910 is formed from a thin barrier of deformable material. For example, the substantially ring-shaped second end piece can be formed from a thin barrier of reversibly deformable material, e.g., an elastomer. For example, the substantially ring-shaped second end piece can be formed from a thin barrier of irreversibly deformable material, e.g., a thin barrier of aluminum. In an aspect, the substantially ring-shaped second end piece 1910 is formed from a deformable polymer. For example, the substantially ring-shaped second end piece can be formed from a deformable plastic or rubber. In an aspect, the substantially ring-shaped second end piece 1910 is formed from deformable plastic. For example, the substantially ring-shaped second end piece can be formed from a thin piece of molded low density polyethylene. Non-limiting examples of plastics include polyethylene terephthalate, polyethylene, polyvinyl chloride, polyvinylidene chloride, polypropylene, polystyrene, nylons, polycarbonate, or polyurethanes. In an aspect, the substantially ring-shaped second end piece 1910 is formed from a deformable metal. For example, the substantially ring-shaped second end piece can be formed from a thin sheet of aluminum. In an aspect, the deformable metal includes a ductile metal, e.g., copper, silver, or gold. In an aspect, the substantially ring-shaped second end piece is formed from a shape memory metal, e.g., nickel titanium alloy.

In an aspect, the substantially ring-shaped second end piece of a penetrating device is formed from a moveable rigid, low-friction material. FIGS. 20A and 20B illustrate aspects of a penetrating system including a substantially ring-shaped second end piece formed from a rigid, low-friction material. FIG. 20A is a schematic of a longitudinal cross section through penetrating system 2000. Penetrating system 2000 includes penetrating device 1710 and second fluid reservoir portion 1720. Penetrating device 1710 includes a first hollow cylinder 1800 having a first end 1802 and a second end 1804, the first hollow cylinder 1800 including a plurality of pores 1734, the second end 1804 of the first hollow cylinder 1800 having a connector portion 1740. Penetrating device 1710 includes a second hollow cylinder 1806 having a first end 1808 and a second end 1810, the second hollow cylinder 1806 disposed within the first hollow cylinder 1800 and substantially coaxial to the first hollow cylinder 1800. Penetrating device 1710 includes a substantially ring-shaped first end piece 1812 having an outer edge 1814 and an inner edge 1816, the outer edge 1814 of the substantially ring-shaped first end piece 1812 secured to the first end 1802 of the first hollow cylinder 1800 and the inner edge 1816 of the substantially ring-shaped first end piece 1812 secured to the first end 1808 of the second hollow cylinder 1806, wherein the first hollow cylinder 1800, the second hollow cylinder 1806, and the substantially ring-shaped first end piece 1812 form a penetrating edge 1732. Penetrating device 1710 includes a substantially ring-shaped second end piece 2010 having an outer edge 2020 and an inner edge 2030, the outer edge 2020 of the substantially ring-shaped second end piece 2010 adjacent to a portion of the first hollow cylinder 1800 proximal to the second end 1804 of the first hollow cylinder 1800 and the inner edge 2030 of the substantially ring-shaped second end piece 2010 adjacent to a portion of the second hollow cylinder 1806 proximal to the second end 1810 of the second hollow cylinder 1806, the substantially ring-shaped second end piece 2010 forming a deformable barrier. In an aspect, substantially ring-shaped second end piece 2010 is formed from a rigid, low-friction material. In an aspect, the rigid, low-friction material includes silicone. Penetrating device 1710 includes a first fluid reservoir portion 1824 for holding a first fluid composition, the first fluid reservoir portion 1824 defined by the first hollow cylinder 1800, the second hollow cylinder 1806, the substantially ring-shaped first end piece 1812, and the substantially ring-shaped second end piece 2010, the first fluid reservoir portion 1824 in fluid communication with the plurality of pores 1734. Penetrating device 1710 includes a lumen 1826 defined by the second hollow cylinder 1806, the lumen 1826 having a first end and a second end, the first end of the lumen 1826 in fluid communication with the penetrating edge 1732. Penetrating system 1700 further includes second fluid reservoir portion 1720 for holding a second fluid composition, second fluid reservoir portion 1720 including an initiator 1724, the second fluid reservoir portion 1720 attached to the penetrating device 1710 through the connector portion 1740 of the first hollow cylinder 1800, the second fluid reservoir portion 1720 in fluid communication with the second end of lumen 1826 defined by the second hollow cylinder 1806.

FIG. 20B shows a schematic of fluid flow through a longitudinal cross-section through penetrating system 2000 in the presence of pressure 2040. In an aspect, pressure 2040 is shown causing movement of the substantially ring-shaped second end piece 2010. In an aspect, movement of the substantially ring-shaped second end piece formed from the rigid, low-friction material into the first fluid reservoir portion induces flow of the first fluid composition from the first fluid reservoir portion out at least one of the plurality of pores. Shown is flow of the first fluid composition (shown as stippling) from the first fluid reservoir portion 1824 and out at least one of the plurality of pores 1734 in response to movement of substantially ring-shaped second end piece 2010. Also shown is outflow of a second fluid composition 2050 from the penetrating edge 1732 of penetrating device 1710 in response to actuation of initiator 1724. For example, downward pressure 2040 on initiator 1724, e.g., a plunger, forces the second fluid composition 2050 from second fluid reservoir portion 1720, through the lumen of penetrating device 1710, and out penetrating edge 1732.

Returning to FIG. 17, the penetrating portion of penetrating system 1700 includes penetrating edge 1732. In an aspect, the penetrating edge 1732 includes a sharp piercing edge. In an aspect, penetrating edge 1732 includes a sharp bevelled edge. In an aspect, penetrating edge 1732 includes at least one sharp edge able to pierce a material. In an aspect, penetrating edge 1732 includes at least one sharp edge able to pierce metal, wood, concrete, plastic, polymer, fiberglass, resin, acrylic, latex, rubber, paper, or fabric. In an aspect, penetrating edge 1732 includes at least one sharp edge able to pierce plant tissue. In an aspect, penetrating edge 1732 includes at least one sharp edge able to pierce a body tissue of an animal. In an aspect, penetrating edge 1512 includes at least one sharp edge able to pierce skin, endothelium, muscle, adipose, bone, cartilage, eye tissue, neural tissue, or internal organ tissue.

Penetrating device 1710 of penetrating system 1700 includes first fluid reservoir portion 1824 for holding a first fluid composition, the first fluid reservoir portion 1824 defined by the first hollow cylinder 1800, the second hollow cylinder 1806, the substantially ring-shaped first end piece 1812, and the substantially ring-shaped second end piece 1818, the first fluid reservoir portion 1824 in fluid communication with the plurality of pores 1734. In an aspect, the first fluid composition of the first fluid reservoir portion 1824 includes at least one lubricant. In an aspect, the first fluid composition of the first fluid reservoir portion 1824 includes at least one of an anesthetic or an analgesic. In an aspect, the first fluid composition of the first fluid reservoir portion 1824 includes at least one antiseptic. In an aspect, the first fluid composition of the first fluid reservoir portion 1824 includes at least one antimicrobial agent. In an aspect, the first fluid composition of the first fluid reservoir portion 1824 includes at least one anticoagulant. In an aspect, the first fluid composition of the first fluid reservoir portion 1824 includes at least one antihemorrhagic agent. In an aspect, the first fluid composition of the first fluid reservoir portion 1824 includes at least one treatment agent. In an aspect, the first fluid composition of the first fluid reservoir portion 1824 includes at least one sealant. Non-limiting examples of anesthetics, analgesics, antiseptics, antimicrobial agents, anticoagulants, antihemorrhagic agents, treatment agents, lubricants, and sealants have been described above herein. In an aspect, the first fluid composition is incorporated into the first fluid reservoir portion 1824 at the time of manufacture. In an aspect, the first fluid composition is incorporated into the first fluid reservoir portion 1824 at the time of use.

Penetrating device 1710 of penetrating system 1700 includes second fluid reservoir portion 1720 including an initiator 1724, the second fluid reservoir portion 1720 attached to the penetrating device 1710 through the connector portion 1740 of the first hollow cylinder 1800, the second fluid reservoir portion 1720 in fluid communication with the second end of lumen 1826 defined by the second hollow cylinder 1806. In an aspect, second fluid reservoir portion 1720 is configured to hold a captured sample, e.g., a blood or tissue sample. In an aspect, second fluid reservoir portion 1720 is configured to hold a second fluid composition. In an aspect, the second fluid composition includes at least one vaccine. For example, the second fluid composition can include a version of the annual flu vaccine. Non-limiting examples of vaccines have been described above herein. In an aspect, the second fluid composition includes at least one therapeutic agent. In an aspect, the at least one therapeutic agent includes at least one of an anti-inflammatory agent, an antimicrobial agent, a chemotherapy agent, or a diabetes treatment agent. For example, the second fluid composition can include long-lasting insulin. Non-limiting examples of other therapeutic agents have been described above herein. In an aspect, the second fluid composition includes a dye, e.g., a diagnostic dye. In an aspect, the second fluid composition includes a wash solution, e.g., saline. In an aspect, the second fluid composition of the second fluid reservoir portion is configured for at least one of percutaneous administration, intravenous administration, subcutaneous administration, intraocular administration, intraosseus administration, epidural administration, intraarticular administration, intraperitoneal administration, intraoral administration, or intramuscular administration.

In an aspect, the second end of the lumen defined by the second hollow cylinder of the penetrating device is in fluid communication with a second fluid reservoir portion of the penetrating system. In an aspect, the second fluid reservoir portion includes a syringe, non-limiting examples of which have been described above herein. In an aspect, the second fluid reservoir portion includes an aspiration device. In an aspect, the second fluid reservoir portion includes a biopsy device. In an aspect, the second fluid reservoir portion includes an evacuated tube. In an aspect, the initiator 1724 includes a plunger, e.g., a standard plunger associated with a standard syringe. In an aspect, the initiator 1724 includes a pump, e.g., an infusion pump and/or an aspiration pump, to which the penetrating system can be attached.

In an aspect, the second fluid reservoir portion is in fluid communication with the lumen defined by the second hollow cylinder of the penetrating device through a flow conduit. In an aspect, the flow conduit includes tubing, e.g., surgical tubing. For example, the second fluid reservoir portion can be connected to the penetrating device of the penetrating system through a piece of surgical tubing attached to the connector portion of the penetrating device. FIG. 21 illustrates aspects of a penetrating system including a second fluid reservoir portion attached to a penetrating device through a flow conduit. Penetrating system 2100 includes penetrating device 2110 and second fluid reservoir portion 2120. Penetrating device 2110 includes connector portion 2130, penetrating edge 2140, and a plurality of pores 2150. Penetrating device 2110 includes the internal aspects of a penetrating device such as described in FIG. 18 including a substantially ring-shaped second end piece forming a deformable barrier, deformation or movement of which induces flow of a first fluid composition from a first fluid reservoir portion of penetrating device 2110 and out at least one of the plurality of pores 2150. Connector portion 2130 of penetrating device 2110 is attached to second fluid reservoir portion 2120 through flow conduit 2160. In an aspect, flow conduit 2160 includes surgical tubing. In an aspect, second fluid reservoir portion 2120 can include a syringe attached to penetrating device 2110 through flow conduit 2160, the syringe including a plunger for initiating flow. In an aspect, second fluid reservoir portion 2120 can include an infusion bag attached to penetrating device 2110 through flow conduit 2160, gravity used for initiating flow.

The second fluid reservoir portion of a penetrating system includes an initiator. In an aspect, the initiator includes a plunger. In an aspect, the initiator includes gravity. In an aspect, the initiator includes a pump. In an aspect, the initiator is associated with an aspirator device. In an aspect, the initiator is associated with a biopsy device. FIG. 22 illustrates aspects of a penetrating system including a second fluid reservoir portion attached to a penetrating device through a pump. System 2200 includes penetrating device 2210 and second fluid reservoir portion 2220. Penetrating device 2210 includes connector portion 2230, penetrating edge 2240, and a plurality of pores 2250. Penetrating device 2210 includes the internal aspects of a penetrating device such as described in FIG. 18 including a substantially ring-shaped second end piece forming a deformable barrier, deformation or movement of which induces flow of a first fluid composition from a first fluid reservoir portion of penetrating device 2210 and out at least one of the plurality of pores 2250. Connector portion 2230 of penetrating device 2210 is attached to second fluid reservoir portion 2220 through flow conduit 2260 and pump 2270. In an aspect, pump 2270 is a peristaltic pump configured to pull the second fluid composition from second fluid reservoir portion 2220 into fluid conduit 2260, through pump 2270, and into penetrating device 2210. In an aspect, the pump, e.g., an infusion pump, is positioned upstream of the second fluid reservoir portion and configured to push the second fluid composition from the second fluid reservoir portion, through the fluid conduit, and into the penetrating device. In an aspect, pump 2270 is an aspirating pump configured to pull a captured sample from an animal subject through penetrating device 2210, the fluid conduit 2260, and into second fluid reservoir portion 2220.

In an aspect, the second fluid reservoir portion is replaceable. For example, the second fluid reservoir portion can include a replaceable evacuated tube for blood collection, e.g., a BD Vacutainer® Blood Collection Tube from Becton, Dickinson and Company. For example, a first evacuated tube attached to the penetrating device can be used to collect a first sample, removed upon filling, and a second evacuated tube attached to the penetrating device to collect a second sample.

In an aspect, a penetrating system such as described in FIGS. 17 and 18 includes a computing component operably coupled to the initiator, the computing component including a microprocessor. In an aspect, a penetrating system such as described in FIGS. 17 and 18 includes at least one sensor. In an aspect, a penetrating system such as described in FIGS. 17 and 18 includes at least one sensor operably coupled to the computing component, the computing component including circuitry configured to controllably actuate the initiator in response to input from the at least one sensor.

Figure 23:
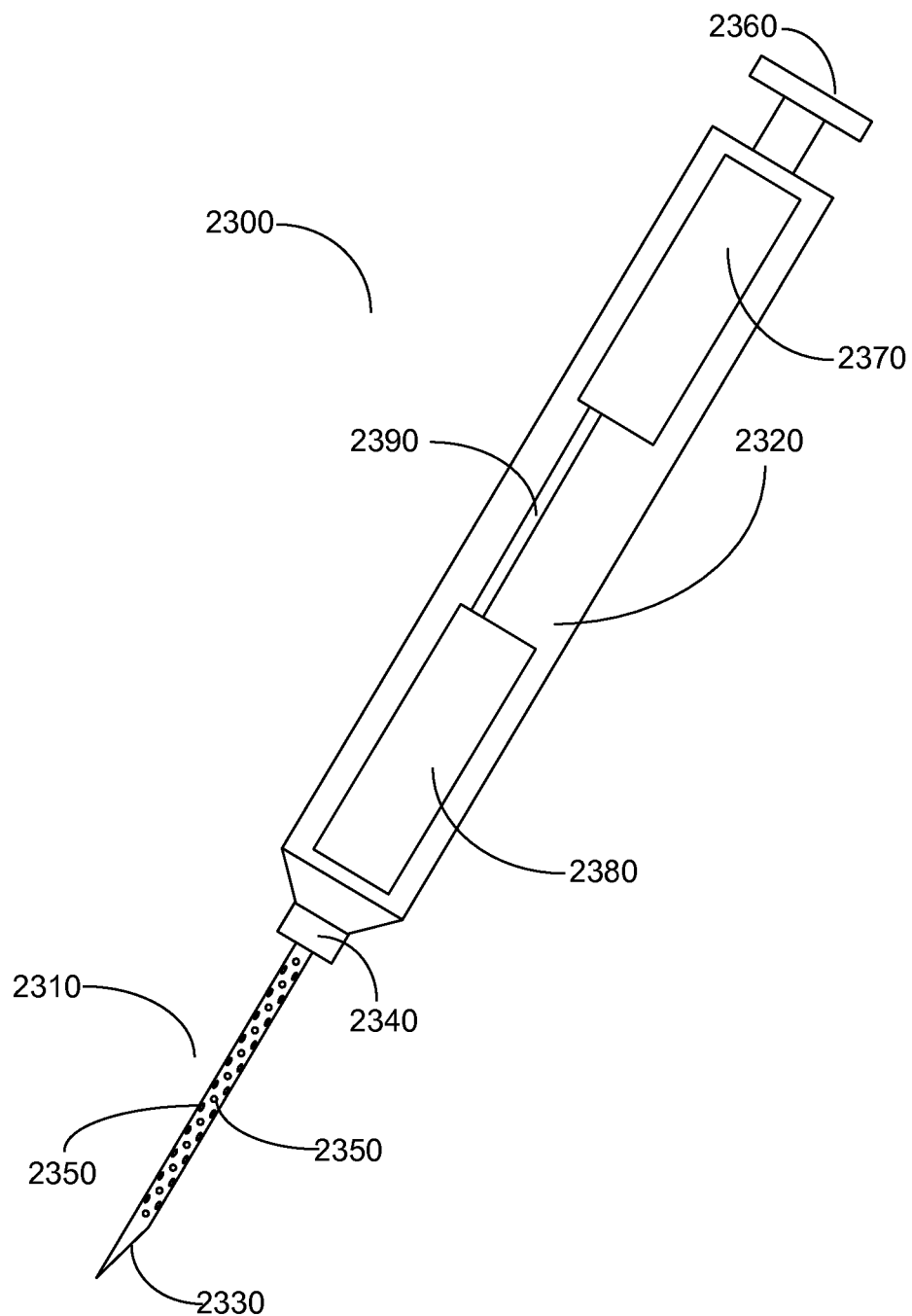
FIG. 23 shows a schematic of a penetrating system including a computing component.

FIG. 23 illustrates aspects of a penetrating system including a computing component and at least one sensor. Penetrating system 2300 includes penetrating device 2310 and second fluid reservoir portion 2320. Penetrating device 2310 includes penetrating edge 2330, connector portion 2340, and a plurality of pores 2350. Penetrating device 2310 includes all or part of the internal components described in FIGS. 17 and 18 including a deformable and/or moveable substantially ring-shaped second end piece. Second fluid reservoir portion 2320 includes initiator 2360. Penetrating system 2300 further includes computing component 2370 operably coupled to initiator 2360. Computing component 2370 includes a microprocessor and circuitry configured to controllably actuate initiator 2360. Penetrating system 2300 further includes at least one sensor 2380. In an aspect, at least one sensor 2380 includes at least one of an accelerometer, a clock, a pressure sensor, a temperature sensor, a proximity sensor, or a chemical sensor. At least one sensor 2380 is operably coupled to computing component 2370 through communications link 2390. In an aspect, computing component 2370 includes circuitry configured to controllably actuate initiator 2360 in response to input from at least one sensor 2380. For example, the computing component can include circuitry configured to actuate initiator 2360 in response to input from a proximity indicator indicating proximity to an injection target site.

Figure 24:
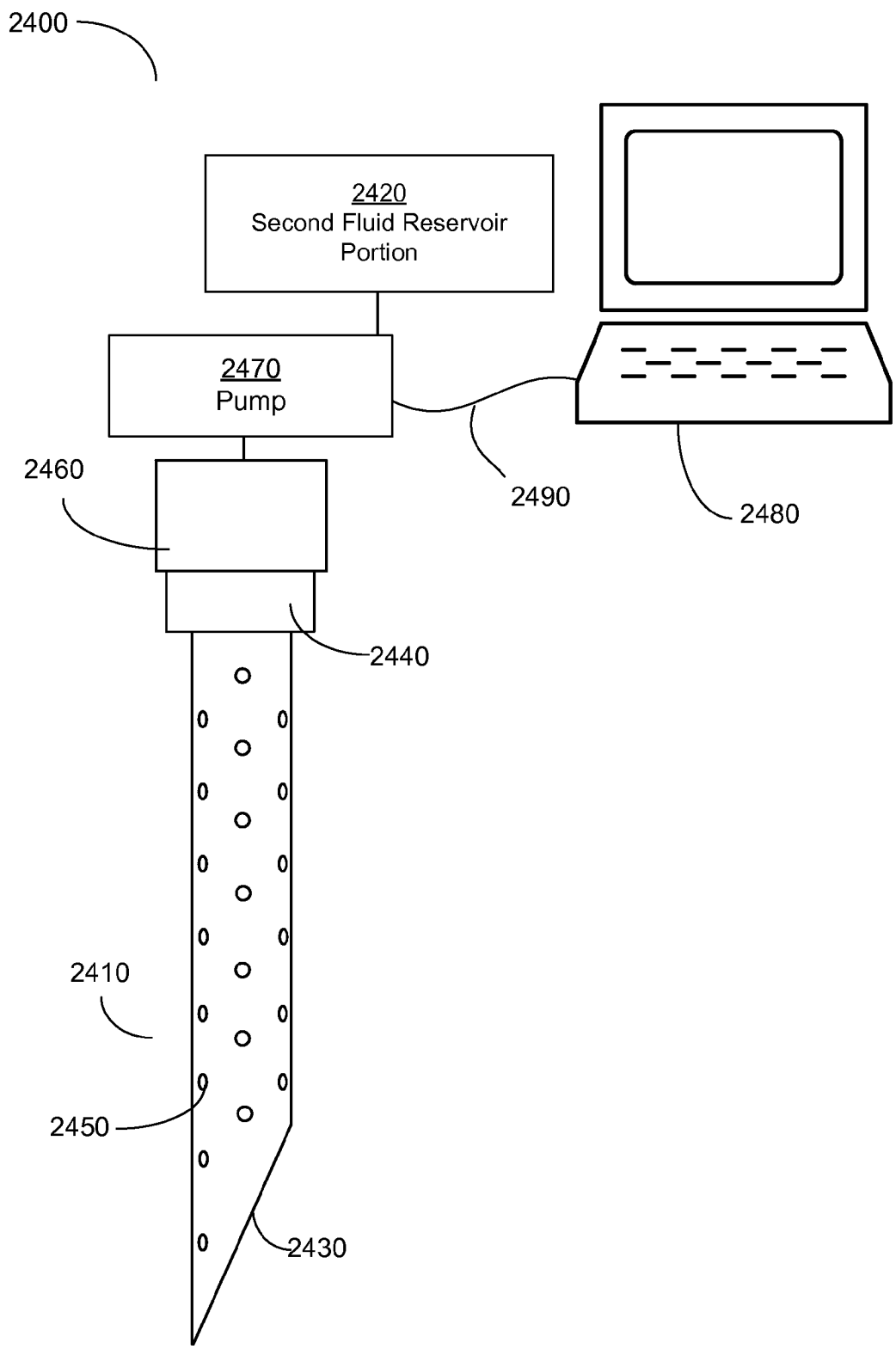
FIG. 24 shows a schematic of a penetrating system including a computing device, a pump, and a second fluid reservoir portion attached to a penetrating device through a flow conduit.

FIG. 24 illustrates a penetrating system including a pump and a computing component. Penetrating system 2400 includes penetrating device 2410 and second fluid reservoir portion 2420. Penetrating device 2410 includes penetrating edge 2430, connector portion 2440, and a plurality of pores 2450. Penetrating device 2410 includes all or part of the internal components described in FIGS. 17 and 18 including a deformable and/or moveable substantially ring-shaped second end piece, deformation or movement of which induces flow of a first fluid composition from a first fluid reservoir portion out at least one of the plurality of pores 2450. Connector portion 2440 of penetrating device 2410 is connected to second fluid reservoir portion 2420 through flow conduit 2460. Flow conduit 2460 is further connected to pump 2470. In an aspect, pump 2470 is configured to initiate flow of a second fluid composition, e.g., a vaccine or therapeutic agent, from the second fluid reservoir portion 2420, through flow conduit 2460, and into a lumen of penetrating device 2410. In an aspect, pump 2470 is configured to initiate flow of a captured sample from an animal subject into penetrating device 2410, through flow conduit 2460, and into second fluid reservoir portion 2420. Pump 2470 is operably coupled through communications link 2490 to computing component 2480. In an aspect, computing component 2480 is a desk top computer. In an aspect, computing component 2480 is incorporated into or is a part of pump 2470.

With regard to FIGS. 25A and 25B, shown are aspects of a penetrating device. FIG. 25A is a schematic of the exterior of penetrating device 2500. Penetrating device 2500 includes a penetrating portion 2502, a fluid reservoir portion 2504, and a connector portion 2506. Penetrating portion 2502 further includes a penetrating edge 2508 and a plurality of pores 2510. FIG. 25B shows a schematic of a cross-section through penetrating device 2500. Penetrating device 2500 includes first hollow cylinder 2512 having a first end 2514 and a second end 2516, first hollow cylinder 2512 including a plurality of pores 2510. Penetrating device 2500 further includes a second hollow cylinder 2518 having a first end 2520 and a second end 2522, the second hollow cylinder 2518 disposed within the first hollow cylinder 2512 and substantially coaxial to the first hollow cylinder 2512, the second end 2522 of the second hollow cylinder 2518 having a connector portion 2506. Penetrating device 2500 further includes a substantially ring-shaped end piece 2524 having an outer edge 2526 and an inner edge 2528, the outer edge 2526 of the substantially ring-shaped end piece 2524 secured to the first end 2514 of the first hollow cylinder 2512 and the inner edge 2528 of substantially ring-shaped end piece 2524 secured to the first end 2520 of second hollow cylinder 2518, wherein the first hollow cylinder 2512, the second hollow cylinder 2518, and the substantially ring-shaped end piece 2524 form penetrating edge 2508. Penetrating device 2500 further includes internal fluid conduit 2530 defined by a space between the first hollow cylinder 2512 and the substantially coaxial second hollow cylinder 2518, the internal fluid conduit 2530 in fluid communication with the plurality of pores 2510 along the length of first hollow cylinder 2512. Penetrating device 2500 further includes a fluid reservoir portion 2504 for holding a fluid composition, the fluid reservoir portion including a hollow structure with a first end 2532 and a second end 2534, the hollow structure disposed over, and substantially coaxial to a region of the second hollow cylinder 2518 proximal to the second end 2522 of second hollow cylinder 2518, the first end 2532 of the hollow structure secured to the second end 2516 of the first hollow cylinder 2512 and the second end 2534 of the hollow structure secured proximal to the second end 2522 of second hollow cylinder 2518, the hollow structure in fluid communication with internal fluid conduit 2530. Penetrating device 2500 further includes a lumen 2536 defined by the second hollow cylinder 2518, the lumen 2536 having a first end 2538 and a second end 2540, the first end 2538 of lumen 2536 in fluid communication with the penetrating edge 2508.

Penetrating device 2500 includes first hollow cylinder 2512. In an aspect, first hollow cylinder 2512 is formed from stainless steel. In an aspect, first hollow cylinder 2512 is formed from at least one of metal, alloy, plastic, glass, polymer, or ceramic. In an aspect, first hollow cylinder 2512 is formed from a porous material. For example, the first hollow cylinder can be formed from a porous ceramic material. In an aspect, first hollow cylinder 2512 is formed from at least one of sintered metal particulate, glass particulate, or ceramic particulate. Non-limiting examples of materials and methods for forming a first hollow cylinder have been described above herein. In an aspect, each of the plurality of pores 2510 is substantially perpendicular to a central axis of the first hollow cylinder 2512. In an aspect, the plurality of pores 2510 along the length of first hollow cylinder 2512 is machined into the first hollow cylinder 2512. For example, the plurality of pores can be drilled into the first hollow cylinder. In an aspect, the plurality of pores 2510 along the length of the first hollow cylinder 2512 is machined into the first hollow cylinder 2512 using at least one of a drill, a laser, or a waterjet. Additional non-limiting aspects of pores have been described above herein.

Penetrating device 2500 further includes second hollow cylinder 2518. In an aspect, second hollow cylinder 2518 includes an extended portion configured to engage a tube, for example an evacuated tube for blood collection, such as a BD Vacutainer® Blood Collection Tube from Becton, Dickinson and Company. In an aspect, the second hollow cylinder 2518 is formed from stainless steel. In an aspect, second hollow cylinder 2518 is formed from at least one of metal, alloy, plastic, glass, polymer, or ceramic. Non-limiting examples of materials and methods for forming a second hollow cylinder have been described above herein.

Second hollow cylinder 2518 has a connector portion 2506 at the second end 2522 of second hollow cylinder 2518. In an aspect, connector portion 2506 is formed from the same material as second hollow cylinder 2518 and represents an extension of second hollow cylinder 2518. In an aspect, connector portion 2506 is formed from a different material from second hollow cylinder 2518, but is secured or attached to the second end 2522 of second hollow cylinder 2518. In an aspect, connector portion 2506 is formed from at least one of metal, alloy, plastic, glass, polymer, or ceramic. In an aspect, connector portion 2506 of the second end 2522 of second hollow cylinder 2518 is configured to connect to a second fluid reservoir portion. In an aspect, connector portion 2506 of the second end 2522 of second hollow cylinder 2518 is configured to connect to a syringe. In an aspect, connector portion 2506 of the second end 2522 of second hollow cylinder 2518 is configured to connect to an aspirator. In an aspect, connector portion 2506 of the second end 2522 of second hollow cylinder 2518 is configured to connect to a biopsy device. In an aspect, connector portion 2506 of the second end 2522 of second hollow cylinder 2518 is configured to connect to a shield of an evaporated tube system. In an aspect, connector portion 2506 of the second end 2522 of second hollow cylinder 2518 is configured to connect to a dispensing apparatus, e.g., a laboratory or industrial dispensing apparatus. In an aspect, the second fluid reservoir portion includes a reservoir connected to connector portion 2506 of penetrating device 2500 through a flow conduit, e.g., tubing or needle extension.

In an aspect, the connector portion 2506 of the second end 2522 of the second hollow cylinder 2518 includes a fitting sized for attachment to a syringe, the syringe including a second fluid reservoir portion. In an aspect, connector portion 2506 of the second end 2522 of second hollow cylinder 2518 includes a fitting sized for attachment to an aspiration device. In an aspect, connector portion 2506 of the second end 2522 of second hollow cylinder 2518 includes a fitting sized for attachment to a biopsy device. In an aspect, connector portion 2506 of the second end 2522 of second hollow cylinder 2518 includes a fitting sized for attachment to a shield of an evaporated tube system. In an aspect, the connector portion 2506 of the second end 2522 of the second hollow cylinder 2518 includes a slip-tip fitting. In an aspect, the connector portion 2506 of the second end 2522 of the second hollow cylinder 2518 includes a lock fitting. In an aspect, the connector portion 2506 of the second end 2522 of the second hollow cylinder 2518 includes a Luer lock fitting.

Penetrating device 2500 includes substantially ring-shaped end piece 2524. In an aspect, the substantially ring-shaped end piece 2524 is formed from at least one of stainless steel, metal, alloy, plastic, glass, polymer, or ceramic. In an aspect, the second hollow cylinder 2518 and the substantially ring-shaped end piece 2524 are substantially non-porous. For example, the second hollow cylinder and the substantially ring-shaped end piece are formed either as a single piece or as separate pieces from a material that is impermeable to the contents, e.g., the fluid composition, of the fluid reservoir portion and the internal fluid conduit. In an aspect, substantially ring-shaped end piece 2524 is formed from the same material used to form second hollow cylinder 2518. In an aspect, substantially ring-shaped end piece 2524 is formed from a different material used to form second hollow cylinder 2518. In an aspect, substantially ring-shaped end piece 2524, first hollow cylinder 2512, and second hollow cylinder 2518 are formed from the same material, either as a single piece or as separate pieces secured to one another, each of the plurality of pores 2510 is machined, e.g., drilled, through the wall of first hollow cylinder 2512.

Penetrating device 2500 includes penetrating edge 2508 formed from first hollow cylinder 2512, second hollow cylinder 2518, and substantially ring-shaped end piece 2524. In an aspect, penetrating edge 2508 includes a sharp piercing edge. In an aspect, the penetrating edge 2508 includes a sharp beveled edge. In an aspect, the penetrating edge 2508 includes at least one sharp edge able to pierce a material. In an aspect, the penetrating edge 2508 includes at least one sharp edge able to pierce metal, wood, concrete, plastic, polymer, fiberglass, resin, acrylic, latex, rubber, paper, or fabric. In an aspect, the penetrating edge 2508 includes at least one sharp edge able to pierce plant material. In an aspect, the penetrating edge 2508 includes at least one sharp edge able to pierce a body tissue of an animal. In an aspect, the penetrating edge 2508 includes at least one sharp edge able to pierce skin, endothelium, muscle, adipose, bone, cartilage, eye tissue, neural tissue, or internal organ tissue.

Penetrating device 2500 includes fluid reservoir portion 2504 including a hollow structure attached at a first end 2532 to the second end 2516 of first hollow cylinder 2512 and at a second end 2534 to a region proximal to the second end 2522 of second hollow cylinder 2518. In an aspect, the hollow structure of the fluid reservoir portion 2504 is formed at least in part from a deformable material. In an aspect, the hollow structure of fluid reservoir portion 2504 is formed at least in part from a material capable of being deformed or of undergoing a shape change. In an aspect, the hollow structure of the fluid reservoir portion 2504 is formed at least in part from a deformable material capable of being deformed in response to pressure or stress. For example, the hollow structure of the first fluid reservoir portion can be formed from a material capable of being deformed by manual application of pressure, e.g., squeezing, with two or more fingers. In an aspect, deformation of the deformable material induces flow of the fluid composition from the fluid reservoir portion 2504, through the internal fluid conduit 2530, and out at least one of the plurality of pores 2510.

In an aspect, the deformable material is a material capable of elastic deformation in which the deformation of the material is reversible. For example, the deformable material can include an elastomer or shape memory metals. In an aspect, the deformable material is a material capable of plastic deformation in which the deformation of the material is irreversible. For example, the deformable material can include thermoplastics. In an aspect, the deformable material of the hollow structure includes at least one deformable polymer. For example, the deformable polymer can include a deformable plastic. For example, the deformable polymer can include a deformable rubber.

In an aspect, the deformable material of the hollow structure includes deformable plastic. For example, the deformable material of the hollow structure can include a thin piece of molded low density polyethylene. Non-limiting examples of plastics include polyethylene terephthalate, polyethylene, polyvinyl chloride, polyvinylidene chloride, polypropylene, polystyrene, nylons, polycarbonate, or polyurethanes.

In an aspect, the deformable material of the hollow structure includes deformable rubber. In an aspect, the deformable rubber includes natural rubber. For example, the deformable rubber can include natural latex rubber and/or vulcanized natural rubber. In an aspect, the deformable rubber includes synthetic rubber. For example, the deformable rubber can include styrene-butadiene rubber.

In an aspect, the deformable material of the hollow structure includes deformable metal. For example, the deformable material of the hollow structure can include at least in part a thin sheet of aluminum. In an aspect, the deformable metal includes a ductile metal, e.g., copper, silver, or gold. In an aspect, the deformable metal includes a shape memory metal. For example, the deformable metal can include an alloy, e.g., nickel titanium.

In an aspect, the deformable material of the hollow structure includes a thin wall of deformable material. For example, the deformable material of the hollow structure includes a thin wall of at least one of deformable polymer, plastic, rubber, or metal. In an aspect, the deformable material of the hollow structure is deformable in response to applied pressure. For example, the deformable material of the hollow structure can be configured to be squeezable. In an aspect, the deformable material of the hollow structure is deformable in response to manually applied pressure. For example, the deformable material of the hollow structure can be configured to deform in response to manually squeezing the deformable material with two of more fingers. In an aspect, the deformable material of the hollow structure is deformable in response to mechanically applied pressure. For example, the deformable material of the hollow structure can be configured to deform in response to mechanically squeezing the deformable material with a vice, clamp, pincher, or other device configured to apply pressure to the deformable material.

In an aspect, the deformable material of the hollow structure is deformable in response to applied energy. In an aspect, the deformable material of the hollow structure is deformable in response to electrical energy, thermal energy, optical energy, acoustic energy, magnetic energy, or electromagnetic energy. In an aspect, the deformable material of the hollow structure includes electro-active polymer, electro-active metal, magnetically responsive material, thermo-responsive material, photo-responsive material, or acoustically responsive material. For example, the hollow structure can be formed from a photo-responsive material that deforms in response to a specific wavelength of light. For example, the hollow structure can be formed from a thermal-responsive material that swells and/or contracts in response to fluctuations in temperature.

Penetrating device 2500 includes fluid reservoir portion 2504 for holding a fluid composition. In an aspect, the fluid composition of fluid reservoir portion 2504 includes at least one lubricant. In an aspect, the fluid composition of fluid reservoir portion 2504 includes at least one anesthetic. In an aspect, the fluid composition of fluid reservoir portion 2504 includes at least one antimicrobial agent. In an aspect, the fluid composition of fluid reservoir portion 2504 includes at least one analgesic. In an aspect, the fluid composition of fluid reservoir portion 2504 includes at least one treatment agent. In an aspect, the fluid composition of fluid reservoir portion 2504 includes at least one sealant. In an aspect, the fluid composition of fluid reservoir portion 2504 includes at least one anticoagulant. In an aspect, the fluid composition of fluid reservoir portion 2504 includes at least one antihemorrhagic agent. Non-limiting examples of anesthetics, lubricants, antimicrobial agents, analgesics, treatment agents, sealants, anticoagulants, and antihemorrhagic agents have been described above herein.

FIGS. 26A and 26B illustrate further aspects of penetrating device 2500. FIG. 26A shows a schematic of an external view of penetrating device 2500. In this view, the deformable material, e.g., deformable plastic, of fluid reservoir portion 2504 is being deformed using applied pressure, e.g., squeezing pressure applied with two or more fingers 2600. As a result of the applied pressure and deformation of fluid reservoir portion 2504, the fluid composition 2620 stored in the fluid reservoir portion is forced out at least one of the plurality of pores 2510. FIG. 26B shows a schematic of a longitudinal cross-section through penetrating device 2500. Also shown is applied pressure 2610 and deformation of fluid reservoir portion 2504. In an aspect, deformation of the deformable material of the fluid reservoir portion 2504 induces flow of the fluid composition (shown as stippling) from the fluid reservoir portion 2504, through the internal flow conduit 2530, and out at least one of the plurality of pores 2510.

Referring back to FIG. 25B, penetrating device 2500 includes lumen 2536 defined by the second hollow cylinder 2518. In an aspect, the second end 2540 of lumen 2536 defined by second hollow cylinder 2518 is in fluid communication with a second fluid reservoir portion. In an aspect, the second fluid reservoir portion includes a syringe body. For example, the lumen of the penetrating device allows for passage of a second fluid composition to flow from the second fluid reservoir portion, e.g., a syringe, through the penetrating device and into the pierced material, e.g., into the skin. For example, the lumen of the penetrating device allows for passage of a captured sample, e.g., a blood sample, to flow from an animal subject, through the penetrating device, and into the second fluid reservoir portion, e.g., a syringe. In an aspect, the second fluid reservoir portion includes a reservoir attached to the penetrating device through a flow conduit, e.g., tubing. In an aspect, the second fluid reservoir portion is part of an aspirating device. In an aspect, the second fluid reservoir portion is part of a biopsy device. In an aspect, the second fluid reservoir portion is an evacuated tube device.

With reference to FIGS. 27A and 27B, shown is a schematic of a penetrating system. FIG. 27A shows a schematic of the components of penetrating system 2700 including a penetrating device 2710 and a second fluid reservoir portion 2720. Penetrating device 2710 of penetrating system 2700 includes penetrating portion 2730, first fluid reservoir portion 2740, and connector portion 2750. Penetrating portion 2730 includes penetrating edge 2732 and a plurality of pores 2734. Penetrating system 2700 further includes a second fluid reservoir portion 2720. The second fluid reservoir portion 2720 includes adaptor 2722 sized for interaction with connector portion 2750 of the penetrating device 2710. The second fluid reservoir portion 2720 further includes initiator 2724. The second fluid reservoir portion 2720 is in fluid communication with a lumen of the penetrating device 2710. FIG. 27B shows a schematic of the components of penetrating system 2700 in an assembled state. Penetrating device 2710 is connected to the second fluid reservoir portion 2720 through the connector portion 2710 of penetrating device 2710 and the adaptor portion of the second fluid reservoir portion 2720.

Figure 28A:
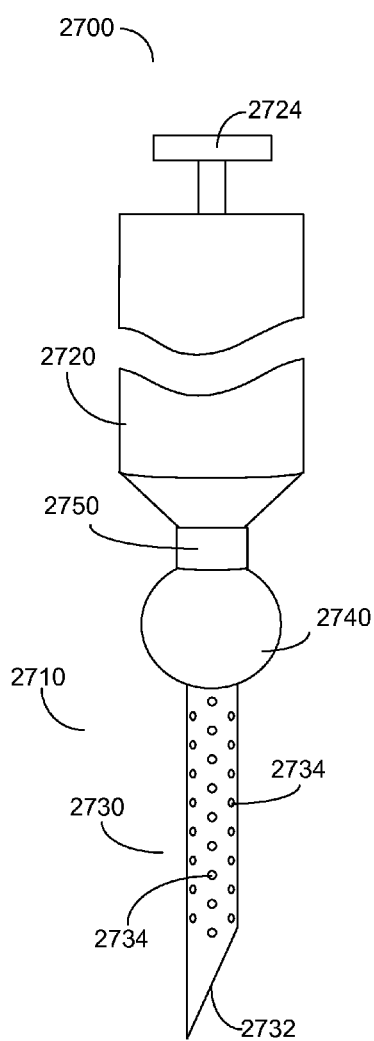
FIG. 28A shows a schematic of an external view of a penetrating system.
Figure 28B:
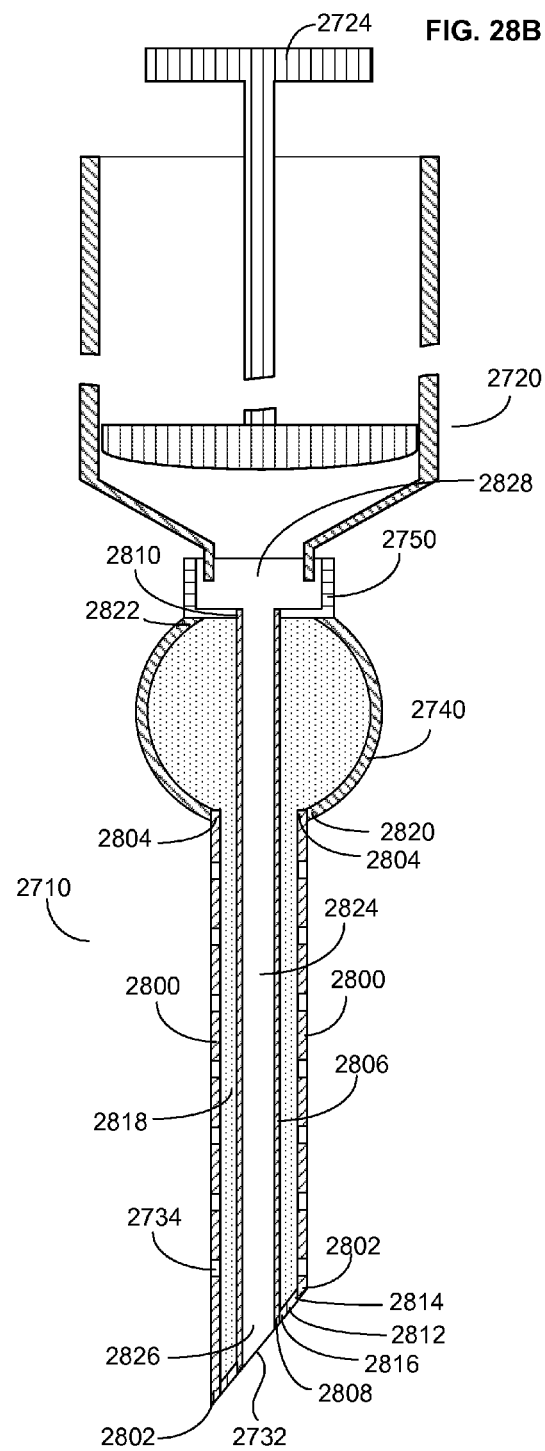
FIG. 28B shows a schematic of a longitudinal cross-section through a penetrating system.

FIGS. 28A and 28B illustrate further aspects of penetrating system 2700. FIG. 28A shows a schematic of an external view of penetrating system 2700. Penetrating system 2700 includes penetrating device 2710 including penetrating portion 2730 with penetrating edge 2732 and a plurality of pores 2734, first fluid reservoir portion 2740, and connector portion 2750, and second fluid reservoir portion 2710 including initiator 2724. FIG. 28B shows a schematic of a longitudinal cross-section through penetrating system 2700. Penetrating system 2700 includes penetrating device 2710 and second fluid reservoir portion 2720. Penetrating device includes a first hollow cylinder 2800 having a first end 2802 and a second end 2804, the first hollow cylinder 2800 including a plurality of pores 2734; a second hollow cylinder 2806 having a first end 2808 and a second end 2810, the second hollow cylinder 2806 disposed within the first hollow cylinder 2800 and substantially coaxial to the first hollow cylinder 2800, the second end 2810 of the second hollow cylinder 2806 having a connector portion 2750; a substantially ring-shaped end piece 2812 having an outer edge 2814 and an inner edge 2816, the outer edge 2814 of the substantially ring-shaped end piece 2812 secured to the first end 2802 of the first hollow cylinder 2800 and the inner edge 2816 of the substantially ring-shaped end piece secured to the first end 2808 of the second hollow cylinder 2806, wherein the first hollow cylinder 2800, the second hollow cylinder 2806, and the substantially ring-shaped end piece 2812 for a penetrating edge 2732; an internal fluid conduit 2818 defined by a space between the first hollow cylinder 2800 and the substantially coaxial second hollow cylinder 2806, the internal fluid conduit 2818 in fluid communication with the plurality of pores 2734 along the length of the first hollow cylinder 2800; a first fluid reservoir portion 2740 for holding a first fluid composition, the first fluid reservoir portion 2740 including a hollow structure with a first end 2820 and a second end 2822, the hollow structure disposed over, and substantially coaxial to a region of the second hollow cylinder 2806 proximal to the second end 2810 of the second hollow cylinder 2806, the first end 2820 of the hollow structure secured to the second end 2804 of the first hollow cylinder 2800 and the second end 2822 of the hollow structure secured proximal to the second end 2810 of the second hollow cylinder 2806, the hollow structure in fluid communication with the internal fluid conduit 2818; and a lumen 2824 defined by the second hollow cylinder 2806, the lumen 2824 having a first end 2826 and a second end 2828, the first end 2826 of the lumen 2824 in fluid communication with the penetrating edge 2732. Penetrating system 2700 further includes a second fluid reservoir portion 2720 including an initiator 2724, the second fluid reservoir portion 2720 attached to the connector portion 2750 of the penetrating device 2710, the second fluid reservoir portion 2720 in fluid communication with the second end 2828 of the lumen 2824 defined by the second hollow cylinder 2806.

Penetrating device 2710 of system 2700 includes first hollow cylinder 2800. In an aspect, the first hollow cylinder 2800 is formed from stainless steel. In an aspect, the first hollow cylinder 2800 is formed from at least one of metal, alloy, plastic, glass, polymer, or ceramic. In an aspect, the first hollow cylinder 2800 is formed from a porous material. For example, the first hollow cylinder can be formed from a porous ceramic material. In an aspect, first hollow cylinder 2800 is formed from at least one of sintered metal particulate, glass particulate, or ceramic particulate. Non-limiting aspects of materials and methods for forming a first hollow cylinder have been described above herein.

First hollow cylinder 2800 includes a plurality of pores 2734. In an aspect, each of the plurality of pores 2734 is substantially perpendicular to a central axis of the first hollow cylinder 2800. In an aspect, each of the plurality of pores 2734 is machined into the first hollow cylinder 2800. For example, the plurality of pores can be drilled into the first hollow cylinder. Other non-limiting aspects of pores in a first hollow cylinder have been described above herein.

Penetrating device 2710 of system 2700 further includes second hollow cylinder 2806. In an aspect, the second hollow cylinder 2806 is formed from stainless steel. In an aspect, second hollow cylinder 2806 is formed from at least one of metal, alloy, plastic, glass, polymer, or ceramic.

Second hollow cylinder 2806 has a connector portion 2750 at the second end 2810 of second hollow cylinder 2806. In an aspect the connector portion 2750 is formed from the same material as second hollow cylinder 2806 and represents an extension of second hollow cylinder 2806. In an aspect, connector portion 2750 is formed from a different material from second hollow cylinder 2806, but is secured or attached to the second end 2810 of second hollow cylinder 2806. In an aspect, connector portion 2750 is formed from at least one of metal, alloy, plastic, glass, polymer, or ceramic. In an aspect, the connector portion 2750 of the second end 2810 of the second hollow cylinder 2806 includes a fitting sized for attachment to the second fluid reservoir portion 2720. In an aspect, the connector portion 2750 of the second end 2810 of the second hollow cylinder 2806 includes a slip-tip fitting. In an aspect, the connector portion 2750 of the second end 2810 of the second hollow cylinder 2806 includes a lock fitting. In an aspect, the connector portion 2750 of the second end 2810 of the second hollow cylinder 2806 includes a screw lock fitting or a Luer lock fitting.

Penetrating device 2710 of system 2700 includes a substantially ring-shaped end piece 2812. In an aspect, the substantially ring-shaped end piece 2812 is formed from at least one of stainless steel, metal, alloy, plastic, glass, polymer, or ceramic. In an aspect, the second hollow cylinder 2806 and the substantially ring-shaped end piece 2812 are substantially non-porous. For example, the second hollow cylinder and the substantially ring-shaped end piece are formed either as a single piece or as separate pieces from a material that is impermeable to the contents, e.g., the fluid composition, of the fluid reservoir portion and the internal fluid conduit. In an aspect, the substantially ring-shaped end piece is formed from the same material used to form the second hollow cylinder. In an aspect, the substantially ring-shaped end piece is formed from a different material used to form the second hollow cylinder. In an aspect, the substantially ring-shaped end piece, the first hollow cylinder, and the second hollow cylinder are formed from the same material, either as a single piece or as separate pieces secured to one another, wherein each of the plurality of pores is machined, e.g., drilled, through the wall of the first hollow cylinder.

Penetrating device 2710 of system 2700 includes penetrating edge 2732 formed from first hollow cylinder 2800, second hollow cylinder 2806, and substantially ring-shaped end piece 2812. In an aspect, the penetrating edge 2732 includes a sharp piercing edge. In an aspect, the penetrating edge 2732 includes a sharp beveled edge. In an aspect, the penetrating edge 2732 includes at least one sharp edge able to pierce a material. In an aspect, the penetrating edge 2608 includes at least one sharp edge able to pierce metal, wood, concrete, plastic, polymer, fiberglass, resin, acrylic, latex, rubber, paper, or fabric. In an aspect, the penetrating edge 2732 includes at least one sharp edge able to pierce plant material. In an aspect, the penetrating edge 2732 includes at least one sharp edge able to pierce a body tissue of an animal. In an aspect, the penetrating edge 2732 includes at least one sharp edge able to pierce skin, endothelium, muscle, adipose, bone, cartilage, eye tissue, neural tissue, or internal organ tissue.

Penetrating device 2710 of system 2800 includes a first fluid reservoir portion 2740 for holding a first fluid composition, the first fluid reservoir portion 2740 including a hollow structure with a first end 2820 and a second end 2822, the hollow structure disposed over, and substantially coaxial to a region of the second hollow cylinder 2806 proximal to the second end 2810 of the second hollow cylinder 2806, the first end 2820 of the hollow structure secured to the second end 2804 of the first hollow cylinder 2800 and the second end 2822 of the hollow structure secured proximal to the second end 2810 of the second hollow cylinder 2806, the hollow structure in fluid communication with the internal fluid conduit 2818.

In an aspect, the hollow structure of the first fluid reservoir portion 2740 is formed at least in part from a deformable material. In an aspect, the hollow structure of the first fluid reservoir portion 2740 is formed at least in part from a material capable of being deformed or of undergoing a shape change. In an aspect, the hollow structure of the first fluid reservoir portion 2740 is formed at least in part from a deformable material capable of being deformed in response to pressure or stress. For example, the hollow structure of the first fluid reservoir portion can be formed from a material capable of being deformed by manual application of pressure, e.g., squeezing, with two or more fingers. In an aspect, deformation of the deformable material induces flow of the first fluid composition from first fluid reservoir portion 2740, through the internal fluid conduit 2818, and out at least one of the plurality of pores 2734.

In an aspect, the deformable material is a material capable of elastic deformation in which the deformation of the material is reversible. In an aspect, the deformable material is a material capable of plastic deformation in which the deformation of the material is irreversible. In an aspect, the deformable material of the hollow structure includes a deformable polymer. For example, the deformable polymer can include a deformable plastic or deformable rubber. In an aspect, the deformable material of the hollow structure includes deformable plastic. For example, the deformable material of the hollow structure can include a thin piece of molded low density polyethylene. Non-limiting examples of plastics have been described above herein. In an aspect, the deformable material of the hollow structure includes deformable rubber. In an aspect, the deformable rubber includes natural rubber, e.g., natural latex rubber, or synthetic rubber, e.g., styrene-butadiene rubber. In an aspect, the deformable material of the hollow structure includes deformable metal. For example, the deformable material of the hollow structure can include a thin portion of at least one of aluminum, copper, silver, gold, or a shape memory metal, e.g., nickel titanium.

In an aspect, the deformable material of the hollow structure includes a thin wall of deformable material. For example, the deformable material of the hollow structure includes a thin wall of at least one of deformable polymer, plastic, rubber, or metal. In an aspect, the deformable material of the hollow structure is deformable in response to applied pressure. For example, the deformable material of the hollow structure can be configured to be squeezable. In an aspect, the deformable material of the hollow structure is deformable in response to manually applied pressure. For example, the deformable material of the hollow structure can be configured to deform in response to manually squeezing the deformable material with two or more fingers. In an aspect, the deformable material of the hollow structure is deformable in response to mechanically applied pressure. For example, the deformable material of the hollow structure can be configured to deform in response to mechanically squeezing the deformable material with a vice, clamp, pincher, or other device configured to apply pressure to the deformable material.

In an aspect, the deformable material of the hollow structure is deformable in response to applied energy. In an aspect, the deformable material of the hollow structure is deformable in response to electrical energy, thermal energy, optical energy, acoustic energy, magnetic energy, or electromagnetic energy. In an aspect, the deformable material includes electro-active polymer, electro-active metal, magnetically responsive material, thermo-responsive material, photo-responsive material, or acoustically responsive material.

First fluid reservoir portion 2740 is configured to hold a first fluid composition. In an aspect, the first fluid composition of the first fluid reservoir portion 2740 includes at least one lubricant. In an aspect, the first fluid composition of the first fluid reservoir portion 2740 includes at least one anesthetic. In an aspect, the first fluid composition of the first fluid reservoir portion 2740 includes at least one antimicrobial agent. In an aspect, the first fluid composition of the first fluid reservoir portion 2740 includes at least one analgesic. In an aspect, the first fluid composition of the first fluid reservoir portion 2740 includes at least one treatment agent. In an aspect, the first fluid composition of the first fluid reservoir portion 2740 includes at least one sealant. In an aspect, the first fluid composition of the first fluid reservoir portion 2740 includes at least one anticoagulant. In an aspect, the first fluid composition of the first fluid reservoir portion 2740 includes at least one antihemorrhagic agent. Non-limiting examples of anesthetics, lubricants, antimicrobial agents, analgesics, treatment agents, sealants, anticoagulants, and antihemorrhagic agents have been described above herein.

Penetrating system 2700 further includes a second fluid reservoir portion 2720. In an aspect, the second fluid reservoir portion 2720 is configured for holding a second fluid composition, e.g., a vaccine, therapeutic agent, dye, wash solution, or other agent. In an aspect, the second fluid reservoir portion 2720 is configured for holding a captured sample, e.g., blood, tissue, marrow, aspirate, lavage, and the like. In an aspect, the second fluid reservoir portion 2720 includes a syringe. For example, the lumen of the penetrating device allows for passage of the second fluid composition to flow from the second fluid reservoir portion, e.g., a syringe, through the penetrating device and into the pierced material, e.g., into the skin. For example, the lumen of the penetrating device allows for passage of a captured sample to flow from an animal subject, through the penetrating device, and into the second fluid reservoir portion, e.g., the body of a syringe. For example, the second fluid reservoir portion can include a standard syringe, e.g., a 1 ml plastic syringe, attached to the connector portion of the penetrating device through a fitting, e.g., a slip-tip fitting or a Luer lock fitting. Non-limiting aspects of syringes have been described above herein. In an aspect, the second fluid reservoir portion 2720 includes an evacuated tube device. In an aspect, the second fluid reservoir portion 2720 includes an aspirator device. In an aspect, the second fluid reservoir portion 2720 includes a biopsy device. In an aspect, the second fluid reservoir portion 2720 includes a reservoir attached to the penetrating device through a flow conduit, e.g., tubing. For example, the second fluid reservoir portion can include an infusion bag for holding the second fluid composition, the infusion bag attached through surgical tubing to the penetrating device.

Second fluid reservoir portion 2720 includes an initiator 2724. In an aspect, initiator 2724 is configured to induce flow into or out of the second fluid reservoir portion 2720. In an aspect, initiator 2724 is configured to induce flow of a second fluid composition from the second fluid reservoir portion 2720 through the lumen 2824 of the attached penetrating device 2710. In an aspect, initiator 2724 is configured to induce flow of a captured sample from an animal subject, through the lumen 2824 of the attached penetrating device 2710, and into the second fluid reservoir portion 2720. In an aspect, the initiator 2724 includes a plunger. For example, the initiator can include a plunger associated with a syringe. For example, the second fluid reservoir portion can include a standard syringe with an associated plunger. In an aspect, the initiator 2724 includes a pump. For example, the initiator can include an infusion pump into which the penetrating system is inserted, the infusion pump pushing on a plunger portion of the second fluid reservoir portion. For example, the initiator can include a peristaltic pump having tubing that connects a second fluid reservoir portion to the penetrating device of the system. For example, the initiator can include an aspirating pump for pulling a capture sample out of an animal subject and into the penetrating device. In an aspect, the initiator includes a valve. In an aspect, the initiator includes gravity. For example, flow from an infusion bag can be initiated by opening a valve and allowing gravity to flow the second fluid composition from the infusion bag. In an aspect, the initiator includes a vacuum, e.g., a vacuum associated with an evacuated tube device.

The second fluid reservoir portion 2720 is configured to hold a second fluid composition. In an aspect, the second fluid composition includes at least one vaccine. For example, the second fluid composition can include a version of the annual flu vaccine. Non-limiting examples of vaccines have been described above herein. In an aspect, the second fluid composition includes at least one therapeutic agent. In an aspect, the at least one therapeutic agent includes at least one of an anti-inflammatory agent, an antimicrobial agent, a chemotherapy agent, or a diabetes treatment agent. For example, the second fluid composition can include long-lasting insulin. Non-limiting examples of other therapeutic agents have been described above herein. In an aspect, the second fluid composition includes at least one dye, e.g., a diagnostic dye. In an aspect, the second fluid composition includes a wash solution for an aspiration biopsy. In an aspect, the second fluid composition is formulated for at least one of percutaneous administration, intravenous administration, subcutaneous administration, intraocular administration, intraosseus administration, epidural administration, intraarticular administration, intraperitoneal administration, intraoral administration, or intramuscular administration.

FIGS. 29A and 29B illustrate further aspects of penetrating system 2700. FIG. 29A shows a schematic of an external view of fluid flow from penetrating system 2700. In this view, first fluid reservoir portion 2740 is being deformed using applied pressure, e.g., squeezing pressure applied with two or more fingers 2900. As a result of the applied pressure and deformation of first fluid reservoir portion 2740, the first fluid composition 2910 stored in first fluid reservoir portion 2740 is forced out at least one of the plurality of pores 2734. Also shown is outflow of the second fluid composition 2920 from the penetrating edge 2732 of penetrating device 2710 in response to actuation of initiator 2724. For example, downward pressure on initiator 2724, e.g., a plunger, forces the second fluid composition 2920 from second fluid reservoir portion 2720, through the lumen of penetrating device 2710, and out penetrating edge 2732.

FIG. 29B shows a schematic of fluid flow through a longitudinal cross-section through penetrating system 2700. Shown is deformation of a deformable material of first fluid reservoir portion 2740 in response to applied pressure 2930 resulting from squeezing first fluid reservoir portion 2740 with two or more fingers 2900 as shown in FIG. 29A. Also shown is flow of the first fluid composition (shown as stippling) from the first fluid reservoir portion 2740, through the internal flow conduit 2818, and out at least one of the plurality of pores 2734 in response to deformation of a deformable material of first fluid reservoir portion 2740. Also shown is outflow of the second fluid composition 2920 from the penetrating edge 2732 of penetrating device 2710 in response to actuation of initiator 2724. For example, downward pressure 2940 on initiator 2724, e.g., a plunger, forces the second fluid composition 2920 from second fluid reservoir portion 2720, through lumen 2824 of penetrating device 2710, and out penetrating edge 2732. During an aspiration procedure, upward pressure on initiator 2724 can be used to pull fluid, e.g., second fluid composition 2920 plus any cells and/or tissue captured from a biopsy of an animal subject, back past penetrating edge 2732, through lumen 2824 of penetrating device 2710, and into the second fluid reservoir portion 2720.

In an aspect, the second fluid reservoir portion of a penetrating system is in fluid communication with the second end of the lumen of the penetrating device through a flow conduit. In an aspect, the flow conduit includes tubing, e.g., surgical tubing. FIGS. 30 and 31 illustrate aspects of penetrating systems including a second fluid reservoir portion in fluid communication with the penetrating device through a flow conduit. FIG. 30 is a schematic of an external view of penetrating system 3000. Penetrating system 3000 includes penetrating device 3010 and second fluid reservoir portion 3020. Penetrating device 3010 includes penetrating portion 3030, first fluid reservoir portion 3040, and connector portion 3050. Penetrating portion 3030 includes penetrating edge 3032 and a plurality of pores 3034. Penetrating portion 3030 further includes all or part of the internal components described in FIGS. 27 and 28 including a first hollow cylinder, a second hollow cylinder disposed with the first hollow cylinder, and a first fluid reservoir portion for holding a first fluid composition, the first fluid reservoir portion including a hollow structure with a first end and a second end, the hollow structure disposed over, and substantially coaxial to a region of the second hollow cylinder proximal to the second end of the second hollow cylinder, the first end of the hollow structure secured to the second end of the first hollow cylinder and the second end of the hollow structure secured proximal to the second end of the second hollow cylinder, the hollow structure in fluid communication with an internal fluid conduit and the plurality of pores 3034. Penetrating device 3010 is connected to second fluid reservoir portion 3020 through connector portion 3050 through flow conduit 3060, e.g., surgical tubing.

FIG. 31 is a schematic of an external view of penetrating system 3100. Penetrating system 3000 includes penetrating device 3010 and second fluid reservoir portion 3020 as described in FIG. 30. Penetrating device 3010 is connected to second fluid reservoir portion 3020 through connector portion 3050 through flow conduit 3060, e.g., surgical tubing. System 3100 further includes pump 3110 for initiating flow into or out of second fluid reservoir portion 3020 through flow conduit 3060, connector portion 3050, and through an internal lumen of penetrating device 3010.

In an aspect, a penetrating system, such as described in FIGS. 27-31, further includes a computing component operably coupled to the initiator, the computing component including a microprocessor and circuitry configured to controllably actuate the initiator. In an aspect, a penetrating system, such as described in FIGS. 27-31, further includes at least one sensor. In an aspect, the at least one sensor includes at least one of an accelerometer, a clock, a temperature sensor, a pressure sensor, or a chemical sensor. In an aspect, the penetrating system includes at least one sensor operably coupled to a computing component, the computing component including circuitry configured to controllably actuate the initiator in response to input from the at least one sensor.

Figure 32:
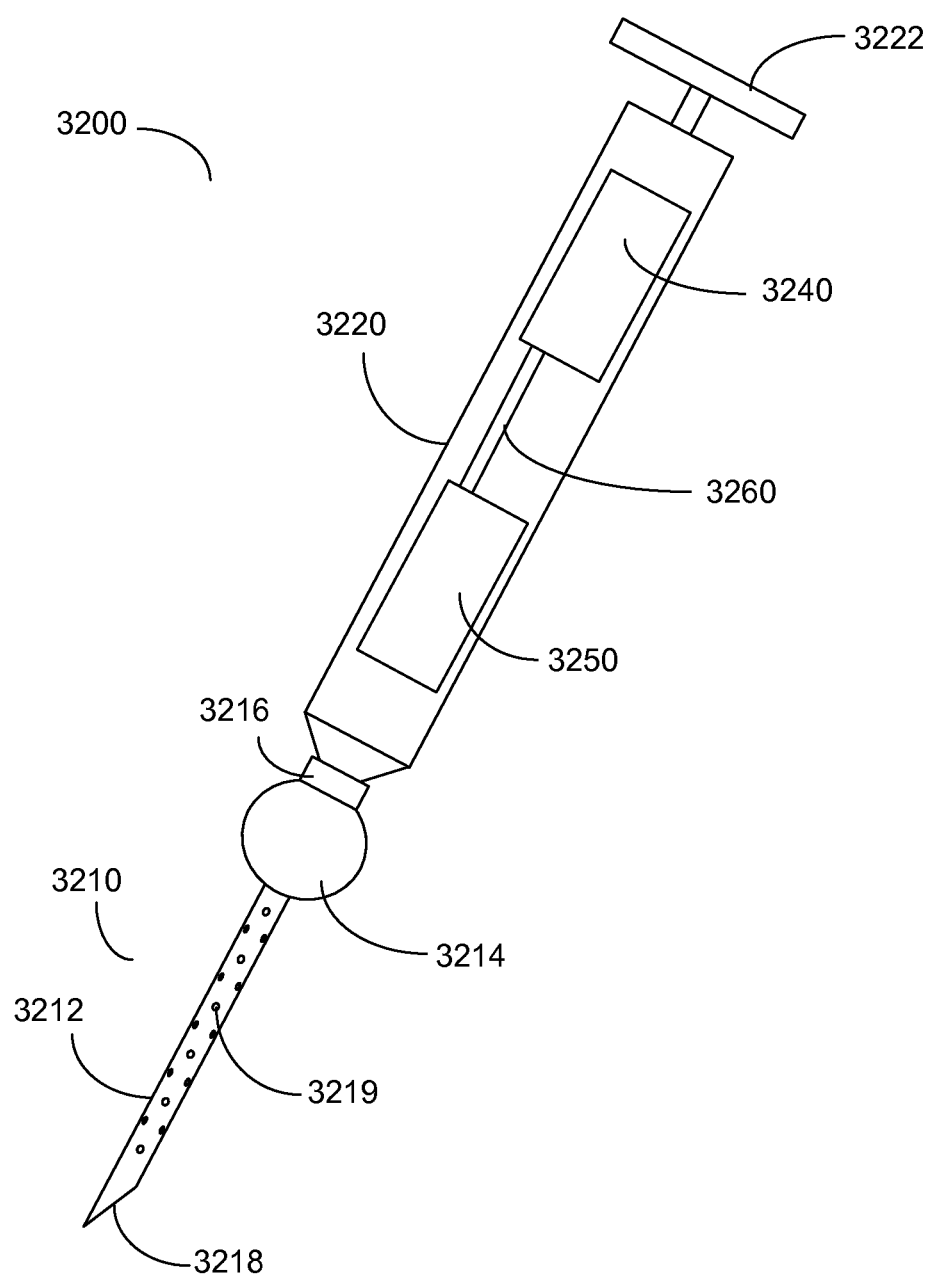
FIG. 32 shows a schematic of a penetrating system including a computing component.

FIG. 32 illustrates aspects of a penetrating system including a computing component and at least one sensor. Penetrating system 3200 includes penetrating device 3210 and second fluid reservoir portion 3220. Penetrating device 3210 includes penetrating portion 3212, first fluid reservoir portion 3214, and connector portion 3216. Penetrating portion 3212 includes penetrating edge 3218 and a plurality of pores 3219. Second fluid reservoir portion 3220 includes initiator 3222. Penetrating system 3200 further includes computing component 3240. In an aspect, computing component 3240 includes a microprocessor and circuitry configured to controllably actuate initiator 3222. Penetrating system 3200 further includes at least one sensor 3250 operably coupled to computing component 3240 through communications link 3260. In an aspect, the at least one sensor includes at least one of an accelerometer, a clock, a temperature sensor, a pressure sensor, a proximity sensor, or a chemical sensor. Computing component 3240 includes circuitry configured to controllably actuate initiator 3222 in response to input from at least one sensor 3250.

Figure 33:
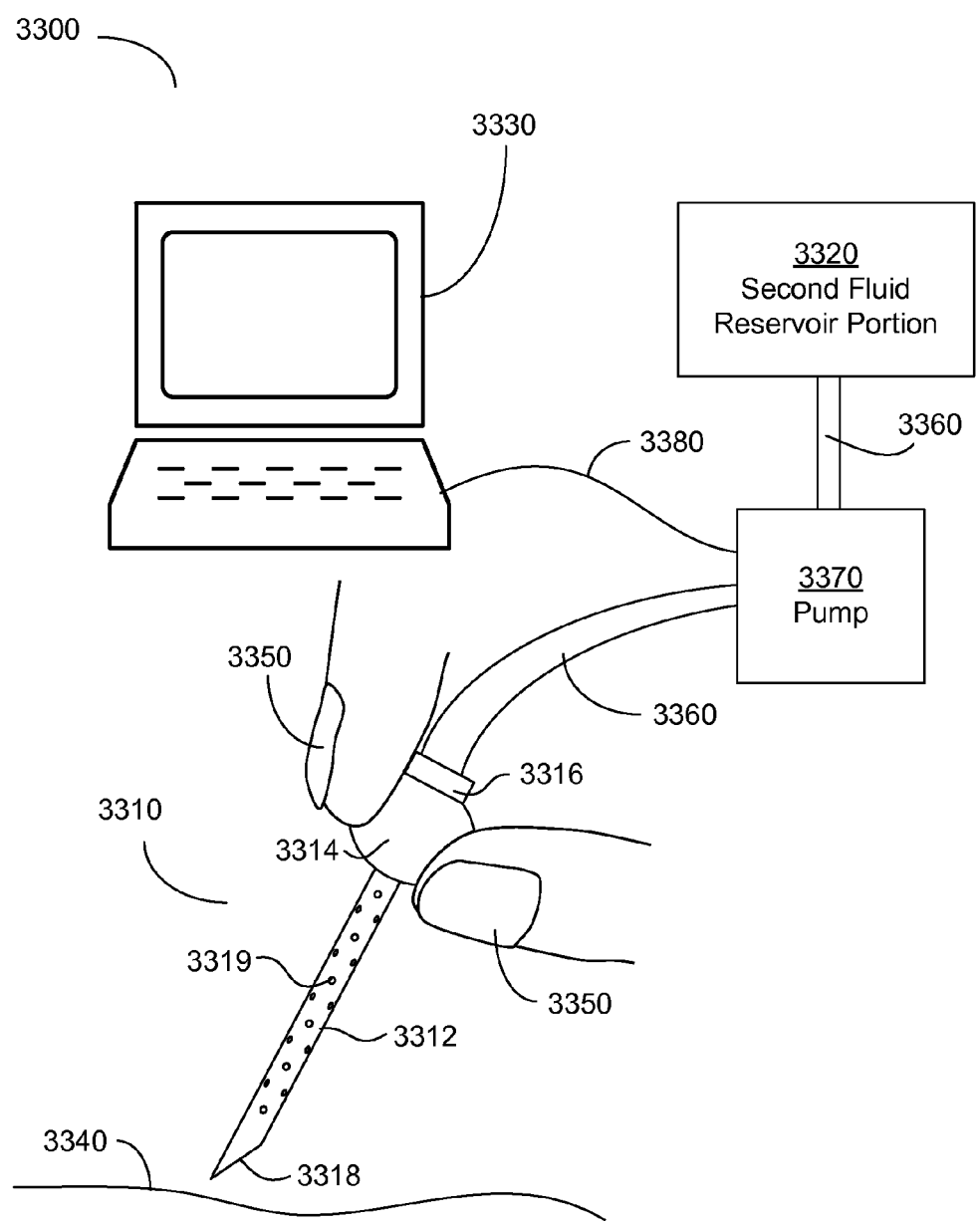
FIG. 33 shows a schematic of a penetrating system including a computing device and a pump.

FIG. 33 illustrates a penetrating system including a computing device. Penetrating system 3300 includes penetrating device 3310, second fluid reservoir portion 3320, and computing device 3330. Penetrating device 3310 includes penetrating portion 3312, first fluid reservoir portion 3314, and connector portion 3316. Penetrating portion 3312 includes penetrating edge 3318 for piercing a material 3340, e.g., a mammalian tissue, and a plurality of pores 3319. First fluid reservoir portion 3314 includes a deformable material, e.g., deformable plastic, that deforms in response to applied pressure, e.g., pressure applied by squeezing with two or more fingers 3350. First fluid reservoir portion 3314 holds a first fluid composition, e.g., an analgesic, and is in fluid communication with the plurality of pores 3319. Connector portion 3316 is in fluid communication with penetrating edge 3318 through a central lumen running longitudinally through penetrating device 3310. Connector portion 3316 is connected through a fluid conduit 3360, e.g., surgical tubing, to pump 3370 and second fluid reservoir portion 3320. In an aspect, the second fluid reservoir portion 3320 holds a second fluid composition, e.g., one or more therapeutic agents. In an aspect, the second fluid reservoir portion 3320 is configured to hold a capture sample, e.g., a blood, biological fluid, or tissue sample. Computing device 3330 is operably coupled to pump 3370 and includes circuitry configured to controllably actuate pump 3370 through a communications link 3380. In an aspect, the penetrating system is used by a healthcare provider to administer a therapeutic agent to a subject. The healthcare provider manually squeezes the deformable material of the first fluid reservoir portion to induce flow of an analgesic, e.g., lidocaine, through the plurality of pores of the penetrating device to coat the penetrating portion prior to or as the penetrating edge is piercing the tissue of the subject. The computing device controls flow of the therapeutic agent from the second fluid reservoir portion, through the fluid conduit and the penetrating device, and into the tissue of the subject. In an aspect, the penetrating system is used by a healthcare provider to perform an aspirating biopsy. The healthcare provider manually squeezes the deformable material of the first fluid reservoir portion to induce flow of a lubricant through the plurality of pores of the penetrating device to coat the penetrating portion prior to or as the penetrating edge is piercing the tissue of the subject. The computing device controls a pump, e.g., an aspirating pump, to aspirate a captured sample, e.g., an ascites sample, from the subject and into the second fluid reservoir portion. In an aspect, the penetrating system includes at least one sensor (e.g., an accelerometer, a clock, a temperature sensor, a pressure sensor, a proximity sensor, or a chemical sensor) operably coupled to the computing device, the computing device including circuitry configured to controllably actuate the pump in response to input from the at least one sensor.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors. A data processing system can be implemented utilizing suitable commercially available components, such as those typically found in data computing/communication and/or network computing/communication systems.

This application may make reference to one or more trademarks, e.g., a word, letter, symbol, or device adopted by one manufacturer or merchant and used to identify and/or distinguish his or her product from those of others. Trademark names used herein are set forth in such language that makes clear their identity, that distinguishes them from common descriptive nouns, that have fixed and definite meanings, or, in many if not all cases, are accompanied by other specific identification using terms not covered by trademark. In addition, trademark names used herein have meanings that are well-known and defined in the literature, or do not refer to products or compounds for which knowledge of one or more trade secrets is required in order to divine their meaning. All trademarks referenced in this application are the property of their respective owners, and the appearance of one or more trademarks in this application does not diminish or otherwise adversely affect the validity of the one or more trademarks. All trademarks, registered or unregistered, that appear in this application are assumed to include a proper trademark symbol, e.g., the circle R or bracketed capitalization (e.g., [trademark name]), even when such trademark symbol does not explicitly appear next to the trademark. To the extent a trademark is used in a descriptive manner to refer to a product or process, that trademark should be interpreted to represent the corresponding product or process as of the date of the filing of this patent application.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Various non-limiting embodiments are described herein as Prophetic Examples.

Prophetic Example 1: Manufacture of an Injection System with a Porous Outer Hollow Cylinder, a Nonporous Inner Hollow Cylinder and Two Concentric Plungers Controlled by Microcircuitry An injection system is constructed with two concentric hollow cylinders forming a penetrating portion and two concentric plungers (e.g., see FIGS. 1 and 2) and controlled by a microprocessor and microcircuitry. A pressure sensor on the device signals when skin or tissue is contacted and the microprocessor initiates deployment of the penetrating portion, and delivery of lubricants, analgesics/anesthetics and vaccines and/or therapeutic agents from the concentric hollow cylinders. Upon completion of drug delivery, the penetrating portion is retracted by the device and information on the injection is transmitted to a central computer.

An injection device with two concentric hollow cylinders and two concentric plungers is constructed from stainless steel and plastics. The outer hollow cylinder contains pores to allow the outflow of analgesics and lubricants which reduce the pain associated with intramuscular injections. For example, the outer hollow cylinder may be fabricated from stainless steel (SS) by pulling heated SS tubes through circular dies to obtain the desired diameter of the hollow cylinder, and then pores may be introduced in the hollow cylinder by micromachining Penetrating devices with lateral pores are described (see e.g., U.S. Pat. No. 6,517,521 issued to Ly on Feb. 11, 2003, which is incorporated herein by reference). Processes and technologies to manufacture custom syringes and needles are available (see e.g., CregannaInfoSheet from Creganna-Tactx Medical, Campbell, Calif.) For example, a 19 gauge (0.686 mm inner diameter), 2.54 cm outer hollow cylinder may be manufactured with approximately 0.050 cm diameter pores spaced approximately 0.08 cm apart for the length of the outer hollow cylinder by micromachining. An inner hollow cylinder, approximately 23 gauge (0.641 mm outer diameter), 2.54 cm long is fabricated and inserted in the outer hollow cylinder. Both hollow cylinders are processed by laser cutting and grinding to create a sharp edge tip (see FIG. 1). Stainless steel circular end pieces and collars (or connectors) are produced by micromachining and micro-welded to the ends of the inner and outer hollow cylinders (see FIGS. 1 and 2). The barrel of the device including concentric plungers and the inner and outer reservoirs are fabricated by injection molding from polypropylene. Materials and methods for syringe construction are described (see e.g., U.S. Patent Appl. No. 2010/0179478 by Kobayashi et al. published on Jul. 15, 2010 and U.S. Appl. No. 2007/0083155 by Muller published on Apr. 12, 2007, which are incorporated herein by reference). A touch sensor is attached to the distal end of the device to detect contact of the device with the skin. For example, a Force Sensing Resister is available from Interlink Electronics, Inc., Camarillo, Calif. which signals the microprocessor when the injection device contacts the skin surface. The microprocessor initiates actuation of the outer plunger to drive lubricant and anesthetic through the pores of the outer hollow cylinder to the exterior. For example the lubricant may be polydimethylsiloxane (available from Dow-Corning, Midland, Mich.) and organosiloxanes (see e.g., U.S. Pat. No. 5,911,711 issued to Pelkey on Jun. 15, 1999 which is incorporated herein by reference), and the anesthetic may be Lidocaine Hydrochloride Solution 4% (available from Morton Grove Pharmaceuticals, Morton Grove, Ill.). The electronically actuated penetrating portion is deployed at a predetermined depth (approximately 3.75 cm to achieve intramuscular delivery in an average adult male deltoid muscle) as lubricant and analgesic flow from the pores in the outer hollow cylinder. Electromechanical devices to insert syringes are described (see e.g., U.S. Pat. No. 8,308,741 and U.S. Pat. No. 6,547,755 which are incorporated herein by reference). For example a micro linear actuator with a range of 50 mm and accuracy of 15 μm is available from Zaber Technologies Inc., Vancouver, B.C., Canada (see e.g., Micro Linear Actuator Spec Sheet available online at http://www.zaber.com/products/product_detail.php?detail=T-NA08A25-SV2 which is incorporated herein by reference). Electromechanical actuators with integrated controllers are also used to drive the outer and inner plungers. After the penetrating portion is inserted the inner plunger is actuated and medicament is delivered intramuscularly. Completion of delivery, as sensed by movement of the actuator leads to retraction of the penetrating portion and transmission of data from the injection system to a central computer. The date, time, location, medicament, dosage, injection site (e.g., deltoid muscle on right arm) are transmitted to a central computer and incorporated in the patient electronic health record.

Prophetic Example 2: An Injection System with Concentric Hollow Cylinders and a Single Plunger to Deliver a Vaccine, Lubricants and Anesthetics at an Injection Site An injection system is constructed with two concentric hollow cylinders forming a penetrating portion and a single plunger. The outer hollow cylinder is porous and served by a first fluid reservoir portion capped by a deformable membrane and holding a first fluid composition, e.g., lubricants and anesthetic, and the inner hollow cylinder is nonporous and served by a second fluid reservoir portion holding a second fluid composition, e.g., a vaccine or a therapeutic agent (e.g., see FIGS. 19A and 19B). Fluid flow from both reservoirs is controlled by a plunger which applies force directly to the vaccine in the second fluid reservoir portion, and indirectly to the deformable membrane on the first fluid reservoir portion, thereby driving the lubricants and anesthetic from the first fluid reservoir portion and laterally out the porous outer hollow cylinder (see FIG. 22B). The device contains sensors, actuators, microcircuitry and microprocessors to guide the injection and to record and transmit data from the injection.

The injection system includes an outer hollow cylinder which is porous and designed for lateral delivery of lubricants and anesthetics, and an inner hollow cylinder which is coaxial and nonporous for delivery of a second fluid composition, e.g., a vaccine or therapeutic agent. The injection device includes two reservoirs, a first fluid reservoir portion and a second fluid reservoir portion which serve the outer and inner hollow cylinder respectively. The outer hollow cylinder is constructed of a polymer with pores present on the sides of the outer hollow cylinder (see FIGS. 18A and 18B). For example, a microporous polymer of polypropylene may have pores approximately 5 microns in diameter which allow fluid flow (see e.g., U.S. Pat. No. 4,186,745 issued to Lewis et al. on Feb. 5, 1980 which is incorporated herein by reference). In contrast, the inner hollow cylinder is constructed of a nonporous polymer. Methods and materials to construct plastic needles are described (see, e.g., Kim & Colton (2005) J. Med. Eng. Technol. 29:181-186, which is incorporated herein by reference). A substantially ring-shaped first end piece at the penetrating edge is formed from nonporous polymer by injection molding and cast in place to seal the knife edge tip of the injection device, and a flexible substantially ring-shaped second end piece is placed between the inner and outer hollow cylinders in the connector portion of the device to cap the first fluid reservoir portion (see FIGS. 19A and 19B). For example a substantially ring-shaped second end piece of a flexible polymer (e.g., butadiene) may be attached to the inner and outer hollow cylinders with an adhesive or by fusing the end piece to the hollow cylinders with heat or microwaves (see e.g., U.S. Patent Appl. No. 2010/0179478, Ibid.). The first fluid reservoir portion may be filled with lubricant and anesthetic prior to attaching the upper end piece or a syringe may be used to fill the first fluid reservoir portion by injection through the flexible upper end piece. For example the lubricant may be polydimethylsiloxane (available from Dow-Corning, Midland, Mich.) and organosiloxanes (see e.g., U.S. Pat. No. 5,911,711 issued to Pelkey on Jun. 15, 1999, which is incorporated herein by reference), and the anesthetic may be Lidocaine Hydrochloride Solution 4% (available from Morton Grove Pharmaceuticals, Morton Grove, Ill.). The uppermost end of the outer hollow cylinder (i.e., the connector portion; see FIGS. 19A and 19B) may be constructed of nonporous polymer and in the form of a Luer-lock fitting which connects to a syringe with a corresponding Luer-lock male fitting. The syringe barrel forms the second fluid reservoir portion which contains and delivers vaccines and/or therapeutic agents from the sharp edge tip of the penetrating portion when force is applied to the syringe plunger. In addition, fluid pressure on the deformable membrane covering the first fluid reservoir portion drives lubricant and anesthetic from the first fluid reservoir portion through the lateral pores in the outer hollow cylinder. See, e.g., FIG. 19B.

The injection device includes microcircuitry, microprocessors and sensors to detect, record and report injections to a central computer system. For example an accelerometer may detect the motion associated with inserting the penetrating portion in the deltoid muscle of a patient and a pressure sensor may detect the application of force to a syringe plunger. The injection data are recorded by the microprocessor and transmitted to a central computer. For example the sensors may record motion and pressure consistent with injection of a 0.5 mL dose of vaccine intramuscularly. The date, time, patient identification, vaccine lot number, and other information, such as insurance company, healthcare worker, clinic location, are transmitted to a centralized computer (or a cloud computer) and added to the patient's electronic health record.

Prophetic Example 3: An Injection System for Delivery of Medicaments with Two Concentric Hollow Cylinders and Two Reservoirs which Delivers Anesthetics and Lubricants to Reduce the Pain Associated with Intramuscular Injections An injection device is constructed with two concentric hollow cylinders forming a penetrating portion and two reservoirs which deliver to an injection site a first fluid composition, e.g., lubricants and anesthetics, from a first fluid reservoir portion and a second fluid composition, e.g., a vaccine, from a second fluid reservoir portion. A first fluid reservoir portion is constructed as a flexible bulb which is manually compressed to drive lubricants and anesthetic from the first fluid reservoir portion through pores in an outer hollow cylinder. See FIGS. 29A and 29B. Insertion of the penetrating portion into muscle tissue and initiation of flow of the vaccine from the second fluid reservoir portion is initiated by an automated system which is controlled by microcircuitry and microprocessors on the device.

The injection device with concentric hollow cylinders and two fluid reservoirs is constructed from stainless steel and polymers. The outer hollow cylinder contains pores to allow lateral outflow of analgesics and lubricants which reduce the pain associated with intramuscular injections. For example, the outer hollow cylinder may be fabricated from stainless steel (SS) by pulling heated SS tubes through circular dies to obtain the desired diameter of the hollow cylinder, and then pores may be introduced in the hollow cylinder by micromachining Penetrating devices with lateral pores are described (see e.g., U.S. Pat. No. 6,517,521 issued to Ly on Feb. 11, 2003, which is incorporated herein by reference), and processes and technologies to manufacture custom syringes and needles are available (see e.g., CregannaInfoSheet from Creganna-Tactx Medical, Campbell, Calif.). For example a 19 gauge (0.686 mm inner diameter), 2.54 cm outer hollow cylinder may be manufactured with approximately 0.050 cm diameter pores spaced approximately 0.08 cm apart for the length of the outer hollow cylinder by micromachining. An inner hollow cylinder, approximately 23 gauge (0.641 mm outer diameter), 3.18 cm long is fabricated for insertion through the smaller spherical reservoir and the outer hollow cylinder (see FIG. 28B). A stainless steel ring-shaped end piece is produced by micromachining and micro-welded to the distal, penetrating end of the inner and outer hollow cylinders and both hollow cylinders are processed by laser cutting and grinding to create a sharp beveled tip (see FIG. 28B). The first fluid reservoir portion is fabricated using injection molding to create a spherical reservoir approximately 6 mm in diameter from flexible polypropylene. The spherical reservoir may have a pressure sensor to detect compression of the spherical reservoir. For example, a Force Sensing Resister is available from Interlink Electronics, Inc., Camarillo, Calif. which signals the microprocessor when the spherical reservoir is squeezed. The spherical reservoir is attached to the top of the outer hollow cylinder and the connector portion of the inner hollow cylinder (see, e.g., FIG. 28B) using adhesives and heat fusion to join the SS and polypropylene components (see e.g., U.S. Patent Appl. No. 2010/0179478, Ibid.). The connector portion of the inner hollow cylinder may be constructed as a Luer-lock fitting which can accept a male syringe fitting. The barrel of the syringe forms the second fluid reservoir portion and the syringe plunger drives flow of fluid from the second fluid reservoir portion through the penetrating end of the inner hollow cylinder for intramuscular delivery of the vaccine. The syringe plunger is actuated by an actuator that is controlled by the microprocessor on the injection system. For example a micro linear actuator with a range of 50 mm and accuracy of 15 µm is available from Zaber Technologies Inc., Vancouver, B.C., Canada (see e.g., Micro Linear Actuator Spec Sheet available online at http://www.zaber.com/products/product_detail.php?detail=T-NA08A25-SV2 which is incorporated herein by reference).

The injection system is assembled after entering health record data into a central computer which communicates with the injection system device. The date, time, location, patient name, medication, route of delivery (e.g., intramuscular), lubricants, anesthetic and health care worker are entered and the appropriate injection system is indicated. For example, an intramuscular injection of an influenza vaccine in an adult male selects an injection system with approximately 0.5 mL of vaccine in the large reservoir (i.e. the syringe barrel) and 0.25 mL of lubricant plus anesthetic in the small reservoir. The injection procedure follows: Holding the injection device near the injection site (e.g., arm) the first fluid reservoir portion is manually compressed forcing anesthetic and lubricant out the plurality of pores along the length of the outer hollow cylinder (see, e.g., FIG. 29A), and the pressure sensor on the first fluid reservoir portion signals the processor to initiate deployment of the penetrating portion and vaccine delivery. The electronically actuated penetrating portion is deployed at a predetermined depth (approximately 3.75 cm to achieve intramuscular delivery in an average adult male deltoid muscle) as lubricant and analgesic flow from the pores in the outer hollow cylinder. Electromechanical devices to insert syringes are described (see e.g., U.S. Pat. No. 8,308,741 and U.S. Pat. No. 6,547,755 which are incorporated herein by reference). Following deployment the microprocessor initiates vaccine delivery by signaling the linear actuator to drive the syringe plunger. Following vaccine delivery the penetrating portion is automatically retracted and the cumulative injection data is transmitted to a central computer.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A penetrating device, comprising:
a first hollow cylinder having a first end and a second end, the first hollow cylinder including a plurality of pores;
a second hollow cylinder having a first end and a second end, the second hollow cylinder disposed within the first hollow cylinder and substantially coaxial to the first hollow cylinder, the second end of the second hollow cylinder having a connector portion;
a substantially ring-shaped end piece having an outer edge and an inner edge, the outer edge of the substantially ring-shaped end piece secured to the first end of the first hollow cylinder and the inner edge of the substantially ring-shaped end piece secured to the first end of the second hollow cylinder, wherein the first hollow cylinder, the second hollow cylinder, and the substantially ring-shaped end piece form a penetrating edge;
an internal fluid conduit defined by a space between the first hollow cylinder and the substantially coaxial second hollow cylinder, the internal fluid conduit in fluid communication with the plurality of pores along a length of the first hollow cylinder;
a fluid reservoir portion for holding a fluid composition, the fluid reservoir portion including a hollow structure with a first end and a second end, the hollow structure disposed over, and substantially coaxial to a region of the second hollow cylinder proximal to the second end of the second hollow cylinder, the first end of the hollow structure secured to the second end of the first hollow cylinder and the second end of the hollow structure secured proximal to the second end of the second hollow cylinder, the hollow structure in fluid communication with the internal fluid conduit, wherein the hollow structure of the fluid reservoir portion is formed at least in part from a deformable material; and a lumen defined by the second hollow cylinder, the lumen having a first end and a second end, the first end of the lumen in fluid communication with the penetrating edge.

2. The device of claim 1, wherein the first hollow cylinder is formed from a porous material.

3. The device of claim 1, wherein each of the plurality of pores is machined into the first hollow cylinder.

4. The device of claim 1, wherein each of the plurality of pores is substantially perpendicular to a central axis of the first hollow cylinder.

5. The device of claim 1, wherein the connector portion of the second end of the second hollow cylinder is configured to connect to a second fluid reservoir portion.

6. The device of claim 5, wherein the second fluid reservoir portion includes a syringe.

7. The device of claim 1, wherein the connector portion of the second end of the second hollow cylinder includes a fitting sized for attachment to a syringe, the syringe including a second fluid reservoir portion.

8. The device of claim 1, wherein the second hollow cylinder and the substantially ring-shaped end piece are substantially non-porous.

9. The device of claim 1, wherein the penetrating edge includes at least one sharp edge able to pierce a material.

10. The device of claim 1, wherein the deformable material of the hollow structure of the fluid reservoir portion includes at least one of a deformable plastic, a deformable polymer, a deformable rubber, or a deformable metal.

11. The device of claim 1, wherein the deformable material of the hollow structure of the fluid reservoir portion includes a thin wall of deformable material.

12. The device of claim 1, wherein the deformable material of the hollow structure of the fluid reservoir portion is deformable in response to applied pressure.

13. The device of claim 1, wherein deformation of the deformable material of the hollow structure of the fluid reservoir portion induces flow of the fluid composition from the fluid reservoir portion, through the internal fluid conduit, and out at least one of the plurality of pores.

14. The device of claim 1, wherein the deformable material of the hollow structure of the fluid reservoir portion includes electro-active polymer, electro-active metal, magnetically responsive material, thermo-responsive material, photo-responsive material, or acoustically responsive material.

15. The device of claim 14, wherein the deformable material of the hollow structure of the fluid reservoir portion is deformable in response to applied energy.

16. The device of claim 1, wherein the fluid composition of the fluid reservoir portion includes at least one of an anesthetic, a lubricant, an antimicrobial agent, an analgesic, a treatment agent, a sealant, an anticoagulant, or an anti-hemorrhagic agent.

17. The device of claim 1, wherein the second end of the lumen defined by the second hollow cylinder is in fluid communication with a second fluid reservoir portion.

18. A penetrating system, comprising:
a penetrating device including
a first hollow cylinder having a first end and a second end, the first hollow cylinder including a plurality of pores;
a second hollow cylinder having a first end and a second end, the second hollow cylinder disposed within the first hollow cylinder and substantially coaxial to the first hollow cylinder, the second end of the second hollow cylinder having a connector portion;
a substantially ring-shaped end piece having an outer edge and an inner edge, the outer edge of the substantially ring-shaped end piece secured to the first end of the first hollow cylinder and the inner edge of the substantially ring-shaped end piece secured to the first end of the second hollow cylinder, wherein the first hollow cylinder, the second hollow cylinder, and the substantially ring-shaped end piece form a penetrating edge;
an internal fluid conduit defined by a space between the first hollow cylinder and the substantially coaxial second hollow cylinder, the internal fluid conduit in fluid communication with the plurality of pores along a length of the first hollow cylinder;
a first fluid reservoir portion for holding a first fluid composition, the first fluid reservoir portion including a hollow structure with a first end and a second end, the hollow structure disposed over, and substantially coaxial to a region of the second hollow cylinder proximal to the second end of the second hollow cylinder, the first end of the hollow structure secured to the second end of the first hollow cylinder and the second end of the hollow structure secured proximal to the second end of the second hollow cylinder, the hollow structure in fluid communication with the internal fluid conduit, wherein the hollow structure of the first fluid reservoir portion is formed at least in part from a deformable material; and
a lumen defined by the second hollow cylinder, the lumen having a first end and a second end, the first end of the lumen in fluid communication with the penetrating edge; and
a second fluid reservoir portion including an initiator, the second fluid reservoir portion attached to the penetrating device through the connector portion of the second hollow cylinder, the second fluid reservoir portion in fluid communication with the second end of the lumen defined by the second hollow cylinder.

19. The system of claim 18, wherein each of the plurality of pores is substantially perpendicular to a central axis of the first hollow cylinder.

20. The system of claim 18, wherein the connector portion of the second end of the second hollow cylinder includes a fitting sized for attachment to the second fluid reservoir portion.

21. The system of claim 18, wherein the second hollow cylinder and the substantially ring-shaped end piece are substantially non-porous.

22. The system of claim 18, wherein the penetrating edge includes at least one sharp edge able to pierce a material.

23. The system of claim 18, wherein the deformable material of the hollow structure of the first fluid reservoir portion includes at least one of a deformable plastic, a deformable polymer, a deformable rubber, or a deformable metal.

24. The system of claim 18, wherein the deformable material of the hollow structure of the first fluid reservoir portion includes a thin wall of deformable material.

25. The system of claim 18, wherein the deformable material of the hollow structure of the first fluid reservoir portion is deformable in response to applied pressure.

26. The system of claim 18, wherein deformation of the deformable material of the hollow structure of the first fluid reservoir portion induces flow of the first fluid composition from the first fluid reservoir portion, through the internal fluid conduit, and out at least one of the plurality of pores.

27. The system of claim 18, wherein the deformable material of the hollow structure of the first fluid reservoir portion includes electro-active polymer, electro-active metal, magnetically responsive material, thermo-responsive material, photo-responsive material, or acoustically responsive material.

28. The system of claim 27, wherein the deformable material of the hollow structure of the first fluid reservoir portion is deformable in response to applied energy.

29. The system of claim 18, wherein the first fluid composition of the first fluid reservoir portion includes at least one anesthetic, lubricant, antimicrobial agent, analgesic, sealant, treatment agent, anticoagulant, or antihemorrhagic agent.

30. The system of claim 18, wherein the second fluid reservoir portion includes a syringe.

31. The system of claim 18, wherein the initiator includes a plunger.

32. The system of claim 18, wherein the initiator includes a pump.

33. The system of claim 18, wherein the initiator is configured to induce flow into or out of the second fluid reservoir portion through the lumen defined by the second hollow cylinder of the penetrating device.

34. The system of claim 18, wherein the second fluid reservoir portion is in fluid communication with the second end of the lumen of the penetrating device through a flow conduit.

35. The system of claim 18, wherein the second fluid reservoir portion is configured to hold a second fluid composition.

36. The system of claim 35, wherein the second fluid composition includes at least one vaccine, therapeutic agent, or dye.

37. The system of claim 18, wherein the second fluid reservoir portion is configured to hold a captured sample.

38. The system of claim 18, further comprising a computing component operably coupled to the initiator, the computing component including a microprocessor and circuitry configured to controllably actuate the initiator.

39. The system of claim 18, further comprising at least one sensor operably coupled to a computing component, the computing component including circuitry configured to controllably actuate the initiator in response to input from the at least one sensor.

* * * * *